US009488911B2

(12) United States Patent
Tsuchimura et al.

(10) Patent No.: US 9,488,911 B2
(45) Date of Patent: Nov. 8, 2016

(54) PHOTOSENSITIVE COMPOSITION, PHOTOCURABLE COMPOSITION, CHEMICAL AMPLIFICATION RESIST COMPOSITION, RESIST FILM, PATTERN FORMING METHOD, METHOD OF MANUFACTURING ELECTRONIC DEVICE AND ELECTRONIC DEVICE

(71) Applicant: FUJIFILM Corporation, Tokyo (JP)

(72) Inventors: Tomotaka Tsuchimura, Shizuoka (JP); Kyouhei Sakita, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/831,801

(22) Filed: Aug. 20, 2015

(65) Prior Publication Data

US 2015/0362836 A1  Dec. 17, 2015

Related U.S. Application Data

(63) Continuation of application No. PCT/JP2014/051142, filed on Jan. 21, 2014.

(30) Foreign Application Priority Data

Feb. 21, 2013  (JP) ................... 2013-032585

(51) Int. Cl.
| | | |
|---|---|---|
| G03F 7/004 | (2006.01) | |
| G03F 7/20 | (2006.01) | |
| G03F 7/32 | (2006.01) | |
| G03F 7/039 | (2006.01) | |
| G03F 7/038 | (2006.01) | |
| C07D 277/64 | (2006.01) | |
| C07D 277/84 | (2006.01) | |
| C07D 413/12 | (2006.01) | |

(52) U.S. Cl.
CPC .......... *G03F 7/0045* (2013.01); *C07D 277/64* (2013.01); *C07D 277/84* (2013.01); *C07D 413/12* (2013.01); *G03F 7/038* (2013.01); *G03F 7/0382* (2013.01); *G03F 7/0387* (2013.01); *G03F 7/0392* (2013.01); *G03F 7/0395* (2013.01); *G03F 7/0397* (2013.01); *G03F 7/20* (2013.01); *G03F 7/2059* (2013.01); *G03F 7/32* (2013.01); *G03F 7/322* (2013.01); *G03F 7/325* (2013.01)

(58) Field of Classification Search
None
See application file for complete search history.

(56) References Cited

U.S. PATENT DOCUMENTS

| | | | | |
|---|---|---|---|---|
| 4,282,309 A | * | 8/1981 | Laridon | .................. C08F 2/50 430/281.1 |
| 6,245,478 B1 | | 6/2001 | Uetani et al. | |
| 6,544,712 B1 | * | 4/2003 | Tachikawa | ............ G03F 7/0045 430/170 |
| 2002/0060771 A1 | * | 5/2002 | Sumino | ............... G02F 1/13394 349/156 |
| 2006/0211785 A1 | | 9/2006 | Aoai | |
| 2012/0006788 A1 | | 1/2012 | Fujimori et al. | |
| 2012/0202158 A1 | | 8/2012 | Hatakeyama et al. | |
| 2015/0064623 A1 | | 3/2015 | Oishi et al. | |

FOREIGN PATENT DOCUMENTS

| | | |
|---|---|---|
| JP | 60-008253 | 1/1985 |
| JP | 10-077264 | 3/1998 |
| JP | 10-083079 | 3/1998 |
| JP | 2000-010270 | 1/2000 |
| JP | 2000-098611 | 4/2000 |
| JP | 2006-257248 | 9/2006 |
| JP | 2010-037215 | 2/2010 |
| JP | 2010-122421 | 6/2010 |
| JP | 2011-095635 | 5/2011 |
| JP | 2011-107199 | 6/2011 |
| JP | 2011-190241 | 9/2011 |
| JP | 2012-048155 | 3/2012 |
| JP | 2012-113256 | 6/2012 |
| JP | 2012-181510 | 9/2012 |
| KR | 1020120030994 | 3/2012 |

(Continued)

OTHER PUBLICATIONS

Machine-assisted English translation for KR 10-2012-0040985 A (2012).*
English abstract for KR 10-2012-0040985 A (2012).*

(Continued)

*Primary Examiner* — Sin Lee
(74) *Attorney, Agent, or Firm* — Jianq Chyun IP Office

(57) ABSTRACT

There is provided a photosensitive composition containing a compound represented by Formula (I), and the Formula (I) is defined as herein,

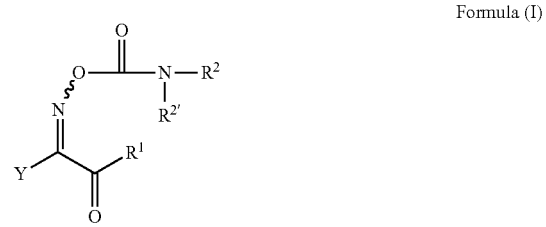

Formula (I)

and chemical amplification resist composition containing the photosensitive composition, wherein the photosensitive composition further contains a compound capable of generating an acid upon irradiation with an actinic ray or radiation, and a chemical amplification resist composition containing the photosensitive composition, wherein the photosensitive composition further contains a compound capable of generating an acid upon irradiation with an actinic ray or radiation.

17 Claims, No Drawings

(56) References Cited

FOREIGN PATENT DOCUMENTS

| KR | 10-2012-0040985 A | * | 4/2012 |
|----|-------------------|---|--------|
| KR | 20120040985 | | 4/2012 |
| WO | 2013/141014 | | 8/2015 |

OTHER PUBLICATIONS

"Written Opinion of the International Searching Authority of PCT/JP2014/051142", mailed on Feb. 18, 2014, with English translation thereof, pp. 1-9.

Shirai et al., "Photoacid and Photobase Generators: Prospects and Their Use in the Development of Polymeric Photosensitive Systems", Bulletin of the Chemical Society of Japan, Nov. 1998, pp. 2483-2507, vol. 71.

"International Search Report of PCT/JP2014/051142 (Form PCT/ISA/210)", mailed on Feb. 8, 2014, with English translation thereof, pp. 1-4, in which 11 of the listed references (JP2010-122421, U.S. Pat. No. 6,245,478, JP2000-098611, JP2011-095635, JP2012-181510, US2012/0202158, JP2006-257248, US2006/0211785, JP60-008253, WO2013/141014 and US2015/0064623) were cited.

"Office Action of Japan Counterpart Application", issued on Mar. 22, 2016, pp. 1-8, with machine English translation thereof.

"Office Action of Korea Counterpart Application" with machine English translation, issued on Aug. 23, 2016, p. 1-p. 9.

* cited by examiner

PHOTOSENSITIVE COMPOSITION, PHOTOCURABLE COMPOSITION, CHEMICAL AMPLIFICATION RESIST COMPOSITION, RESIST FILM, PATTERN FORMING METHOD, METHOD OF MANUFACTURING ELECTRONIC DEVICE AND ELECTRONIC DEVICE

CROSS REFERENCE TO RELATED APPLICATION

This is a continuation of International Application No. PCT/JP2014/051142 filed on Jan. 21, 2014, and claims priority from Japanese Patent Application No. 2013-032585 filed on Feb. 21, 2013, the entire disclosures of which are incorporated therein by reference.

TECHNICAL FIELD

The present invention relates to a photosensitive composition (hereinafter, which may be simply referred as "composition of the present invention").

More specifically, the present invention relates to a photocurable composition suitable for forming a planarization film, a protective film or an interlayer insulation film in an electronic component such as a liquid crystal display device, an organic EL display device, an integrated circuit device, and a solid-state imaging device.

Further more specifically, the present invention relates to a pattern forming method, a chemical amplification resist composition, a resist film using the same, an electronic device manufacturing method using the same, and the electronic device which are suitably used for an ultra-micro lithographic process such as manufacturing of a super LSI or a high capacity microchip, or other photo-fabrication processes.

BACKGROUND ART

In an organic EL display device, or a liquid crystal display device, a patterned interlayer insulating film is formed. In the formation of the interlayer insulating film, a photosensitive resin composition has been widely used because it requires a small number of processes for obtaining a required pattern shape, and further achieves a sufficient flatness. As for the photosensitive resin composition, for example, those described in Patent Documents 1 to 3 have been known.

Also, in a manufacturing process of a semiconductor device such as an IC or an LSI, a microfabrication has conventionally been performed through a lithography using a photoresist composition added with a predetermined component as well as a photosensitive resin composition. With recent high integration of an integrated circuit, it has been required to form an ultrafine pattern in a sub-micron or quarter-micron region. Accordingly, there is a tendency that the exposure wavelength also becomes shorter (from g line to i line, further to KrF excimer laser light). Further, at present, lithography using electron beam, X rays or EUV light other than excimer laser light is being developed. As for the photoresist composition, those described in, for example, Patent Documents 4 to 8 and Non-Patent Document 1 are known.

PRIOR ART DOCUMENTS

Patent Documents

Patent Document 1: Japanese Patent Application Laid-Open No. 2012-113256
Patent Document 2: Japanese Patent Application Laid-Open No. 2011-190241
Patent Document 3: Japanese Patent Application Laid-Open No. 2011-107199
Patent Document 4: Japanese Patent Application Laid-Open No. H10-77264
Patent Document 5: Japanese Patent Application Laid-Open No. 2000-10270
Patent Document 6: Japanese Patent Application Laid-Open No. 2010-37215
Patent Document 7: Japanese Patent Application Laid-Open No. 2012-48155
Patent Document 8: Japanese Patent Application Laid-Open No. H10-83079

Non-Patent Document

Non-Patent Document 1: Bull. Chem. Soc. Jpn., 71(1998) 2483-2507

SUMMARY OF THE INVENTION

Problems to be Solved by the Invention

However, the above described photosensitive composition described in Patent Documents 1 to 3 needs to be further improved in view of the sensitivity, the solvent resistance, the thermal stability, the reaction contrast, the residual film ratio and the developability, and also the above described photoresist composition described in Patent Documents 4 to 8 and Non-Patent Document 1 needs to be further improved in view of the resolution, the LER performance, the shape of a formed pattern and the scum performance, with recent miniaturization of a pattern.

An object of the present invention is to provide a photosensitive composition which contains a compound having a specific structure and thus efficiently generates a base. Particularly, when the photosensitive composition is used as a photocurable composition, the sensitivity, reaction contrast and developability are excellent, and the residual film ratio, solvent resistance and thermal stability of a formed cured film are excellent, and when the photosensitive composition is used as a resist composition, the resolution, and LER performance, and the shape and scum performance of a formed pattern are excellent.

Means for Solving the Problems

The present invention has the following configuration, thereby achieving the object of the present invention.

[1] A photosensitive composition containing a compound represented by the following Formula (I):

[Chem. 1]

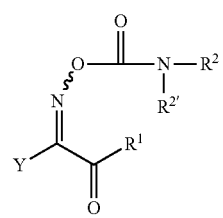

Formula (I)

in Formula (I),
Y represents a monovalent organic group,
$R^1$ represents a monovalent organic group,
each of $R^2$ and $R^{2'}$ independently represents a hydrogen atom, an alkyl group, a cycloalkyl group, an aryl group, or a heteroaryl group, and $R^2$ and $R^{2'}$ may be bound with each other to form a nitrogen-containing heterocyclic group.

[2] The photosensitive composition as described in [1], wherein in Formula (I) above, Y represents a heterocyclic group.
[3] The photosensitive composition as described in [1] or [2],
wherein the compound represented by Formula (I) is a compound represented by the following Formula (II):

[Chem. 2]

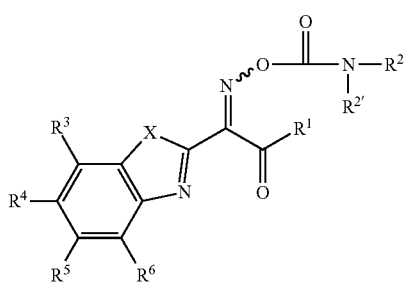

Formula (II)

in Formula (II),
each of $R^3$ to $R^6$ independently represents a hydrogen atom, an alkyl group, an aryl group or a halogen atom, provided that, $R^3$ and $R^4$, $R^4$ and $R^5$, or $R^5$ and $R^6$ may be bound with each other to form an alicyclic or aromatic ring,
X represents —O— or —S—,
$R^1$, $R^2$ and $R^{2'}$ are the same as $R^1$, $R^2$ and $R^{2'}$ in Formula (I) above, respectively, $R^2$ and $R^{2'}$ may be bound to each other to form a nitrogen-containing heterocyclic group.
[4] A photocurable composition containing the photosensitive composition claimed in any one of [1] to [3], wherein the photosensitive composition further contains a base-reactive compound.
[5] The photocurable composition as described in [4], wherein the base-reactive compound is an epoxy resin.
[6] The photocurable composition as described in [4], wherein the base-reactive compound is a polyamic acid.
[7] A chemical amplification resist composition containing the photosensitive composition described in any one of [1] to [3],
wherein the photosensitive composition further contains a compound capable of generating an acid upon irradiation with an actinic ray or radiation.
[8] The chemical amplification resist composition as described in [7], containing a resin (E) having a repeating unit represented by the Formula (1):

[Chem. 3]

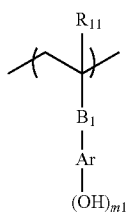

(1)

in Formula (1),
$R_{11}$ represents a hydrogen atom, a methyl group which may have a substituent, or a halogen atom,
$B_1$ represents a single bond or a divalent organic group,
Ar represents an aromatic ring group, and
m1 represents an integer of 1 or more.
[9] The chemical amplification resist composition as described in [7] or [8], which is used for exposure of electron beam or extreme-ultraviolet rays.

[10] A resist film formed using the chemical amplification resist composition described in any one of [7] to [9].
[11] A pattern forming method comprising:
exposing the resist film described in [10]; and
developing the exposed resist film.
[12] A method of manufacturing an electronic device, comprising the pattern forming method described in [11].
[13] An electronic device manufactured by the method described in [12].

Advantage of the Invention

According to the present invention, there is provided a photosensitive composition which contains a compound having a specific structure and thus efficiently generates a base. Particularly, when the photosensitive composition is used as a photocurable composition, the sensitivity, reaction contrast and developability are excellent, and the residual film ratio, solvent resistance and thermal stability of a formed cured film are excellent, and when the photosensitive composition is used as a resist composition, the resolution, and LER performance, and the shape and scum performance of a formed pattern are excellent.

MODE FOR CARRYING OUT THE INVENTION

Hereinafter, exemplary embodiments of the present invention will be described in detail.
In the present specification, when a group (atomic group) is denoted without specifying substitution or unsubstitution, the group may not include a substituent or include a substituent. For example, an "alkyl group" may include not only an alkyl group not having a substituent (unsubstituted alkyl group), but also an alkyl group having a substituent (substituted alkyl group).
In the present invention, the light includes not only extreme-ultraviolet rays (EUV light) but also electron beam.
Also, in the present specification, unless otherwise specifically indicated, "exposure" includes not only the exposure to extreme-ultraviolet rays (EUV light) but also drawing performed by electron beam.
In the present specification, "actinic ray" or "radiation" indicates, for example, a bright line spectrum of a mercury lamp, a far-ultraviolet ray represented by excimer laser, an extreme-ultraviolet ray (EUV light), an X-ray, or an electron beam. Also, in the present invention, the light means an actinic ray or radiation. Also, in the present specification, unless otherwise specifically indicated, "exposure" includes not only the exposure to a mercury lamp, a far-ultraviolet ray represented by excimer laser, an X-ray, or EUV light, but also drawing performed by a corpuscular beam such as an electron beam and an ion beam.
The photosensitive composition of the present invention contains a compound represented by Formula (I) below.

[Chem. 4]

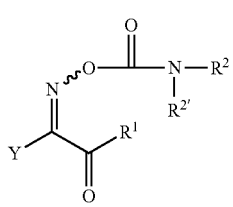

Formula (I)

In Formula (I), Y represents a monovalent organic group.
$R^1$ represents a monovalent organic group.
Each of $R^2$ and $R^{2'}$ independently represents a hydrogen atom, an alkyl group, a cycloalkyl group, an aryl group, or a heteroaryl group. $R^2$ and $R^{2'}$ may be bound with each other to form a nitrogen-containing heterocyclic group.

The wavy line in Formula (I) above indicates that the compound represented by Formula (I) above may be in either a cis- or a trans-form.

The photosensitive composition is not particularly limited as long as it contains the compound represented by Formula (I), but a photocurable composition containing a base-reactive compound and a chemical amplification resist composition containing a compound capable of generating an acid upon irradiation with an actinic ray or radiation may be representatively exemplified.

The present invention provides a photosensitive composition, in which when particularly, the photosensitive composition is used as a photocurable composition, the sensitivity, reaction contrast and developability are excellent, and the residual film ratio, solvent resistance and thermal stability of a formed cured film are excellent, and when the photosensitive composition is used as a resist composition, the resolution, and LER performance, and the shape and scum performance of a formed pattern are excellent. The reason thereof is not clear, but may be assumed as follows.

The photosensitive composition of the present invention contains the compound represented by Formula (I) above. Here, the compound represented by Formula (I) above is a photobase generator that generates a base at exposure with a high efficiency. As a result, when the photosensitive composition of the present invention is used as a photocurable composition, a base is generated even with a small exposure amount, thereby improving the sensitivity and reaction contrast of the photocurable composition. Accordingly, it is thought that the curing reaction of the photocurable composition may be easily promoted by exposure, thereby resulting in improvement of the developability of the photocurable composition, and the solvent resistance of a formed film. Also, it is thought that as a result of the reaction contrast improvement, a contrast in pattern formation during development is also improved, so that a scum performance may become good.

Also, it is thought that the compound represented by Formula (I) above contained in the photocurable composition of the present invention has a structure in which a carbon dioxide gas is not generated as a by-product by exposure, and thus, a film strength of a formed film is improved, thereby obtaining a film excellent in a residual film ratio.

Further, it is thought that since the compound represented by Formula (I) above contained in the photosensitive composition of the present invention is a nonionic compound, when the photosensitive composition of the present invention is used as a resist composition, the compound represented by Formula (1) above is uniformly distributed in a resist film, thereby improving an LER performance.

Also, as described above, the compound represented by Formula (I) above has a high base generation efficiency. Thus, even on a portion of a substrate surface where an acid is excessively generated by scattering light on the substrate surface at exposure, the compound represented by Formula (I) above on the substrate surface generates a large amount of base as compared to other portions, thereby effectively quenching the excessively generated acid described above. As a result, it is thought that an acid is suppressed from excessively diffused in an unexposed portion, and thus the reaction amount of a resin may be uniform in the thickness direction of the resist film, thereby improving the resolution, and the shape of the formed pattern.

The photosensitive composition of the present invention is preferably used as a photocurable composition or a chemical amplification resist composition.

An alkyl group of $R^2$ and $R^{2'}$ may be a linear or branched alkyl group, and specifically, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a 2-ethylhexyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a norbomyl group, a bornyl group (bomane-χ-yl group), an adamantyl group, and a menthyl group (mentha-χ-yl group) may be exemplified. Among them, a tert-butyl group is more preferred.

As for a cycloalkyl group of $R^2$ and $R^{2'}$, a cyclobutyl group, a cyclopentyl group, a cyclohexyl group, a cycloheptyl group, a cyclooctyl group, a cyclononyl group, and a cyclodecyl group may be exemplified, and among them, a cycloalkyl group having 1 to 10 carbon atoms is more preferred.

As for an aryl group of $R^2$ and $R^{2'}$, an aryl group having 6 to 30 carbon atoms is preferred, and specifically, for example, a phenyl group, a 1-naphthyl group, and a 2-naphthyl group may be exemplified.

As for a heteroaryl group of $R^2$ and $R^{2'}$, a group having 4 to 30 carbon atoms is preferred, and as for a hetero ring included in the heteroaryl group of $R^2$ and $R^{2'}$, hetero rings such as a pyridine ring, a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring may be exemplified.

As for the nitrogen-containing heterocyclic group which may be formed when $R^2$ and $R^{2'}$ are bound to each other, a nitrogen-containing heterocyclic group having 6 to 30 carbon atoms is preferred, for example, a 2-pyridyl group, a 3-pyridyl group, a 4-pyridyl group, a 2-pyrrolyl group, a 3-pyrrolyl group, a piperidino group, a 4-piperidyl group, a 2-quinolyl group, a 3-quinolyl group, a 4-quinolyl group, a 1-pyrrolidyl group, a morpholino group, a morpholinyl group, an oxazole group, an isoxazole group, a thiazole group, an isothiazole group, a furanyl group, an imidazole group, a pyrazole group, a pyrazinyl group, a pyrimidinyl group, and a pyridazinyl group may be exemplified.

As for $R^2$ and $R^{2'}$, a hydrogen, an isopropyl group, an isobutyl group, a t-butyl group, a cyclohexyl group, a morpholino group, a 2-pyridyl group, a 3-pyridyl group and a 4-pyridyl group, and a phenyl group are preferred.

As for the monovalent organic group of $R^1$ and Y, for example, an alkyl group, a cycloalkyl group, an alkenyl group, an aryl group, a heterocyclic group and an alkoxycarbonyl group may be exemplified.

These groups may have a substituent, and as for the substituent, an alkyl group, a cycloalkyl group, an alkoxy group, an alkoxycarbonyl group, a carboxyl group, a halogen atom, a hydroxyl group, and a cyano group may be exemplified.

The alkyl group represented by $R^1$ and Y may be linear or branched. The number of carbon atoms in the alkyl group may preferably range from 1 to 50, more preferably from 1 to 30, and further preferably from 1 to 20. As for such an alkyl group, for example, a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group and a 2-ethylhexyl group may be exemplified.

The cycloalkyl group represented by $R^1$ and Y may be monocyclic or polycyclic. As for the cycloalkyl group, preferably, a monocyclic cycloalkyl group having 3 to 8 carbon atoms, such as a cyclopropyl group, a cyclopentyl group, and cyclohexyl group, may be exemplified.

The alkenyl group represented by $R^1$ and Y may be linear or branched. The number of carbon atoms in the alkenyl group preferably ranges from 2 to 50, more preferably from 2 to 30, and still more preferably from 3 to 20. As for such an alkenyl group, for example, a vinyl group, an allyl group and a styryl group may be exemplified.

The aryl group represented by $R^1$ and X preferably has 6 to 14 carbon atoms. As for such a group, for example, a phenyl group and a naphthyl group may be exemplified.

The heterocyclic group represented by $R^1$ and Y preferably has 5 to 20 carbon atoms, and more preferably 6 to 15 carbon atoms. The heterocyclic group may or may not have aromaticity. It is preferable that the heterocyclic group has aromaticity.

A heterocyclic ring contained in the above described groups may be monocyclic or polycyclic. As for such a heterocyclic ring, for example, an imidazole ring, a pyridine ring, a pyrazine ring, a pyrimidine ring, a pyridazine ring, a 2H-pyrrole ring, a 3H-indole ring, a 1H-indazole, a purine ring, an isoquinoline ring, a 4H-quinolizine ring, a quinoline ring, a phthalazine ring, a naphthyridine ring, a quinoxaline ring, a quinazoline ring, a cinnoline ring, a pteridine ring, a phenanthridine ring, an acridine ring, a phenanthroline ring, a phenazine ring, a perimidine ring, a triazine ring, a benzyisoquinoline ring, a thiazole ring, a thiadiazine ring, an azepine ring, an azocine ring, an isothiazole ring, an isoxazole ring, and a benzothiazole ring may be exemplified.

In the alkoxycarbonyl group represented by $R^1$ and Y, the alkyl group is the same as the above described alkyl group represented by $R^1$ and Y, and also its preferred range is also the same.

The alkyl group, the cycloalkyl group, the alkenyl group, the aryl group, the heterocyclic group, and the alkoxycarbonyl group represented by $R^1$ may have a substituent. As for the substituent, for example, a halogen atom (a fluorine atom, a chloro atom, a bromine atom, an iodine atom), a linear, branched or cyclic alkyl group (e.g., a methyl group, an ethyl group, and a propyl group), an alkenyl group, an alkynyl group, an aryl group, an acyl group, an alkoxycarbonyl group, an aryloxycarbonyl group, a carbamoyl group, a cyano group, a carboxyl group, a hydroxyl group, an alkoxy group, an aryloxy group, an alkylthio group, an arylthio group, a heterocyclic oxy group, an acyloxy group, an amino group, a nitro group, a hydrazino group, and a heterocyclic group may be exemplified. Also, it may be further substituted by these groups. A halogen atom, and a methyl group are preferred.

As for $R^1$, an alkyl group, a cycloalkyl group, and an aryl group are preferred, and a cycloalkyl group, and an alkyl group are more preferred.

Y preferably represents a heterocyclic group, and more preferably represents a group represented by Formula (i).

[Chem. 5]

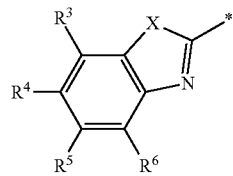

Formula (i)

Each of $R^3$ to $R^6$ independently represents a hydrogen atom, an alkyl group, an aryl group or a halogen atom. Meanwhile, $R^3$ and $R^4$, $R^4$ and $R^5$, or $R^5$ and $R^6$ may be bound with each other to form an alicyclic or aromatic ring. X represents —O— or —S—. * represents a bond.

A preferred range of the alkyl group represented by $R^3$ to $R^6$ is the same as that of the alkyl group represented by $R^2$. Also, a preferred range of the aryl group represented by $R^3$ to $R^6$ is the same as that of the aryl group represented by $R^1$.

As for the halogen atom represented by $R^3$ to $R^6$, a fluorine atom, a chloro atom, a bromine atom, and an iodine atom may be exemplified.

As for the alicyclic or aromatic ring which may be formed when $R^3$ and $R^4$, $R^4$ and $R^5$, or $R^5$ and $R^6$ among $R^3$ to $R^6$ are bound to each other, an aromatic ring is preferred, and a benzene ring is more preferred.

Preferably, each of $R^3$ to $R^6$ independently represents a hydrogen atom, an alkyl group or a halogen atom, or $R^3$ and $R^4$, $R^4$ and $R^5$, or $R^5$ and $R^6$ are bound to each other to constitute a benzene ring. More preferably, each of $R^3$ to $R^6$ independently represents a hydrogen atom, a methyl group, a fluorine atom, a chloro atom or a bromine atom, or $R^3$ and $R^4$, $R^4$ and $R^5$, or $R^5$ and $R^6$ are bound to each other to form a benzene ring.

Preferred aspects of $R^3$ to $R^6$ are as follows.

(Aspect 1) At least two are hydrogen atoms.

(Aspect 2) The number of an alkyl group, an aryl group or a halogen atom is three or less in total, and preferably one or less.

(Aspect 3) $R^3$ and $R^4$, $R^4$ and $R^5$, or $R^5$ and $R^6$ are bound to each other to form a benzene ring.

(Aspect 4) An aspect satisfying the aspects 1 and 2 and/or an aspect satisfying the aspects 1 and 3.

X represents —O— or —S—.

As described above, it is preferred that the compound represented by Formula (I) is a compound represented by Formula (II) below. Since the compound represented by Formula (I) is the compound represented by Formula (II) below, the temporal stability of the photosensitive composition is improved.

[Chem. 6]

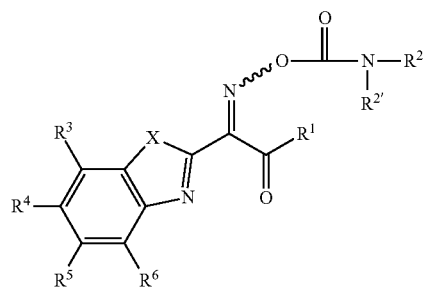

Formula (II)

In Formula (II), $R^3$ to $R^6$ and X are the same as $R^3$ to $R^6$ in Formula (i) above.

$R^1$, $R^2$ and $R^{2'}$ are the same as $R^1$, $R^2$ and $R^{2'}$ in Formula (I) above, respectively. $R^2$ and $R^{2'}$ may be bound to each other to form a nitrogen-containing heterocyclic group.

The wavy line in Formula (II) above indicates that the compound represented by Formula (II) above may be in either a cis- or a trans-form.

In Formula (II), specific examples and preferred ranges of $R^3$ to $R^6$, and X are the same as those described in Formula (i), and specific examples and preferred ranges of $R^1$, $R^2$ and $R^{2'}$ are the same as those described in Formula (I).

In Formula (II), specific examples and preferred ranges of the nitrogen-containing heterocyclic group which may be formed when $R^2$ and $R^{2'}$ are bound to each other are the same as those described in Formula (I).

In the photosensitive composition of the present invention, a compound (B) represented by Formula (I) is preferably used in a range of 0.1 parts to 10 parts by mass, and more preferably in a range of 0.5 parts to 5 parts by mass based on 100 parts by mass of the total content of the photosensitive composition (preferably, the total solid content, more preferably the total polymer content). Two or more kinds may be used in combination. If a cis- or a trans-form is present in the compound represented by Formula (I), only one is representatively described below, but a tautomer thereof may be used.

[Chem. 7]

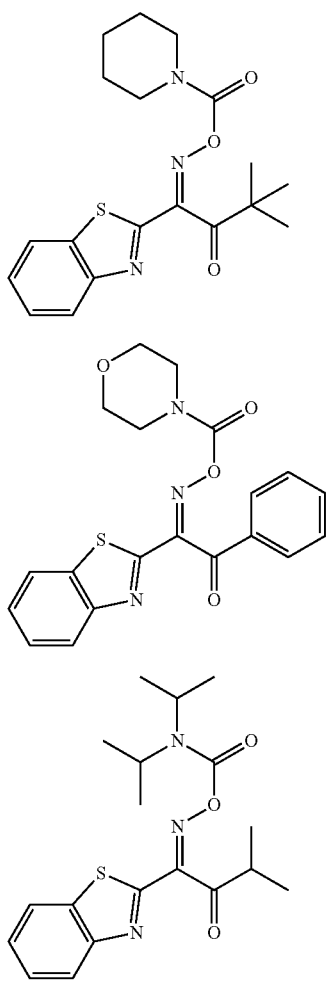

B-1

B-2

B-3

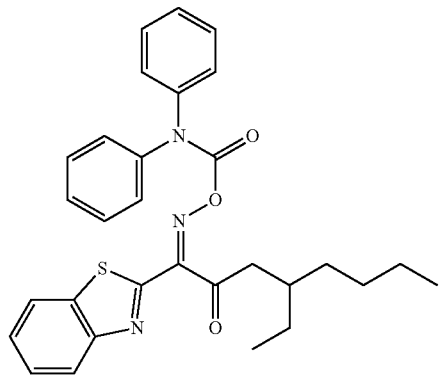

B-4

B-5

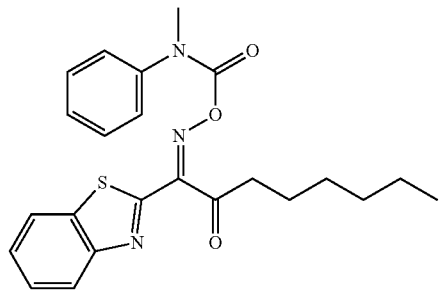

B-6

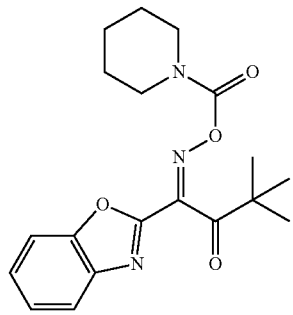

B-7

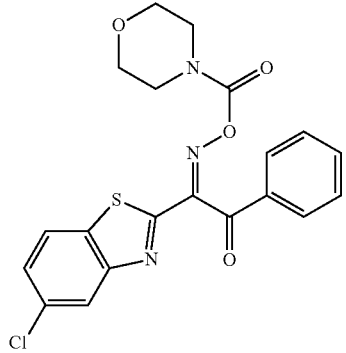

B-8
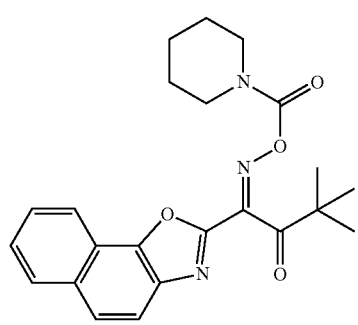
B-9
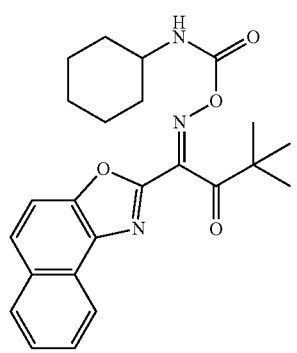
B-10
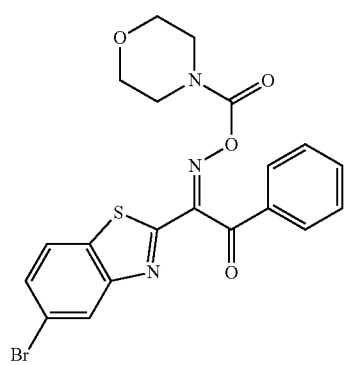
B-11
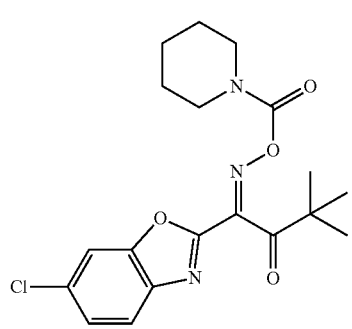
B-12
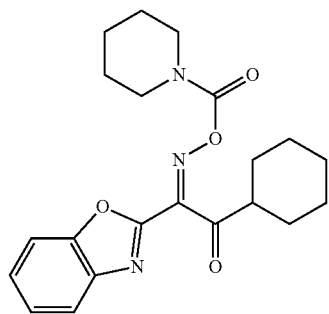
B-13
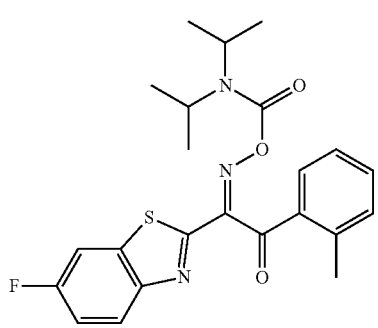
B-14
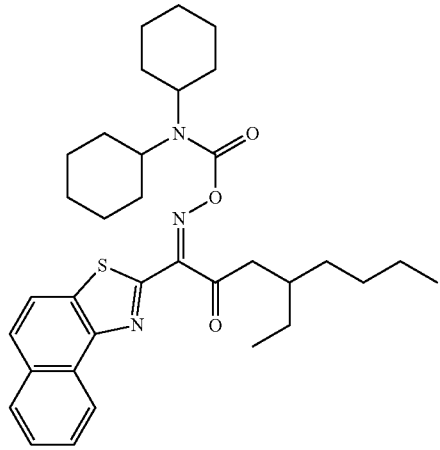
B-15
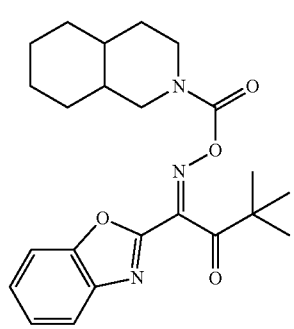

[Chem. 8]
B-16
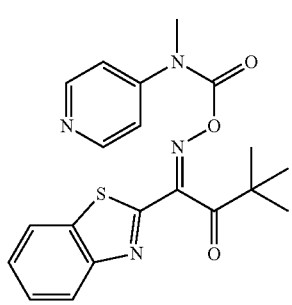
B-17
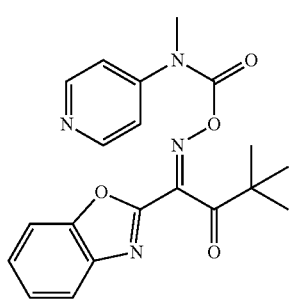
B-18
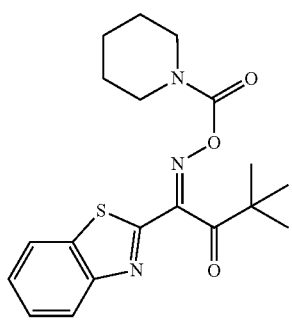
B-19
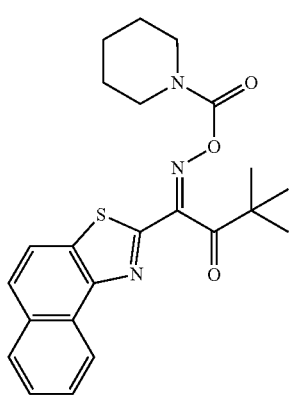
B-20
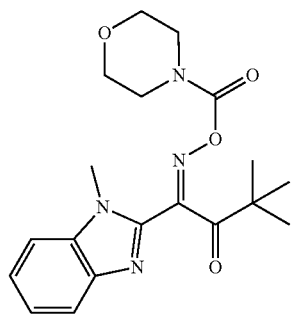
B-21
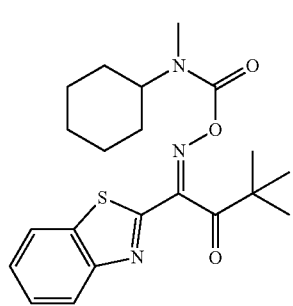
B-22
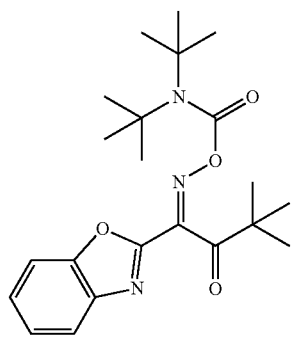
B-23
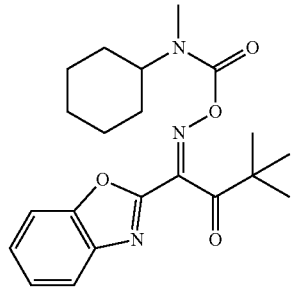
B-24
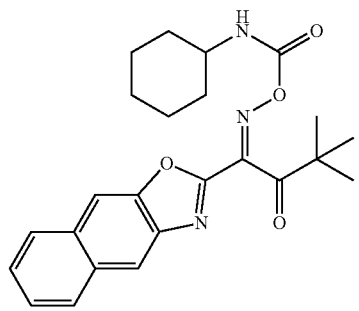

B-25 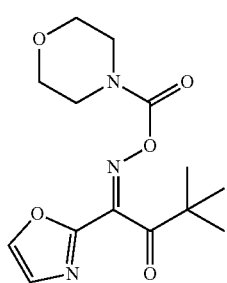

B-26 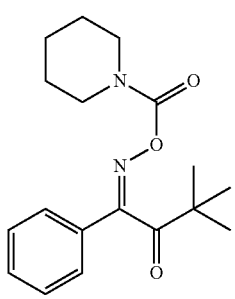

B-27 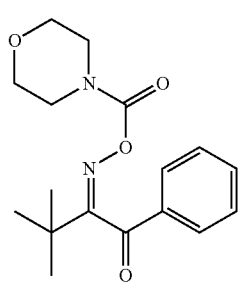

B-28 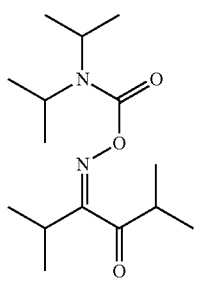

B-29 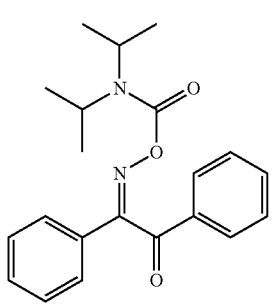

B-30 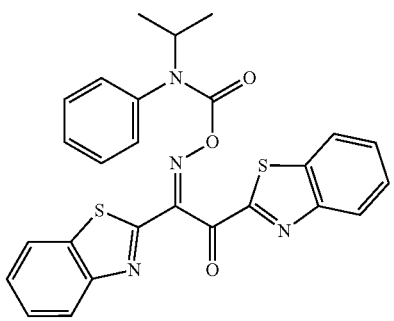

B-31 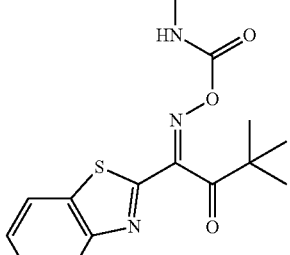

B-32 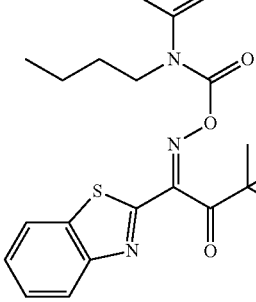

B-33 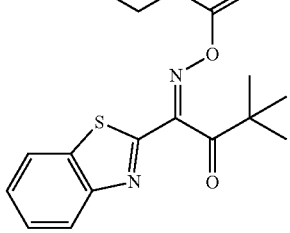

In the present invention, in a method of preparing the compound represented by Formula (I), the compound may be easily synthesized through a reaction using a corresponding oxime compound and aminocarbonyl halide, or isocyanate, in the presence of a base (e.g., triethylamine, pyridine), in an inert solvent such as THF, DMF, acetonitrile, or a basic solvent (e.g., pyridine), or in the presence of a catalyst (a tin-based compound, or a bismuth-based compound), in inert solvent such as THF, DMF, acetonitrile. The reaction temperature preferably ranges from −10° C. to 60° C.

Further, as for the amino carbonyl halide, for example, alkylaminocarbonyl halide, or aryl amino carbonyl halide may be used to synthesize various corresponding oxime sulfonate compounds. Also, as for the isocyanate, for example, alkylisocyanate, or arylisocyanate may be used to synthesize various corresponding oxime sulfonate compounds.

In the method of synthesizing the oxime compound, various methods described in standard chemistry textbooks (e.g., J. March, Advanced Organic Chemistry, 4th Edition, Wiley Interscience, 1992), or specialized monographs, for example, S. R. Sandler & W. Karo, Organicfunctional group preparations, Vol. 3, Academic Press, may be employed.

As for a particularly preferred method of synthesizing the oxime compound, for example, a method of reacting aldehyde, ketone, hydroxylamine, or a salt thereof in a polar solvent such as ethanol or aqueous ethanol may be exemplified. In this case, a base such as sodium acetate or pyridine may be added to control pH of a reaction mixture. It has conventionally known that the reaction rate is dependent on pH, and the base may be added at the start or continuously added during the reaction.

Also, a basic solvent such as pyridine may be used as at least any one of a base, a solvent, and a co-solvent.

Furthermore, preferably, the reaction temperature is generally the reflux temperature of the mixture, i.e., about 60° C. to 120° C.

As for another preferred method of synthesizing the oxime compound, a method thorough nitrosation of an "active" methylene group with nitrous acid or alkyl nitrite may be exemplified. For example, both the alkaline conditions as described in Organic Syntheses coll. Vol. VI (J. Wiley & Sons, New York, 1988), pp. 199 and 840, and the acidic conditions as described in Organic Synthesis coll. Vol. V, pp. 32 and 373, coll. Vol. III, pp. 191 and 513, coll. Vol. II, pp. 202, 204 and 363 are proper in the synthesis of the oxime compound used as a starting material in the present invention.

The nitrous acid is generally generated from sodium nitrite.

As for the alkyl nitrite, for example, methyl nitrite, ethyl nitrite, isopropyl nitrite, butyl nitrite, and isoamyl nitrite may be exemplified.

Hereinafter, descriptions will be made in detail on components other than the compound represented by Formula (I) above, which may be contained in the photosensitive composition of the present invention (hereinafter, which may be simply referred to as "photocurable composition of the present invention") when the photosensitive composition of the present invention is particularly used as, for example, a photocurable composition.

Meanwhile, specific examples, preferred ranges, and content ranges of the compound represented by Formula (I) above contained in the photocurable composition are the same as those described above.

[A] Base-Reactive Compound

The photocurable composition of the present invention preferably contains a base-reactive compound.

The base-reactive compound is a compound which causes a curing reaction by a base generated by the compound represented by Formula (I) above. The base-reactive compound is not particularly limited as long as it is a compound which causes a curing reaction by a base generated by the compound represented by Formula (I) above, but, a compound having an epoxy group or a polyamic acid is preferred.

The content of the base-reactive compound based on the total solid content of the photocurable composition of the present invention preferably ranges from 0.1% to 20% by mass, and more preferably from 0.5% to 15% by mass.

[A-1] Compound Having an Epoxy Group

A compound having an epoxy group refers to a compound having one or more epoxy groups in one molecule, and conventionally known compounds may be used. In the photocurable composition of the present invention, the compound having an epoxy group serves as a base-reactive compound. That is, according to the photocurable composition of the present invention, a base occurs from the base-reactive compound at an exposed portion, and thus the compound having an epoxy group is partially denatured (becomes insoluble in a developer). Meanwhile, in the present invention, an epoxy group has a cyclic ether structure. As for a representative cyclic ether structure, a three-membered ring (oxiranyl group), and a four-membered ring (oxetanyl group) may be exemplified.

As for the compound having one epoxy group in the molecule, glycidyl (meth) acrylate, glycidyl α-ethyl acrylate, glycidyl-α-n-propylacrylate, glycidyl-α-n-butylacrylate, 3,4-epoxybutyl methacrylate, 3,4-epoxybutyl α-ethylacrylate, 6,7-epoxyheptyl methacrylate, 6,7-epoxyheptyl α-ethylacrylate, o-vinylbenzyl glycidyl ether, m-vinylbenzyl glycidyl ether, p-vinylbenzyl glycidyl ether, 3-methyl-3-(meth) acryloyloxy-methyl oxetane, 3-ethyl-3-(meth) acryloyloxy-methyl oxetane, phenyl glycidyl ether, γ-glycidoxypropyltrimethoxysilane, β-(3,4-epoxycyclohexyl) ethyl trimethoxy silane, and γ-glycidoxypropyl diethoxy silane may be exemplified.

As for the compound having two or more epoxy groups in the molecule, bisphenol type diglycidyl ethers such as bisphenol A diglycidyl ether, bisphenol F diglycidyl ether, bisphenol S diglycidyl ether, hydrogenated bisphenol A diglycidyl ether, hydrogenated bisphenol F diglycidyl ether, and hydrogenated bisphenol AD diglycidyl ether; polyglycidyl ethers of polyhydric alcohols such as 1,4-butanediol diglycidyl ether, 1,6-hexanediol diglycidyl ether, glycerin triglycidyl ether, trimethylolpropane triglycidyl ether, polyethylene glycol diglycidyl ether, and polypropylene glycol diglycidyl ether; polyglycidyl ethers of polyether polyols obtained by adding one or more kinds of alkylene oxides to aliphatic polyhydric alcohol such as ethylene glycol, propylene glycol, glycerin; phenol novolak type epoxy resins; cresol novolak type epoxy resin; polyphenol type epoxy resins; diglycidyl esters of aliphatic long chain dibasic acids; glycidyl esters of higher fatty acids; aliphatic polyglycidyl ethers; epoxidized soybean oil; and epoxidized linseed oil may be exemplified.

The compound having an epoxy group is preferably an epoxy resin (referring to a compound in the form of resin among the above described compounds having an epoxy group), and among them, a phenol novolak type epoxy resin, a cresol novolak type epoxy resin or a polyphenol type epoxy resin is preferred, and a phenol novolak type epoxy resin is more preferred.

As for commercially available products of the compound having two or more epoxy groups in the molecule, for example, bisphenol A type epoxy resins such as EPIKOTE 1001, 1002, 1003, 1004, 1007, 1009, 1010, 828 (manufactured by Japan Epoxy Resins Co., Ltd.); bisphenol F type epoxy resins such as EPIKOTE 807 (manufactured by Japan Epoxy Resins Co., Ltd.); phenol novolak type epoxy resins such as EPIKOTE 152, 154, 157S65 (manufactured by Japan Epoxy Resins Co., Ltd.), EPPN201, 202 (manufactured by Nippon Kayaku Co., Ltd.); cresol novolak type epoxy resins such as EOCN102, 103S, 104S, 1020, 1025, 1027 (manufactured by Nippon Kayaku Co., Ltd.), EPIKOTE 180S75 (manufactured by Japan Epoxy Resins Co., Ltd.); polyphenol type epoxy resins such as EPIKOTE 1032H60, XY-4000 (manufactured by Japan Epoxy Resins Co., Ltd.); cycloaliphatic epoxy resins such as CY-175, 177, 179, Araldite CY-182, 192, 184 (manufactured by Ciba Specialty Chemicals Corporation), ERL-4234, 4299, 4221, 4206 (manufactured by U.C.C corp.), Showdyne 509 (manufactured by Showa Denko K.K.), EPICLON 200, 400 (manufactured by DIC Corporation), EPIKOTE 871, 872 (manufactured by Japan Epoxy Resins Co., Ltd.), ED-5661, 5662 (manufactured by Celanese Coating Co., Ltd.); and aliphatic polyglycidyl ethers such as EPOLIGHT 100MF (manufactured by KYOEISHA CHEMICAL CO., LTD.), EPIOL TMP (manufactured by NOF Corporation) may be exemplified.

The content of the compound having an epoxy group in the photocurable composition of the present invention is not particularly limited, but preferably ranges from 10 parts by mass to 200 parts by mass and more preferably from 20 parts by mass to 150 parts by mass based on 1 parts by mass of the compound represented by Formula (I). In view of obtaining a radiation-sensitive composition which is excellent in the radiation sensitivity and also allows an obtained cured film thereof to have an excellent solvent resistance.

[A-2] Polyamic Acid

The polyamic acid which may be contained in the photocurable composition of the present invention serves as a base-reactive compound. That is, according to the photocurable composition of the present invention, a base occurs from the base-reactive compound in an exposed portion, and becomes a catalyst to promote a ring closure reaction of polyamic acid to polyimide.

The polyamic acid may be obtained by, for example, diamine and tetracarboxylic acid dianhydride as raw materials. As for diamine, specifically, for example, polytetramethylene oxide-di-o-aminobenzoate, polytetramethylene oxide-di-m-aminobenzoate, polytetramethylene oxide-di-p-aminobenzoate, polytrimethylene oxide-di-o-aminobenzoate, polytrimethylene oxide-di-m-aminobenzoate, polytrimethylene oxide-di-p-amino benzoate, 3,3'-diaminodiphenyl ether, 3,4'-diaminodiphenyl ether, 4,4'-diaminodiphenyl ether, 1,3-bis (3-aminophenoxy) benzene, 1,4-bis(4-aminophenoxy) benzene, 1,3-bis(4-aminophenoxy) benzene, 3,3'-diaminodiphenyl sulfone, 4,4'-diamino diphenyl sulfone, 1,3-bis (4-aminophenoxy) propane, 1,4-bis(4-aminophenoxy) butane, 1,5-bis(4-aminophenoxy) pentane heptane, o-phenylenediamine, m-phenylenediamine, p-phenylenediamine, 3,3'-diaminodiphenylmethane, 3,4'-diaminodiphenylmethane, 4,4'-diaminodiphenylmethane, 3,3'-diaminodiphenyl-difluoro methane, 4,4'-diaminodiphenyl-difluoro methane, 3,3'-diaminodiphenyl sulfide, 3,4'-diaminodiphenyl sulfide, 4,4'-diaminodiphenyl sulfide, 3,3'-diaminodiphenyl ketone, 3,4'-diaminodiphenyl ketone, 4,4'-diaminodiphenyl ketone, 2,2-bis(3-aminophenyl) propane, 2,2-bis(3,4'-diaminodiphenyl) propane, 2,2-bis(4-aminophenyl) propane, 2,2-bis(3-aminophenyl) hexafluoropropane, 2,2-bis(3,4'-diaminodiphenyl) hexafluoropropane, 2,2-bis(4-aminophenyl) hexafluoropropane, 3,3'-[1,4-phenylene bis (1-methyl-ethylidene)]bisaniline, 3,4'-[1,4-phenylene bis(1-methyl-ethylidene)]bisaniline, 4,4'-[1,4-phenylene bis(1-methyl-ethylidene)]bisaniline, 2,2-bis[4-(3-aminophenoxyl) phenyl]propane, 2,2-bis[4-(4-aminophenoxyl)phenyl] propane, 2,2-bis[4-(3-aminophenoxyl)phenyl] hexafluoropropane, 2,2-bis[4-(4-aminophenoxyl)phenyl] hexafluoropropane, bis[4-(3-aminophenoxyl)phenyl]sulfide, bis[4-(4-aminophenoxyl) phenyl]sulfide, bis[4-(3-aminophenoxyl)phenyl]sulfone, bis[4-(4-aminophenoxyl)phenyl] sulfone, 1,2-diaminoethane, 1,3-diaminopropane, 1,4-diaminobutane, 1,5-aminopentane, 1,6-diaminohexane, 1,7-diamino heptane, 1,8-aminooctane, 1,9-diaminononane, 1,10 diaminodecane, 1,11-diamino undecane, 3,3'-dicarboxy-4,4'-diaminodiphenylmethane, 3,5-diamino benzoic acid, 1,2-diamino-4-hydroxy-benzene, 1,3-diamino-5-hydroxy-benzene, 1,3-diamino-4-hydroxy benzene, 1,4-diamino-6-hydroxy benzene, 1,5-diamino-6-hydroxy benzene, 1,3-diamino-4,6-dihydroxybenzene, 1,2-diamino-3,5-dihydroxybenzene, 4(3,5-diaminophenoxy) phenol, 3-(3,5-diaminophenoxy) phenol, 2-(3,5-diaminophenoxyl) phenol, 3,3'-dihydroxy-4,4'-diamino biphenyl, 3,3'-diamino-4,4'-dihydroxybiphenyl, 2,2-bis (4-hydroxy-3-aminophenyl) propane, 2,2-bis (4-hydroxy-3-aminophenyl) hexafluoropropane, bis (4-hydroxy-3-aminophenyl) ketone, 2,2-bis(4-hydroxy-3-aminophenyl) sulfide, 2,2-bis(4-hydroxy-3-aminophenyl) ether, 2,2-bis(4-hydroxy-3-aminophenyl) sulfone, 2,2-bis(4-hydroxy-3-aminophenyl) methane, 4-[(2,4-diamino-5-pyrimidinyl)methyl]phenol, p-(3,6-diamino-s-triazin-2-yl) phenol, 2,2-bis(4-hydroxy-3-aminophenyl) difluoromethane, 2,2-bis(4-amino-3-hydroxyphenyl) propane, 2,2-bis(4-amino-3-hydroxyphenyl) hexafluoropropane, bis (4-amino-3-hydroxyphenyl)ketone, 2,2-bis(4-amino-3-hydroxyphenyl) sulfide, 2,2-bis(4-amino-3-hydroxyphenyl) ether, 2,2-bis(4-amino-3-hydroxyphenyl) sulfone, 2,2-bis(4-amino-3-hydroxyphenyl) methane, 2,2-bis(4-amino-3-hydroxyphenyl) difluoromethane, α,ω-bis(2-aminoethyl) polydimethylsiloxane, α,ω-bis(3-aminopropyl) polydimethylsiloxane, α,ω-bis(4-aminobutyl) polydimethylsiloxane, α,ω-bis(4-aminophenyl) polydimethylsiloxane, and α,ω-bis(3-aminopropyl) polydiphenylsiloxane may be exemplified. These diamine components may be used either individually or in combination of two or more kinds thereof.

As for the tetracarboxylic acid dianhydride, specifically, for example, ethylene glycol-bis-trimellitic anhydride ester, 1,3-propanediol-bis-trimellitic anhydride ester, butanediol-bis-trimellitic anhydride ester, pentanediol-bis-trimellitic anhydride ester, heptanediol-bis-trimellitic anhydride ester, and decanediol-bis-trimellitic anhydride ester may be exemplified. These may be used either individually or as a mixture of two or more kinds thereof. Preferably, ethylene glycol-bis-trimellitic anhydride ester, pentanediol-bis-trimellitic anhydride ester, and decanediol-bis-trimellitic anhydride ester may be exemplified.

More preferably, a combination of ethylene glycol-bis-trimellitic anhydride ester and pentanediol-bis-trimellitic anhydride ester, a combination of ethylene glycol-bis-trimellitic anhydride ester and decanediol-bis-trimellitic anhydride ester, oxydiphthalic dianhydride, pyromellitic dianhydride, 3,3',4,4'-biphenyltetracarboxylic acid dianhydride, 2,2',3,3'-biphenyltetracarboxylic acid dianhydride, 2,3,3',4'-biphenyltetracarboxylic acid dianhydride, 2,2-bis(3,4-dicarboxyphenyl) propane dianhydride, 2,2-bis(2,3-dicarboxyphenyl) propane dianhydride, 1,1-bis(2,3-dicarboxyphenyl) ethane dianhydride, 1,1-bis(3,4-dicarboxyphenyl) ethane dianhydride, bis(2,3-dicarboxyphenyl) methane dianhydride, bis(3,4-dicarboxyphenyl) methane dianhydride, bis(3,4-dicarboxyphenyl) sulfone dianhydride, 3,4,9,10-perylene tetracarboxylic acid dianhydride, bis(3,4-dicarboxyphenyl) ether dianhydride, benzene-1,2,3,4-tetracarboxylic acid dianhydride, 3,3',4,4'-benzophenonetetracarboxylic acid dianhydride, 2,2',3,3'-benzophenone tetracarboxylic acid dianhydride, 2,3,3',4'-benzophenonetetracarboxylic acid dianhydride, 1,2,5,6-naphthalene tetracarboxylic acid dianhydride, 2,3,6,7-naphthalene tetracarboxylic acid dianhydride, 1,2,4,5-naphthalene tetracarboxylic acid dianhydride, 1,4,5,8-naphthalene tetracarboxylic acid dianhydride, 2,6-dichloronaphthalene-1,4,5,8-tetracarboxylic acid dianhydride, 2,7-dichloronaphthalene-1,4,5,8-tetracarboxylic acid dianhydride, 2,3,6,7-tetrachloro naphthalene-1,4,5,8-tetracarboxylic acid dianhydride, phenanthrene-1,8,9,10-tetracarboxylic acid dianhydride, bis (3,4-dicarboxyphenyl) dimethylsilane dianhydride, bis(3,4-dicarboxyphenyl) methyl phenyl silane dianhydride, bis(3,4-dicarboxyphenyl) diphenyl silane dianhydride, 1,4-bis (3,4-dicarboxyphenyl dimethylsilyl) benzene dianhydride, 1,3-bis(3,4-dicarboxyphenyl)-1,1,3,3-tetramethyl dicyclohexane dianhydride, p-phenylene bis(trimellitic acid monoester acid anhydride), 2,2-bis(3,4-dicarboxyphenyl) hexafluoropropane dianhydride, 2,2-bis[4-(3,4-dicarboxyphenoxyl)phenyl]hexafluoropropane dianhydride, 2,2-bis[4-(3,4-dicarboxyphenoxyl) phenyl]propane dianhydride, 4,4-bis (3,4-dicarboxy phenoxy) diphenyl sulfide dianhydride, 1,5-cyclooctadiene-1,2,5,6-tetracarboxylic acid dianhydride, 5-carboxymethyl-bicyclo[2.2.1]heptane-2,3,6-tricarboxylic acid-2,3:5,6-dianhydride, 1-carboxymethyl-2,3,5-cyclopentane tricarboxylic acid-2,6:3,5-dianhydride, bicyclo[2.2.2]oct-7-ene-2,3,5,6-tetracarboxylic acid dianhydride, 5-(2,5-dioxotetrahydro-3-furanyl)-3-methyl-3-cyclohexene-1,2-dicarboxylic acid anhydride, tetrahydrofuran-2,3,4,5-tetracarboxylic acid dianhydride, 4-(2,5-dioxotetrahydrofuran-3-yl)-1,2,3,4-tetrahydronaphthalene-1,2-dicarboxylic acid anhydride, decahydronaphthalene-1,4,5,8-tetracarboxylic acid dianhydride, 4,8-dimethyl-1,2,3,5,6,7-hexahydronaphthalene-1,2,5,6-tetracarboxylic acid dianhydride, cyclopentane-1,2,3,4-tetracarboxylic acid dianhydride, pyrrolidine-2,3,4,5-tetracarboxylic acid dianhydride, 1,2,3,4-cyclobutane tetracarboxylic acid dianhydride, bis (exo-bicyclo[2.2.1]heptane-2,3-dicarboxylic anhydride) sulfone, ethylene tetracarboxylic acid dianhydride, and 1,2,3,4-butane tetracarboxylic acid dianhydride may be exemplified. These tetracarboxylic acid dianhydride components may be used either individually or in combination of two or more kinds thereof.

The polyamic acid may be synthesized by mixing the diamine with the tetracarboxylic acid dianhydride in any solvent, and a polyamic acid solution may be obtained. In the method of preparing the polyamic acid, any method capable of preparing the polyamic acid such as a conventionally known method may be employed. Particularly, it is preferred that the polyamic acid is synthesized in an organic solvent. As for a solvent used for the synthesis of the polyamic acid, for example, N,N-dimethylformamide, N,N-dimethylacetamide, N-methyl-2-pyrrolidone, γ-butyrolactone, 1,2-dimethoxyethane, tetrahydrofuran, 1,3-dioxane, 1,4-dioxane, dimethyl sulfoxide, benzene, toluene, xylene, mesitylene, phenol, and cresol may be exemplified. These may be used either individually or as a mixture of two or more kinds thereof.

In the mixture in the synthesis of the polyamic acid, the molar ratio of the diamine to the tetracarboxylic acid dianhydride is preferably in the range of 0.8 to 1.2. In this case, a polyamic acid having a large molecular weight and an excellent elongation may be obtained.

The above described molar ratio is more preferably in the range of 0.9 to 1.1.

[B] Solvent

The photocurable composition of the present invention preferably contains a solvent.

As for the solvent which may be contained in the photocurable composition of the present invention, diethylene glycol monoethyl ether acetate, diethylene glycol diethyl ether, diethylene glycol ethyl methyl ether, diethylene glycol dimethyl ether, propylene glycol monomethyl ether, ethylene glycol monobutyl ether acetate, propylene glycol monomethyl ether acetate, dipropylene glycol monomethyl ether acetate, 3-methoxybutyl acetate, cyclohexanol acetate, benzyl alcohol, 3-methoxy butanol, N, N-dimethylformamide, N, N-dimethylacetamide, N-methyl-2-pyrrolidone, γ-butyrolactone, 1,2-dimethoxyethane, tetrahydrofuran, 1,3-dioxane, 1,4-dioxane, dimethyl sulfoxide, benzene, toluene, xylene, mesitylene, phenol, and cresol are preferred.

[C] Alkali-Soluble Resin

When the photocurable composition of the present invention particularly contains a compound having an epoxy group, the photocurable composition of the present invention may contain an alkali-soluble resin so that the alkali-soluble resin shows a solubility in an alkali used in the development process, and as a result, the developability is improved, and thus a cured film having a more precise pattern may be formed. The alkali-soluble resin is not particularly limited as long as it shows a solubility in an alkali developer used in the development treatment process of the photosensitive composition containing the above described components. As for such an alkali-soluble resin, an alkali-soluble resin having a carboxyl group is preferred, and a copolymer (hereinafter, also referred to as a copolymer "α") of (a1) at least one kind selected from the group consisting of unsaturated carboxylic acids and unsaturated carboxylic acid anhydrides (also referred to as a "compound (a1)"), and (a2) an unsaturated compound other than (a1) (also referred to as a "compound (a2)") is particularly preferred.

Specific examples of the compound (a1) may include monocarboxylic acids such as acrylic acid, methacrylic acid, crotonic acid, 2-acryloyloxyethyl succinate, 2-methacryloyloxyethyl succinate, 2-acryloyloxyethyl hexahydrophthalic acid, 2-methacryloyl oxyethyl hexahydrophthalic acid, dicarboxylic acids such as maleic acid, fumaric acid, citraconic acid, and acid anhydrides of the above dicarboxylic acids.

Among these compounds (a1), from the viewpoint of the copolymerization reactivity or the solubility of the resultant copolymer in an alkali developer, for example, acrylic acid, methacrylic acid, 2-acryloyloxyethyl succinate, 2-methacryloyloxyethyl succinate, and maleic anhydride are preferred.

In the copolymer [α], the compound (a1) may be used alone or as a mixture of two or more kinds thereof. In the copolymer [α], the content of repeating units derived from the compound (a1) preferably ranges from 5% to 60% by mass, more preferably from 7% to 50% by mass, and particularly preferably from 8% to 40% by mass. When the content of the repeating units derived from the compound (a1) ranges from 5% to 60% by mass, a photosensitive composition in which various properties such as sensitivity and developability are balanced at a higher level may be obtained.

Specific examples of the compound (a2) may include: acrylic acid alkyl esters such as methyl acrylate, n-propyl acrylate, i-propyl acrylate, n-butyl acrylate, sec-butyl acrylate, t-butyl acrylate; (meth)acrylic acid alkyl esters, such as methyl methacrylate, ethyl methacrylate, n-propyl methacrylate, i-propyl methacrylate, n-butyl methacrylate, sec-butyl methacrylate, t-butyl methacrylate; acrylic acid alicyclic esters such as cyclohexyl acrylate, 2-methylcyclohexyl acrylate, tricyclo[5.2.1.0$^{2,6}$]decan-8-yl acrylate, 2-(tricyclo [5.2.1.0$^{2,6}$]decan-8-yloxy)ethyl acrylate, and isobornyl acrylate; methacrylic acid alicyclic esters such as cyclohexyl methacrylate, 2-methylcyclohexyl methacrylate, tricyclo [5.2.1.0$^{2,6}$]decan-8-yl methacrylate, 2-(tricyclo[5.2.1.0$^{2,6}$]

decan-8-yloxy)ethyl methacrylate, and isobornyl methacrylate; aryl esters of acrylic acid such as phenyl acrylate and benzyl acrylate, and aralkyl esters thereof; hydroxyalkyl esters of methacylic acid such as 2-hydroxyethylester methacrylate, 3-hydroxypropylester methacrylate; aryl esters of methacrylic acid such as phenyl methacrylate and benzyl methacrylate, and aralkyl esters thereof; unsaturated dicarboxylic acid dialkyl esters such as diethyl maleate, diethyl fumarate; acrylic esters having an oxygen-containing heterocyclic 5- or 6-membered ring such as tetrahydrofuran-2-yl acrylate, tetrahydro pyran-2-yl acrylate, 2-methyltetrahydro pyran-2-yl acrylate; methacrylic esters having an oxygen-containing heterocyclic 5- or 6-membered ring such as tetrahydrofuran-2-yl methacrylate, tetrahydro pyran-2-yl methacrylate, 2-methyltetrahydro pyran-2-yl methacrylate; vinyl aromatic compounds such as styrene, α-methyl styrene, p-methoxystyrene; conjugated diene compounds such as 1,3-butadiene, isoprene; and acrylonitrile, methacrylonitrile, acrylamide, and methacrylamide.

Among these compounds (a2), in view of copolymerization reactivity, n-butyl methacrylate, benzyl methacrylate, tricyclo[5.2.1.0$^{2,6}$]decan-8-yl methacrylate, styrene, p-methoxy styrene, tetrahydrofuran-2-yl methacrylate, 1,3-butadiene, and 2-hydroxyethyl methacrylate ester are preferred.

The copolymer [α] may be prepared by polymerizing monomers of components in the presence of a radical polymerization initiator in a proper solvent. As for a solvent used for such polymerization, for example, diethylene glycolalkyl ether, propylene glycol monoalkyl ether acetate, alkoxypropionic acid alkyl, and acetic ester are preferred. These solvents may be used either individually or as a mixture of two or more kinds thereof.

Also, the radical polymerization initiator is not particularly limited, but for example, azo compounds such as 2,2'-azobisisobutyronitrile, 2,2'-azobis-(2,4-dimethylvaleronitrile), 2,2'-azobis-(4-methoxy-2,4-dimethylvaleronitrile), 4,4'-azobis (4-cyanovaleric acid), and dimethyl-2,2'-azobis (2-methylpropionate) may be exemplified. These radical polymerization initiators may be used either individually or as a mixture of two or more kinds thereof.

A mass-average molecular weight (hereinafter, referred to as "Mw") of the copolymer [α], in terms of polystyrene (through gel permeation chromatography (GPC)), preferably ranges from 2,000 to 100,000, and more preferably from 5,000 to 50,000. When Mw of the copolymer [α] is within a range of 2,000 to 100,000, a photosensitive composition in which developability and sensitivity are balanced at a higher level, and a cured film having a high heat resistance may be obtained.

The content of the alkali-soluble resin based on the total solid content of the photosensitive composition of the present invention preferably ranges from 20% to 90% by mass, and more preferably from 40% to 85% by mass.

The photocurable composition of the present invention is preferably a photocurable resin composition containing a resin as a base-reactive compound, and is more preferably a photocurable resin composition containing an epoxy resin or a polyamic acid as a base-reactive compound. Specific examples and preferred ranges of the epoxy resin as the base-reactive compound are the same as those described above.

The photocurable composition of the present invention may contain conventionally known additives as necessary within a scope not departing from the effect of the present invention. As for specific additives, a photosensitizer, a flame retardant, a plasticizer, an adhesion accelerator, a surfactant, an antioxidant, an ultraviolet preventing agent, a light stabilizer, a plasticizer, waxes, fillers, a coloring agent (e.g., pigment and dye), a foaming agent, a defoaming agent, a dehydrating agent, an antistatic agent, an antibacterial agent, an antifungal agent, a leveling agent, a dispersing agent, and an ethylenically unsaturated compound may be exemplified. In order to promote the photolysis of the photobase generator, the use of a photosensitizer is appropriate. Also, in order to impart flame retardancy to the photocurable composition, the use of a flame retardant is appropriate, and in order to impart low warpage and low resilience at the time of film formation, the use of a plasticizer is appropriate.

[D] Cured Film Forming Method

The cured film of the present invention is formed by a forming method which includes forming a film by applying the photosensitive composition on a substrate, and exposing the film.

The forming method of the cured film using the photosensitive composition of the present invention is not particularly limited. However, for example, the film may be formed by applying the photosensitive composition on a substrate by any method such as a spin coating method, a slit die coating method, a screen printing method, a roller coating method, a dip coating method, a scanning method, a spray method, a bar coating method, and an ink jet method, forming a coating film (a photosensitive film) by removing a solvent through heating as necessary, and performing a pre-baking step.

As for the substrate, a silicon wafer substrate, a SiO$_2$ wafer substrate, a SiN wafer substrate, a glass substrate, substrates having various metal layers formed on the surfaces thereof, and substrates having plastic films coated on the surfaces thereof may be exemplified.

As for the coating method on the substrate, a spin coating method, a slit die coating method, a screen printing method, a scanning method, and an ink jet method are preferred.

Meanwhile, the photosensitive composition of the present invention may be easily washed off and removed using a conventionally known cleaning liquid, for example, even when adhered to a nozzle of a coating apparatus ejecting unit, a pipe unit of a coating apparatus, and the inside of the coating apparatus. In this case, in order to more efficiently perform the washing-off and removing, the solvent described above as for the solvent included in the photosensitive composition of the present invention may be preferably used as a cleaning liquid.

Also, cleaning liquids described in, for example, Japanese Patent Application Laid-Open Nos. H7-128867, H7-146562, and H8-278637, Japanese Patent Application Laid-Open Nos. 2000-273370, 2006-85140, 2006-291191, 2007-2101, 2007-2102, and 2007-281523 may be properly used as for a cleaning liquid for washing off and removing the photosensitive composition of the present invention.

As for the cleaning liquid, alkylene glycol monoalkyl ether carboxylate, or alkylene glycol monoalkyl ether is preferably used.

These solvents which may be used as cleaning liquids may be used either individually or as a mixture of two or more kinds thereof.

When two or more solvents are mixed, a mixed solvent obtained by mixing a solvent having no hydroxyl group and a solvent having a hydroxyl group is preferred. The mass ratio of a solvent having a hydroxyl group and a solvent having no hydroxyl group ranges from 1/99 to 99/1, preferably from 10/90 to 90/10, and more preferably from 20/80 to 80/20. As for the mixed solvent, a mixed solvent of propylene glycol monomethyl ether acetate (PGMEA) and propylene glycol monomethyl ether (PGME), at a ratio of 60/40, is particularly preferred.

The method for the prebaking processing is not particularly limited, but, generally used hot plate heating, a heating method using a furnace, or light irradiation heating using a xenon lamp according to RTP (rapid thermal processor) may be employed. The hot plate heating and the heating method using a furnace are preferred. As for the hot plate, a commercially available apparatus may be preferably used, and for example, Clean Track Series (manufactured by Tokyo Electron Limited.), D-spin series (manufactured by Dainippon Screen Mfg. Co., Ltd.), and SS series or CS series (manufactured by TOKYO OHKA KOGYO Co., Ltd.) may be preferably used. As for the furnace, for example, Cx series (manufactured by Tokyo Electron Limited.) may be preferably used. As for the prebaking conditions, conditions for heating through a hot plate or an oven at 60° C. to 150° C. (preferably 60° C. to 120° C.) for about 0.5 min to 15 min may be exemplified.

The exposure step of the photosensitive film is performed through a mask as necessary.

As for the actinic ray or radiation applicable to the exposure, infrared light, g-line, h-line, i-line, KrF light, ArF light, X-rays, and electron beam may be exemplified. In view of the exposure amount, sensitivity, and resolution, i-line, KrF light, ArF light, and electron beam are preferred, and in view of versatility, i-line, and KrF light are the most preferred. When i-line is used as the irradiation light, the irradiation is preferably performed at an exposure amount ranging from 100 mJ/cm$^2$ to 10000 mJ/cm$^2$. When KrF light is used, the irradiation is preferably performed at an exposure amount ranging from 30 mJ/cm$^2$ to 300 mJ/cm$^2$. The exposed composition layer may be heated at 70° C. to 180° C. for about 0.5 min to 15 min by using a hot plate or an oven prior to a following development processing, as necessary.

Then, on the exposed composition layer, development (developing step) using a developer is preferably performed in which an exposed portion of the photosensitive film is developed to obtain a patterned film (developing step). Accordingly, a negative type or positive type pattern may be formed.

As for the alkali developer, for example, an alkali aqueous solution of inorganic alkalis such as sodium hydroxide, potassium hydroxide, sodium carbonate, sodium silicate, sodium metasilicate or ammonia water; primary amines such as ethylamine or n-propylamine; secondary amines such as diethylamine or di-n-butylamine; tertiary amines such as triethylamine or methyldiethylamine; alcohol amines such as dimethylethanolamine or triethanolamine; quaternary ammonium salts such as tetramethylammoniumhydroxide, tetraethylammoniumhydroxide; cyclic amines such as pyrrole, piperidine, 1,8-diazabicyclo-(5.4.0)-7-undecene or 1,5-diazabicyclo-(4.3.0)-5-nonene may be used.

Further, the alkali aqueous solution may be added with an alcohol or a surfactant in an appropriate amount to be used.

The alkali concentration of the alkali developer generally ranges from 0.1% to 20% by mass.

The pH of the alkali developer generally ranges from 10.0 to 15.0.

Particularly, an aqueous solution of 1.0% by mass of sodium carbonate is desirable.

As for the developing method, it is possible to apply, for example, a method of dipping a substrate in a bath filled with a developer for a predetermined time (a dipping method), a method of heaping up a developer on a substrate surface by a surface tension and keeping the substrate still for a fixed time, thereby performing development (a puddle method), a method of spraying a developer on a substrate surface (a spraying method), and a method of continuously ejecting a developer on a substrate spinning at a constant speed while scanning a developer ejecting nozzle at a constant rate (a dynamic dispense method). the developing time varied according to the composition of the photosensitive composition but generally ranges from about 30 sec to 240 sec at 25° C. to 40° C.

When the aforementioned various developing methods include ejecting a developer toward the photosensitive film from a development nozzle of a developing apparatus, the ejection pressure of the ejected developer (the flow velocity per unit area of the ejected developer) is preferably 2 mL/sec/mm$^2$ or less, more preferably 1.5 mL/sec/mm$^2$ or less, and still more preferably 1 mL/sec/mm$^2$ or less. The flow velocity has no particular lower limit, but is preferably 0.2 mL/sec/mm$^2$ or more in consideration of throughput.

By setting the ejection pressure of the ejected developer to the above-described range, pattern defects resulting from the resist residue after development may be significantly reduced.

Details on the mechanism are not clear, but it is thought that it is because by setting the ejection pressure in the above-described range, the pressure imposed on the photosensitive film by the developer is decreased and the photosensitive film or patterned film is suppressed from being inadvertently cut or collapsing.

Meanwhile, the ejection pressure (mL/sec/mm$^2$) of the developer is the value at the outlet of the development nozzle in the developing apparatus.

Examples of the method for adjusting the ejection pressure of the developer may include a method of adjusting the ejection pressure by, for example, a pump, and a method of supplying a developer from a pressurized tank and adjusting the pressure to change the ejection pressure.

After the development, a cleaning step using a rinsing liquid may be preferably included.

As for the rinsing liquid in the rinse treatment, pure water is used, and an appropriate amount of a surfactant may be added to be used.

In the rinsing step, the wafer subjected to development is washed by using the rinsing liquid. The method of washing treatment is not particularly limited, but it is possible to employ, for example, a method of continuously ejecting a rinsing liquid on a substrate spinning at a constant speed (spin coating method), a method of dipping a substrate in a bath filled with a rinsing liquid for a fixed time (dipping method), and a method of spraying a rinsing liquid on a substrate surface (spraying method), and among them, it is preferred that the washing treatment is performed by the spin coating method and after the washing, the substrate is spun at a rotational speed from 2,000 rpm to 4,000 rpm to remove the rinsing liquid from the substrate. It is also preferred that a heating step (post baking) is included after the rinsing step. The developer and rinsing liquid remaining between patterns and in the inside of the pattern are removed by the baking. The heating step after the rinsing step may be performed by heating the patterned film by a heating apparatus such as a hot plate or an oven.

In this post baking, the heating temperature usually ranges from 120° C. to 250° C., and preferably 160° C. to 230° C. The heating time varies according to heating units, but generally ranges from about 5 min to 30 min at the heating on a hot plate, and generally ranges from about 30 min to 90 min at the heating in an oven.

When the post baking is performed, a step baking method for performing heating two or more times may be employed.

After the developing step, as necessary, post-heating and/or post-exposure may be performed on the formed patterned film to further promote the curing of the patterned film (a post-curing step through a film hardening treatment).

Accordingly, a light resistance, a weather resistance, and a film strength are improved.

The film hardening treatment is performed to further cure the patterned film on the substrate so as to further give, for example, a solvent resistance to the film. As for the film hardening method, a heating treatment (calcination) is preferred. For example, a polymerization reaction of the polymerizable groups remaining in the resin at the time of post-heating may be used. As for the conditions of the post-heating treatment, the temperature preferably ranges from 100° C. to 600° C., more preferably from 200° C. to 500° C., and particularly preferably 200° C. to 450° C., and the time ranges preferably from 1 min to 3 hours, more preferably from 1 min to 2 hours, and particularly preferably from 1 min to 1 hour. The post-heating treatment may be performed in divided several steps.

Also, in the present invention, a polymerization reaction between the polymerizable groups still remaining in the polymer may be caused through irradiation of high-energy rays such as light or radiation irradiation instead of the heating treatment so as to perform the film hardening. As for the high energy rays, electron beam, UV rays, and X rays may be exemplified, but the method is not particularly limited thereto.

When the electron beam is used as the high energy rays, the energy preferably ranges from 0.1 keV to 50 keV, more preferably from 0.2 keV to 30 keV, and particularly preferably from 0.5 keV to 20 keV. The total dose of the electron beam preferably ranges from 0.01 μC/cm² to 5 μC/cm², more preferably from 0.01 μC/cm² to 2 jC/cm², and particularly preferably from 0.01 μC/cm² to 1 μC/cm². The substrate temperature at the irradiation of the electron beam preferably ranges from 0° C. to 500° C., more preferably from 20° C. to 450° C., and particularly preferably from 20° C. to 400° C. The pressure preferably ranges from 0 kPa to 133 kPa, more preferably from 0 kPa to 60 kPa, and particularly preferably from 0 kPa to 20 kPa.

In view of preventing oxidation of the polymer, as for the atmosphere around the substrate, an inert atmosphere of Ar, He, or nitrogen is preferably used. Also, a gas such as oxygen, hydrocarbon, or ammonia may be added for the purpose of a reaction with plasma, electromagnetic waves, and chemical species which is caused by interaction with electron beam. The electron beam irradiation may be performed several times, and in this case, the condition for irradiating electron beam does not need to be the same every time, but may be varied at different times.

UV rays may be used as for the high energy rays. The radiation wavelength region when the UV rays are used preferably ranges from 160 nm to 400 nm, and the output preferably ranges from 0.1 mWcm⁻² to 2000 mWcm⁻² just above the substrate. The substrate temperature at the time of UV irradiation preferably ranges from 250° C. to 450° C., more preferably from 250° C. to 400° C., and particularly preferably from 250° C. to 350° C. In view of preventing the oxidation of the polymer of the present invention, as for the atmosphere around the substrate, an inert atmosphere of Ar, He, or nitrogen is preferably used. Also, the pressure at this time preferably ranges from 0 kPa to 133 kPa.

The heating treatment and the treatment irradiation of high-energy rays such as light or radiation irradiation may be simultaneously or sequentially performed so as to carry out film hardening.

The photocurable composition of the present invention may be used in various applications. For example, it may be properly used for applications such as a solid-state imaging device, a color filter for a liquid crystal display device, an interlayer insulating film and an optical waveguide.

Descriptions will be made in detail on components other than the compound represented by Formula (I) above, which may be contained in the photosensitive composition of the present invention (hereinafter, which may be simply referred to as "a chemical amplification resist composition of the present invention") when the photosensitive composition of the present invention is used as for the chemical amplification resist composition. Meanwhile, specific examples, preferred ranges, and content ranges of the compound represented by Formula (I) above contained in the chemical amplification resist composition are the same as those described above.

[1] (B) Compound Capable of Generating an Acid Upon Irradiation with an Actinic Ray or Radiation The chemical amplification resist composition of the present invention preferably contains (B) a compound capable of generating an acid upon irradiation with an actinic ray or radiation (hereinafter, these compounds are properly abbreviated as an "acid generator").

As a preferred form of the acid generator, an onium compound may be exemplified. Examples of the onium compound may include a sulfonium salt, an iodonium salt, and a phosphonium salt.

As another preferred form of the acid generator, a compound which generates a sulfonic acid, an imide acid or a methide acid upon irradiation with an actinic ray or radiation may be exemplified. Examples of the acid generator in such a form may include a sulfonium salt, an iodonium salt, a phosphonium salt, an oxime sulfonate, and an imide sulfonate.

The acid generator is preferably a compound which generates an acid upon irradiation with electron beam or extreme-ultraviolet rays.

In the present invention, as for a preferred onium compound, a sulfonium compound represented by Formula (5) below, or an iodonium compound represented by Formula (6) below may be exemplified.

[Chem. 9]

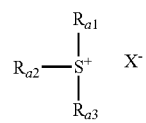

(5)

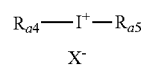

(6)

In Formulas (5) and (6),

Each of $R_{a1}$, $R_{a2}$, $R_{a3}$, $R_{a4}$ and $R_{a5}$ independently represents an organic group.

$X^-$ represents an organic anion.

Hereinafter, the sulfonium compound represented by Formula (5) and the iodonium compound represented by Formula (6) will be described in more detail.

Each of $R_{a1}$ to $R_{a3}$ in Formula (5) above and $R_{a4}$ and $R_{a5}$ in Formula (6) above independently represents an organic group, but preferably each of at least one of $R_{a1}$ to $R_{a3}$ and at least one of $R_{a4}$ and $R_{a5}$ is an aryl group. As for the aryl group, a phenyl group, and a naphthyl group are preferred, and a phenyl group is more preferred.

As for the organic anion of $X^-$ in Formulas (5) and (6) above, for example, a sulfonate anion, a carboxylate anion, a bis(alkylsulfonyl) amide anion, and a tris(alkylsulfonyl) methide anion may be exemplified. An organic anion represented by formula (7), (8) or (9) below is preferred, and an organic anion represented by Formula (7) below is more preferred.

[Chem. 10]

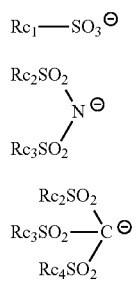

(7)
(8)
(9)

In Formulas (7), (8) and (9) above, each of $R_{c1}$, $R_{c2}$, $R_{c3}$ and $R_{c4}$ represents an organic group.

The organic anion of $X^-$ corresponds to an acid generated upon irradiation with an actinic ray or radiation such as electron beam or extreme-ultraviolet rays, e.g., a sulfonic acid, an imide acid, or a methide acid.

As for the organic group of $R_{c1}$ to $R_{c4}$, for example, an alkyl group, a cycloalkyl group, an aryl group and a group having a plurality of linked groups thereof may be exemplified. Among these organic groups, an alkyl group, a cycloalkyl group, or a phenyl group in which one position is substituted with a fluorine atom or a fluoroalkyl group is preferred. A plurality of organic groups of $R_{c2}$ to $R_{c4}$ may be linked together to form a ring, and as for the group having a plurality of linked organic groups, an alkylene group substituted with a fluorine atom or a fluoroalkyl group is preferred. By containing the fluorine atom or the fluoroalkyl group, the acidity of the acid generated by light irradiation is increased, thereby improving the sensitivity. Meanwhile, it is preferred that a terminal group does not contain a fluorine atom as a substituent.

Also, in the present invention, in view of suppressing diffusion of an acid generated by exposure into a non-exposed portion, thereby improving a resolution or a pattern shape, the compound (B) which generates an acid is preferably a compound which generates an acid with a volume of 130 Å³ or more (more preferably, a sulfonic acid), more preferably a compound which generates an acid with a volume of 200 Å³ or more (more preferably, a sulfonic acid), still further preferably, a compound which generates an acid with a volume of 240 Å³ or more (more preferably, a sulfonic acid), and particularly preferably a compound which generates an acid with a volume of 400 Å³ or more (more preferably, a sulfonic acid). Meanwhile, in view of the sensitivity or the coating solvent solubility, the volume is preferably 2000 Å³ or less, and more preferably 1500 Å³ or less.

The value of the volume was obtained using, FUJITSU LIMITED manufactured by "WinMOPAC". That is, the "accessible volume" of each acid may be calculated by, first, inputting a chemical structure of an acid according to each case, determining the most stable conformation of each acid by a molecular force field calculation using a MM3 method with an initial structure of this structure, and performing a molecular orbital calculation using a PM3 method for the most stable conformation.

Hereinafter, a particularly preferred acid generator in the present invention will be exemplified as below. Also, some examples are given calculated values of volume (unit: Å³). Meanwhile, the value calculated herein is a volume value of an acid in which a proton is bound to an anion moiety.

[Chem. 11]

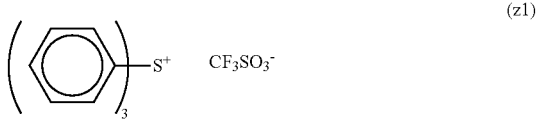

(z1)

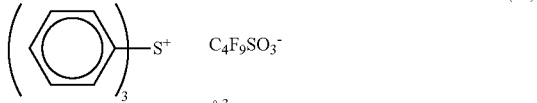

(z2)

113 Å³

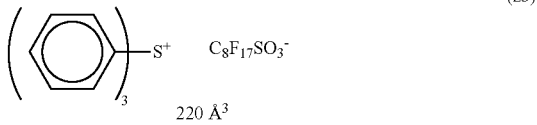

(z3)

220 Å³

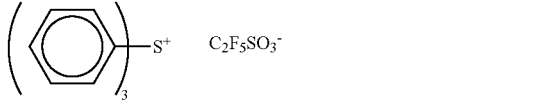

(z4)

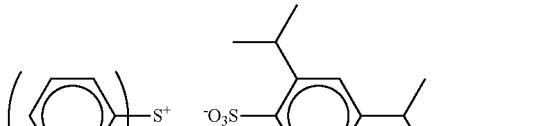

(z5)

303 Å³

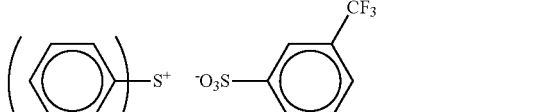

(z6)

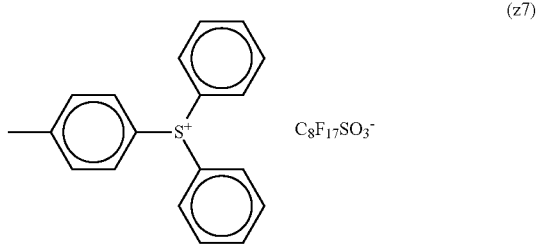

(z7)

(z8)
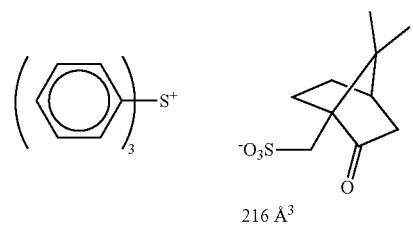
216 Å³
(z9)
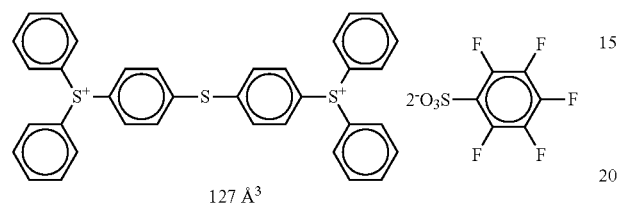
127 Å³
(z10)
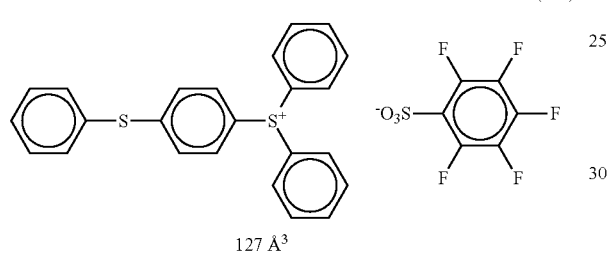
127 Å³
(z11)
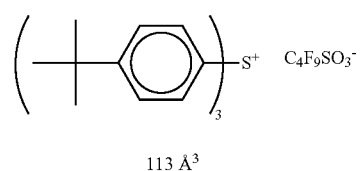
113 Å³
(z12)
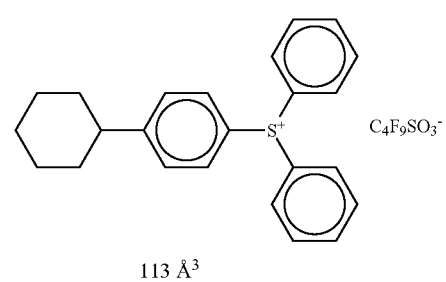
113 Å³
(z13)
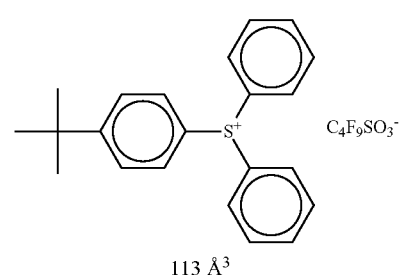
113 Å³
(z14)
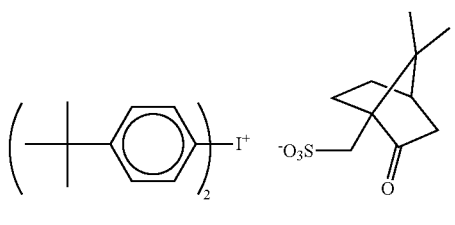
216 Å³
(z15)
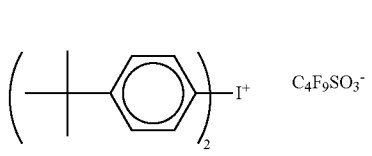
113 Å³
(z16)
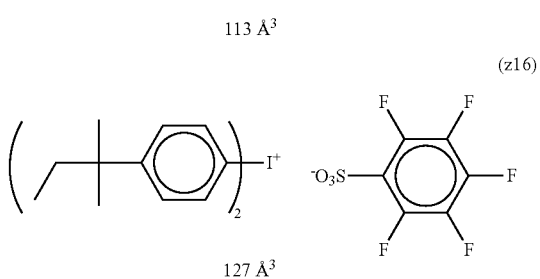
127 Å³
(z17)
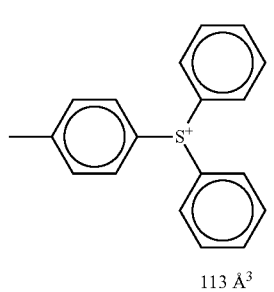
113 Å³
[Chem. 12]
(z18)
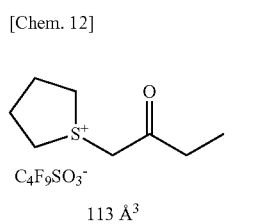
113 Å³
(z19)
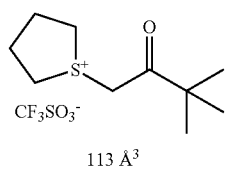
113 Å³
(z20)
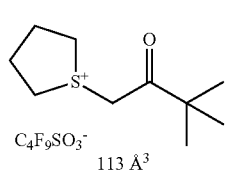
113 Å³

(z21)
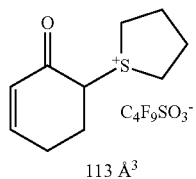
113 Å³
(z22)
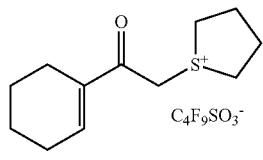
113 Å³
(z23)
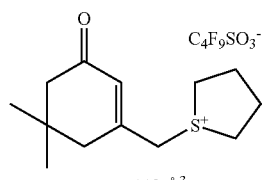
113 Å³
(z24)
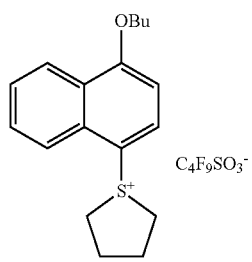
113 Å³
(z25)
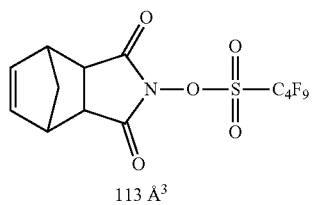
113 Å³
(z26)
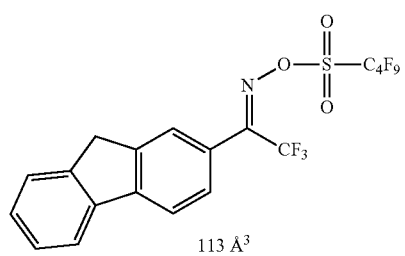
113 Å³
(z27)
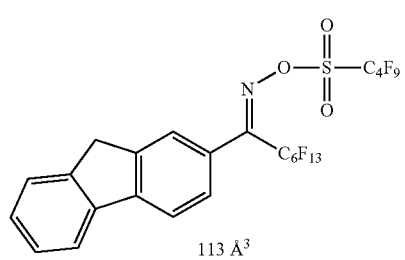
113 Å³
(z28)
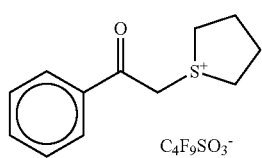
113 Å³
(z29)
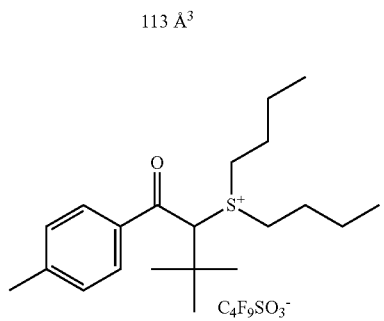
113 Å³
(z30)
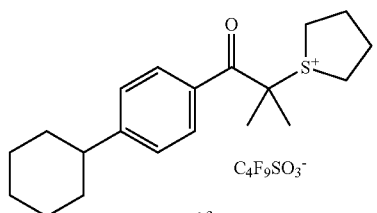
113 Å³
(z31)
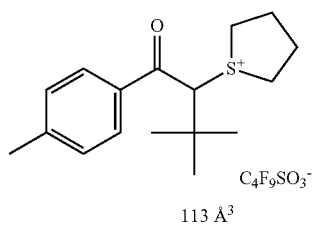
113 Å³
(z32)
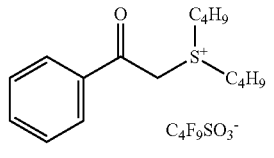
113 Å³
(z33)
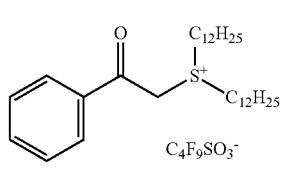
113 Å³
(z34)
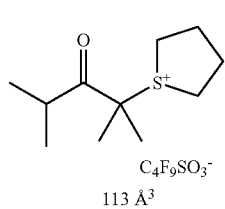
113 Å³

-continued
(z35)
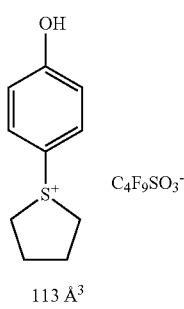
113 Å³
(z36)
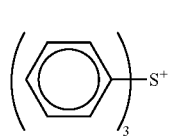
393 Å³
(z37)
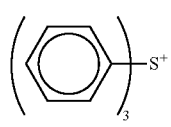
136 Å³
(z38)
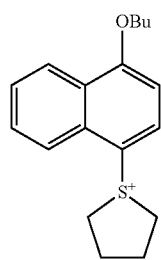
136 Å³
(z39)
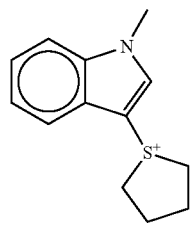
136 Å³
(z40)
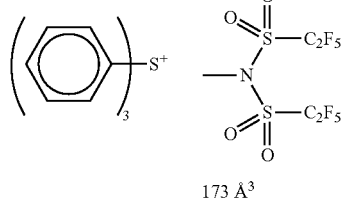
173 Å³
-continued
(z41)
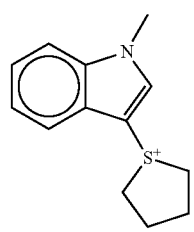
113 Å³
[Chem. 13]
(z42)
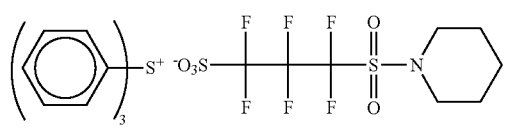
244 Å³
(z43)
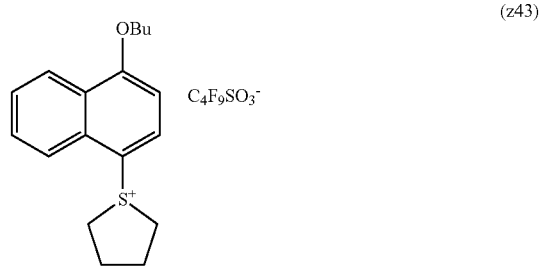
113 Å³
(z44)
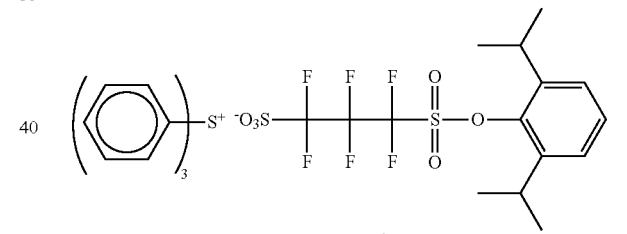
347 Å³
(z45)
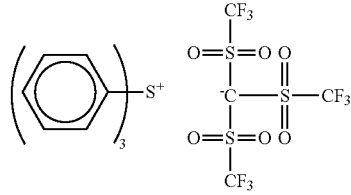
189 Å³
(z46)
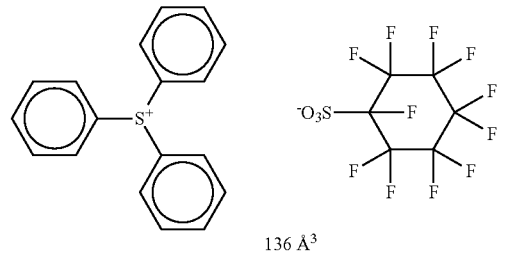
136 Å³

(z47)
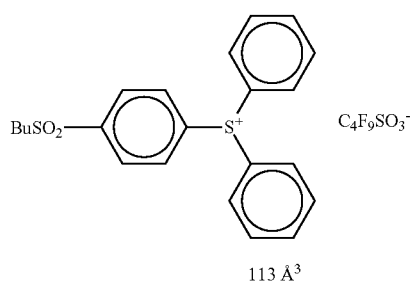
113 Å³
(z48)
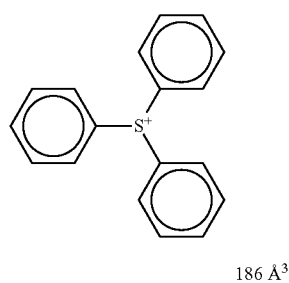
186 Å³
(z49)
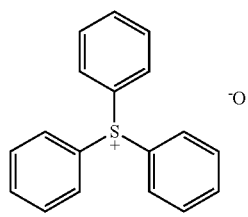
271 Å³
(z50)
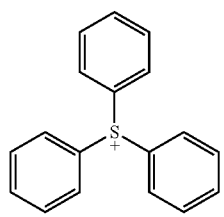
291 Å³
(z51)
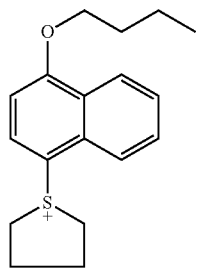
271 Å³
(z52)
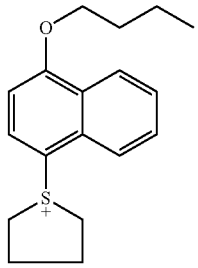
244 Å³
(z53)
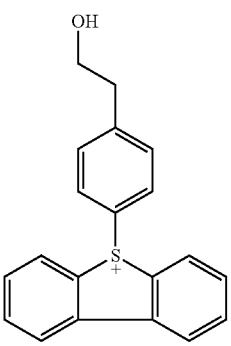
437 Å³
(z54)
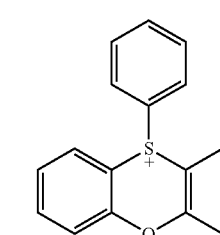
303 Å³
(z55)
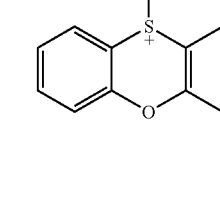
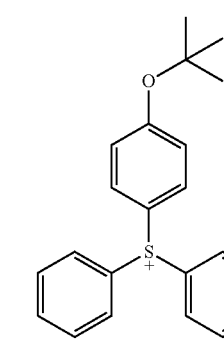
303 Å³

[Chem. 14]
(z56)
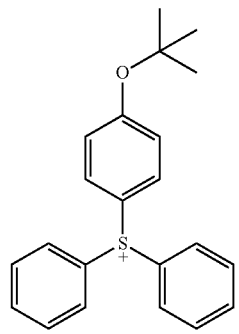 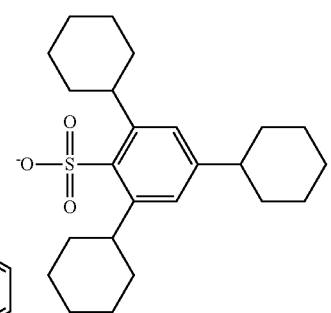
437 Å³
(z57)
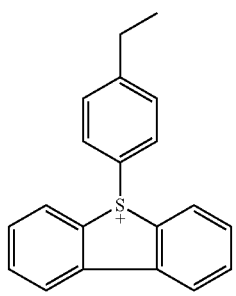 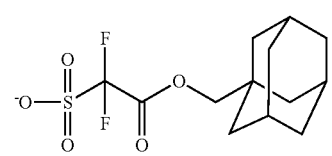
271 Å³
(z58)
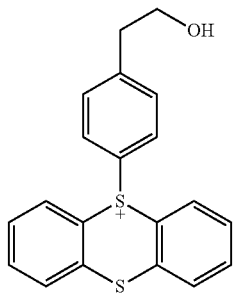 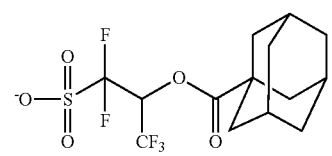
291 Å³
(z59)
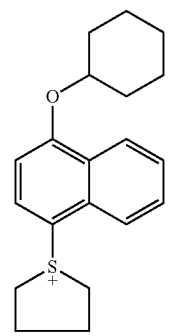 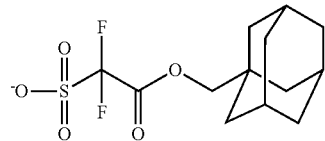
271 Å³
(z60)
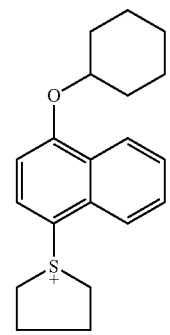
244 Å³
(z61)
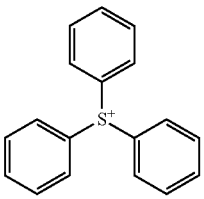
311 Å³
(z62)
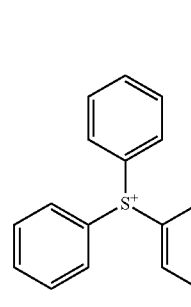
437 Å³
(z63)
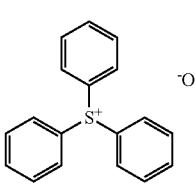
535 Å³
(z64)
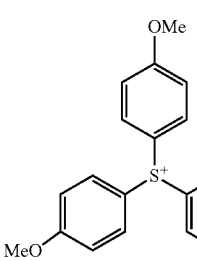
437 Å³

-continued

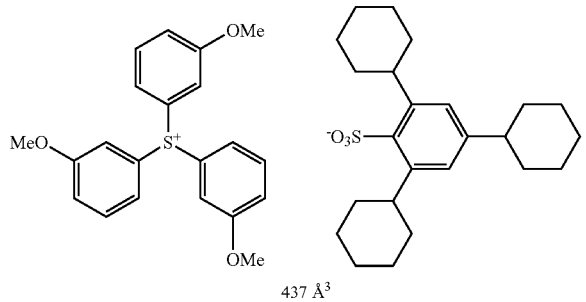

(z65)

437 Å³

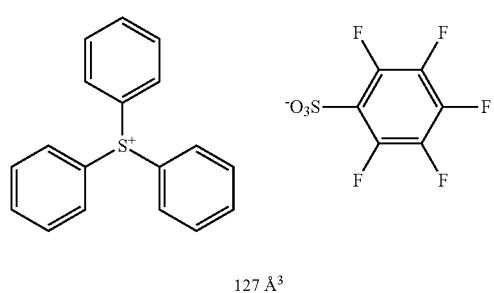

(z66)

127 Å³

[Chem. 15]

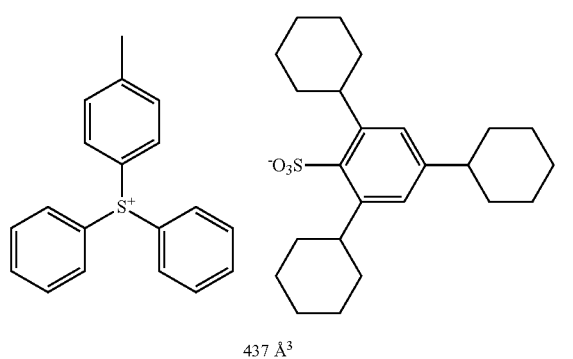

(z67)

437 Å³

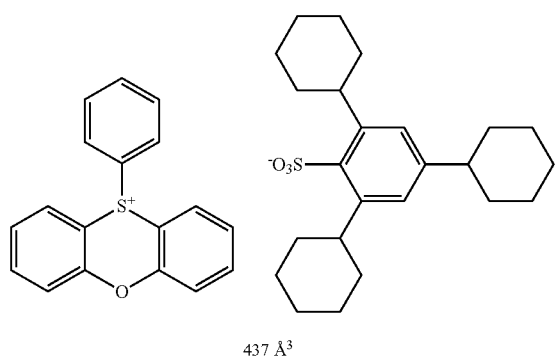

(z68)

437 Å³

The content of the acid generator (B) in the composition preferably ranges from 0.1% to 25% by mass, more preferably from 0.5% to 20% by mass, and still more preferably from 1% to 18% by mass based on the total solid content of the resist composition.

The acid generator may be used either alone or in combination of two or more kinds thereof.

[2] Compound Capable of Decomposing by an Action of an Acid to Generate an Acid

The chemical amplification resist compound (an actinic ray-sensitive or radiation-sensitive composition) of the present invention may contain one or more kinds of compounds capable of decomposing by the action of an acid to generate an acid (hereinafter, also referred to as an "acid proliferating agent"). An acid generated by the acid proliferating agent is preferably a sulfonic acid, a methide acid or an imide acid. Specific examples of the acid proliferating agent may include compounds described in [0205] to [0208] of Japanese Patent Application Laid-Open No. 2009-229774, and [0407] to [0409] of Japanese Patent Application Laid-Open No. 2011-33729.

The content of the acid proliferating agent preferably ranges from 0.1% by mass to 50% by mass, more preferably from 0.5% by mass to 30% by mass, and still more preferably from 1.0% by mass to 20% by mass, based on the total solid content of the composition.

The quantity ratio of an acid proliferating agent to an acid generator (the solid content of the acid proliferating agent based on the total solid content of the composition/the solid content of the acid generator based on the total solid content of the composition) is not particularly limited, but preferably ranges from 0.01 to 50, more preferably from 0.1 to 20, and particularly preferably from 0.2 to 1.0.

[3] (C) Resin Having a Repeating Unit Having a Group Capable of Decomposing by an Action of an Acid to Generate a Polar Group (Hereinafter, Also Referred to as an Acid-Decomposable Group)

The chemical amplification resist compound (an actinic ray-sensitive or radiation-sensitive composition) of the present invention may contain a resin having a repeating unit having a group capable of decomposing by the action of an acid to generate a polar group (hereinafter, also referred to as a resin (C)).

The resin (C) is a resin capable of increasing the polarity by the action of an acid to increase the solubility in an alkali developer in a case of a positive-type development using the alkali developer, or a resin capable of increasing the polarity by the action of an acid to decrease the solubility in a developer containing an organic solvent in a case of a negative-type development using a developer containing the organic solvent. Meanwhile, a carboxyl group as the polar group serves as an alkali-soluble group in a case of the positive-type development using the alkali developer.

The chemical amplification resist compound (the actinic ray-sensitive or radiation-sensitive resin composition) according to the present invention may be used for the positive-type development (an exposed portion is removed and an unexposed portion is remained as a pattern), or may be used for the negative-type development (an exposed portion is remained as a pattern, and an unexposed portion is removed). That is, the chemical amplification resist compound (the actinic ray-sensitive or radiation-sensitive resin composition) according to the present invention may be a chemical amplification resist compound (actinic ray-sensitive or radiation-sensitive resin composition) for alkali development, which is used for development using an alkali developer, or a chemical amplification resist compound (the actinic ray-sensitive or radiation-sensitive resin composition) for organic solvent development, which is used for development using an organic solvent-containing developer. Here, the use for alkali development refers to, at least, a use for a developing process using an alkali developer, and the use for organic solvent development refers to, at least, a use for a developing process using an organic solvent-containing developer.

The chemical amplification resist compound (the actinic ray-sensitive or radiation-sensitive resin composition) of the present invention is typically a resist composition, and is preferably a positive-type resist composition (that is, a resist composition for alkali development). Also, the composition according to the present invention is typically a chemical amplification resist composition.

The chemical amplification resist composition of the present invention preferably contains the resin (C) having an acid-decomposable group when a positive-type pattern is formed.

The resin may include the acid-decomposable group at the main chain or the side chain of the resin, or both of the main chain and the side chain. The resin preferably includes the acid-decomposable group at the side chain. Also, the resin (C) preferably has a repeating unit having an acid-decomposable group.

As for the acid-decomposable group, a group in which a hydrogen atom of an alkali-soluble group such as —COOH or —OH is substituted with a group capable of leaving by the action of an acid is preferred. As for the group capable of leaving by the action of an acid, an acetal group or a tertiary ester group is particularly preferred.

In a case where the acid-decomposable group is bonded as a side chain, as for a matrix resin, an alkali-soluble resin having —OH or —COOH at the side chain may be exemplified. Examples of the alkali-soluble resin may include those described below.

The alkali dissolution rate of the alkali-soluble resin is preferably 17 nm/sec or more when measured by using 2.38% by mass of a tetramethylammonium hydroxide (TMAH) aqueous solution (23° C.). This rate is particularly preferably 33 nm/sec or more.

In this point of view, as a particularly preferable alkali-soluble resin, a resin including a hydroxystyrene structural unit such as o-, m- and p-poly(hydroxystyrene) and copolymers thereof, hydrogenated poly(hydroxystyrene), halogen- or alkyl-substituted poly(hydroxystyrene), partially O-alkylated or O-acylated poly(hydroxystyrene), styrene-hydroxystyrene copolymers, α-methylstyrene-hydroxystyrene copolymers and hydrogenated novolak resin; and a resin including a repeating unit having a carboxyl group such as (meth)acrylic acid and norbornene carboxylic acid may be exemplified.

As for a preferred repeating unit having an acid-decomposable group, for example, t-butoxycarbonyloxystyrene, 1-alkoxyethoxy styrene and (meth)acrylic tertiary alkyl ester may be exemplified. As for the repeating unit, 2-alkyl-2-adamantyl (meth) acrylate or dialkyl(1-adamantyl) methyl (meth) acrylate is more preferred.

A resin capable of decomposing by the action of an acid to increase the solubility in an alkali developer is obtained by reacting a resin with a precursor of a group capable of leaving by the action of an acid, or by copolymerizing a variety of monomers with an alkali-soluble resin monomer bonded to a group capable of leaving by the action of an acid as disclosed in Europe Patent 254853, and Japanese Patent Application Laid-Open No. H2-25850, H3-223860 and H4-251259.

In the case where KrF excimer laser light, electron beam, X-ray or high-energy beam having a wavelength of 50 nm or less (e.g., EUV) is irradiated on the composition of the present invention, the resin preferably has a hydroxystyrene repeating unit. More preferably, the resin is a copolymer of hydroxystyrene and hydroxystyrene protected by a group capable of leaving by the action of an acid, or a copolymer of hydroxystyrene and (meth)acrylic tertiary alkyl ester.

As for such a resin, specifically, a resin having a repeating unit as represented by Formula (A) below may be exemplified.

[Chem. 16]

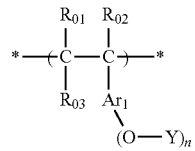

(A)

In Formula, each of $R_{01}$, $R_{02}$ and $R_{03}$ independently represents, for example, a hydrogen atom, an alkyl group, a cycloalkyl group, a halogen atom, a cyano group or an alkoxycarbonyl group. $Ar_1$ represents an alkylene group or an aromatic ring group. $R_{03}$ may be an alkylene group, and may be bound to $Ar_1$ as an aromatic ring group to form a ring together with a —C—C— chain. Also, $R_{03}$ and $Ar_1$ may be alkylene groups and may be bound to each other to form, for example, a 5- or 6-membered ring together with a —C—C— chain.

Each of n Y's independently represents a hydrogen atom or a group capable of leaving by the action of an acid. Meanwhile, at least one Y represents a group capable of leaving by the action of an acid.

n represents an integer of 1 to 4, and is preferably 1 or 2, and is more preferably 1.

The alkyl group as $R_{01}$ to $R_{03}$ is, for example, an alkyl group having 20 or less carbon atoms, and is preferably a methyl group, an ethyl group, a propyl group, an isopropyl group, a n-butyl group, a sec-butyl group, a hexyl group, a 2-ethylhexyl group, an octyl group or a dodecyl group. More preferably, these alkyl groups may be alkyl groups having 8 or less carbon atoms. Also, these alkyl groups may have substituents.

As for the alkyl group contained in the alkoxycarbonyl group, the same as alkyl groups in $R_{01}$ to $R_{03}$ are preferred.

The cycloalkyl group may be a monocyclic cycloalkyl group or a polycyclic cycloalkyl group. Preferably, a monocyclic cycloalkyl group having 3 to 8 carbon atoms, such as a cyclopropyl group, a cyclopentyl group and a cyclohexyl group may be exemplified. Meanwhile, these cycloalkyl groups may have substituents.

As for the halogen atom, a fluorine atom, a chlorine atom, a bromine atom and an iodine atom may be exemplified, and a fluorine atom is more preferred.

When $R_{03}$ represents an alkylene group, as for the alkylene group, preferably, a group having 1 to 8 carbon atoms such as a methylene group, an ethylene group, a propylene group, a butylene group, a hexylene group and an octylene group may be exemplified.

The aromatic ring group as $Ar_1$ preferably has 6 to 14 carbon atoms, and for example, a benzene ring, a toluene ring and a naphthalene ring may be exemplified. Meanwhile, these aromatic ring groups may have substituents.

As for Y, that is, a group capable of leaving by the action of an acid, for example, a group represented by —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$) or —CH($R_{36}$)(Ar) may be exemplified.

In the formula, each of $R_{36}$ to $R_{39}$ independently represents an alkyl group, a cycloalkyl group, an aryl group, an aralkyl group or an alkenyl group. $R_{36}$ and $R_{37}$ may be bound to each other to form a ring structure.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl group as $R_{36}$ to $R_{39}$, $R_{01}$ or $R_{02}$ is preferably an alkyl group having 1 to 8 carbon atoms, and for example, a methyl group, an ethyl group, a propyl group, a n-butyl group, a sec-butyl group, a hexyl group and an octyl group may be exemplified.

The cycloalkyl group as for $R_{36}$ to $R_{39}$, $R_{01}$ or $R_{02}$ may be a monocyclic cycloalkyl group, or a polycyclic cycloalkyl group. As for the monocyclic cycloalkyl group, a cycloalkyl group having 3 to 8 carbon atoms is preferred, and for example, a cyclopropyl group, a cyclobutyl group, a cyclopentyl group, and a cyclohexyl group and a cyclooctyl group may be exemplified. As for the polycyclic cycloalkyl group, a cycloalkyl group having 6 to 20 carbon atoms is preferred, and for example, an adamantyl group, a norbornyl group, an isobornyl group, a camphanyl group, a dicyclopentyl group, an α-pinel group, a tricyclodecanyl group, a tetracyclodecyl group and an androstanyl group may be exemplified. Meanwhile, a part of carbon atoms in the cycloalkyl group may be substituted with hetero atoms such as an oxygen atom.

The aryl group as for $R_{36}$ to $R_{39}$, $R_{01}$ $R_{02}$ or Ar is preferably an aryl group having 6 to 10 carbon atoms, and for example, a phenyl group, a naphthyl group and an anthryl group may be exemplified.

The aralkyl group as for $R_{36}$ to $R_{39}$, $R_{01}$ or $R_{02}$ is preferably an aralkyl group having 7 to 12 carbon atoms, and for example, a benzyl group, a phenethyl group, and a naphthylmethyl group are preferred.

The alkenyl group as $R_{36}$ to $R_{39}$, $R_{01}$ or $R_{02}$ is preferably an alkenyl group having 2 to 8 carbon atoms, and for example, a vinyl group, an allyl group, and a butenyl group and a cyclohexenyl group may be exemplified.

The aryl group as $R_{36}$ to $R_{39}$, $R_{01}$ $R_{02}$ or Ar is preferably an aryl group having 6 to 10 carbon atoms, and for example, a phenyl group, a naphthyl group and an anthryl group may be exemplified.

The aralkyl group as $R_{36}$ to $R_{39}$, $R_{01}$ or $R_{02}$ is preferably an aralkyl group having 7 to 12 carbon atoms, and for example, a benzyl group, a phenethyl group, and a naphthylmethyl group are preferred.

The alkenyl group as $R_{36}$ to $R_{39}$, $R_{01}$ or $R_{02}$ is preferably an alkenyl group having 2 to 8 carbon atoms, and for example, a vinyl group, an allyl group, a butenyl group and a cyclohexenyl group may be exemplified.

A ring which may be formed by a bond of $R_{36}$ and $R_{37}$ may be monocyclic or polycyclic. As for a monocyclic structure, a cycloalkane structure having 3 to 8 carbon atoms is preferred, and for example, a cyclopropane structure, a cyclobutane structure, a cyclopentane structure, a cyclohexane structure, a cycloheptane structure and a cyclooctane structure may be exemplified, as for a polycyclic structure, a cycloalkane structure having 6 to 20 carbon atoms is preferred, and for example, an adamantane structure, a norbornane structure, a dicyclopentane structure, a tricyclodecane structure and a tetracyclododecane structure may be exemplified. Meanwhile, a part of carbon atoms in the ring structure may be substituted with hetero atoms such as an oxygen atom.

Each of the groups described above may have a substituent. As for the substituent, for example, an alkyl group, a cycloalkyl group, an aryl group, an amino group, an amide group, an ureido group, an urethane group, a hydroxyl group, a carboxyl group, a halogen atom, an alkoxy group, a thioether group, an acyl group, an acyloxy group, an alkoxycarbonyl group, a cyano group and a nitro group may be exemplified. Each of these substituents preferably has 8 or less carbon atoms.

A group in which a plurality of repeating units represented by Formula (A) above are bound to each other at a portion of Y (group capable of leaving by the action of an acid) may be used.

As for Y, that is, a group capable of leaving by the action of an acid, a structure represented by Formula (B) below is more preferred.

[Chem. 17]

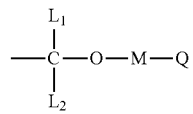

(B)

In the formula, each of $L_1$ and $L_2$ independently represents a hydrogen atom, an alkyl group, a cycloalkyl group, an aryl group or an aralkyl group.

M represents a single bond or a divalent linking group.

Q represents an alkyl group, a cycloalkyl group, a cyclic aliphatic group, aromatic ring group, an amino group, an ammonium group, a mercapto group, a cyano group or an aldehyde group. Meanwhile, these cyclic aliphatic groups and aromatic ring groups may contain a hetero atom.

Meanwhile, at least two of Q, M and $L_1$ may be bound to each other to form a 5- or 6-membered ring.

The alkyl group as for $L_1$ and $L_2$ may be an alkyl group having 1 to 8 carbon atoms, and specifically, a methyl group, an ethyl group, a propyl group, a n-butyl group, a sec-butyl group, a hexyl group and an octyl group may be exemplified.

The cycloalkyl group as for $L_1$ and $L_2$ may be a cycloalkyl group having 3 to 15 carbon atoms, and specifically, a cyclopentyl group, a cyclohexyl group, a norbornyl group and an adamantyl group may be exemplified.

The aryl group as for $L_1$ and $L_2$ may be an aryl group having 6 to 15 carbon atoms, and specifically, a phenyl group, a tolyl group, a naphthyl group and an anthryl group may be exemplified.

The aralkyl group as for $L_1$ and $L_2$ may be an aralkyl group having 6 to 20 carbon atoms, and specifically, a benzyl group and a phenethyl group may be exemplified.

The divalent linking group as for M may be, for example, an alkylene group (e.g., a methylene group, an ethylene group, a propylene group, a butylene group, a hexylene group or an octylene group), a cycloalkylene group (e.g., a cyclopentylene group or a cyclohexylene group), an alkenylene group (e.g., an ethenylene group, a propenylene group or a butenylene group), an arylene group (e.g., a phenylene group, a tolylene group or a naphthylene group), —S—, —O—, —CO—, —SO$_2$—, —N(R$_0$)— or a combination of two or more thereof. Here, $R_0$ is a hydrogen atom or an alkyl group. The alkyl group as for $R_0$ may be an alkyl group having 1 to 8 carbon atoms, and specifically, a methyl group, an ethyl group, a propyl group, a n-butyl group, a sec-butyl group, a hexyl group and an octyl group may be exemplified.

The alkyl group and the cycloalkyl group as for Q are the same as respective groups as $L_1$ and $L_2$ as described above.

As for the cyclic aliphatic group or the aromatic ring group as Q, for example, the cycloalkyl group and the aryl group as $L_1$ and $L_2$ as described above may be exemplified. Each of the cycloalkyl group and the aryl group preferably has 3 to 15 carbon atoms.

As for the cyclic aliphatic group or the aromatic ring group containing a hetero atom as Q, for example, a group having a heterocyclic structure, such as thiirane, cyclothiolane, thiophene, furan, pyrrole, benzothiophene, benzofuran, benzopyrrole, triazine, imidazole, benzimidazole, triazole, thiadiazole, thiazole and pyrrolidone, may be exemplified. However, the group is not limited these examples as long as it is a ring formed by carbon and hetero atoms, or a ring formed by only hetero atoms.

As for the ring structure which may be formed by a bond of at least two of Q, M and $L_1$, for example, a 5- or 6-membered ring structure obtained from a propylene group or a butylene group formed by these may be exemplified. Meanwhile, this 5- or 6-membered ring structure contains an oxygen atom.

Each group represented by $L_1$, $L_2$, M or Q in Formula (2) may have a substituent. As for the substituent, for example, an alkyl group, a cycloalkyl group, an aryl group, an amino group, an amide group, an ureido group, an urethane group, a hydroxyl group, a carboxyl group, a halogen atom, an alkoxy group, a thioether group, an acyl group, an acyloxy group, an alkoxycarbonyl group, a cyano group and a nitro group may be exemplified. Each of these substituents preferably has 8 or less carbon atoms.

As for the group represented by -(M-Q), a group having 1 to 30 carbon atoms is preferred, and a group having 5 to 20 carbon atoms is more preferred. Particularly, in view of suppressing outgassing, a group having 6 or more carbon atoms is preferred.

Specific examples of the repeating unit represented by Formula (A) are described below, but are not limited thereto.

[Chem. 18]

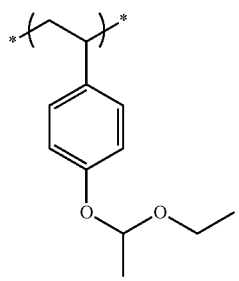
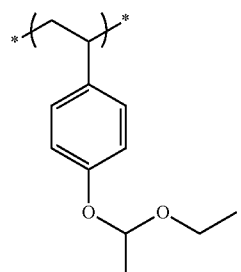
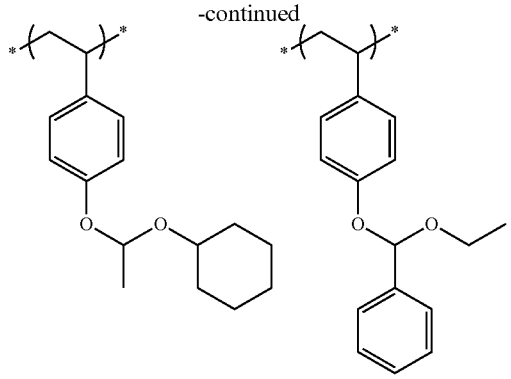

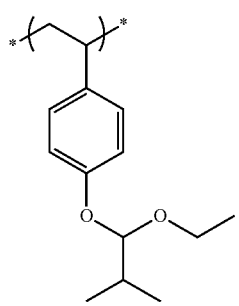
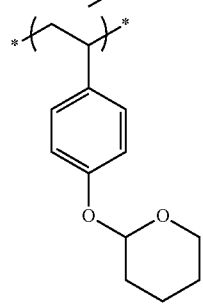
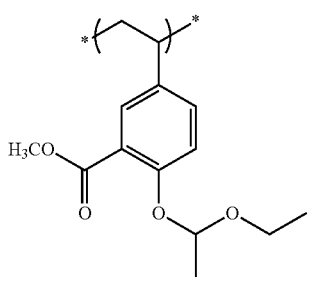

-continued

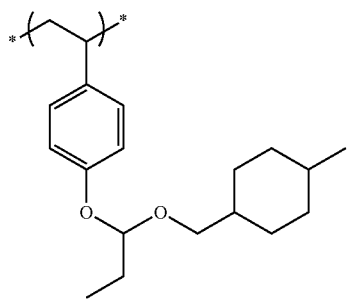

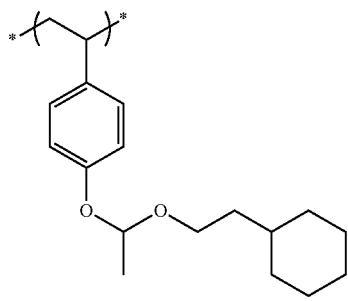

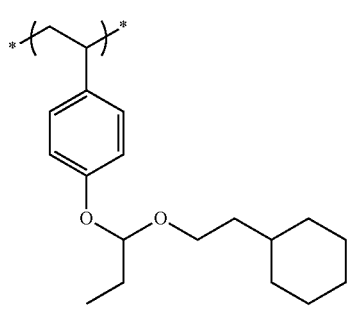

49
-continued
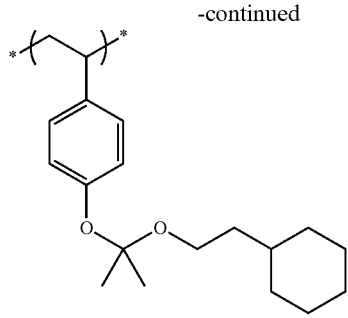
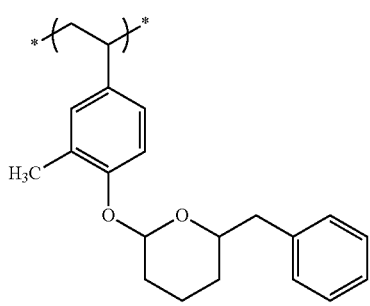
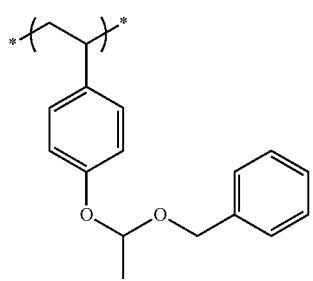
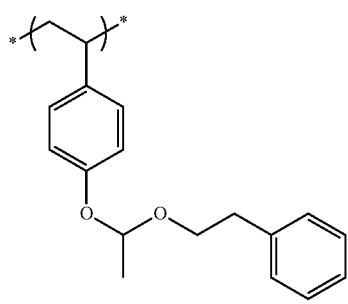
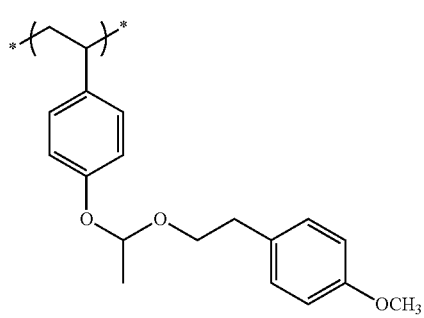
50
-continued
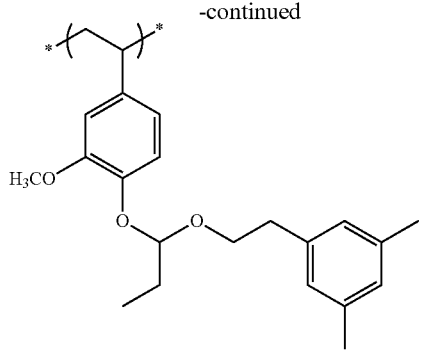
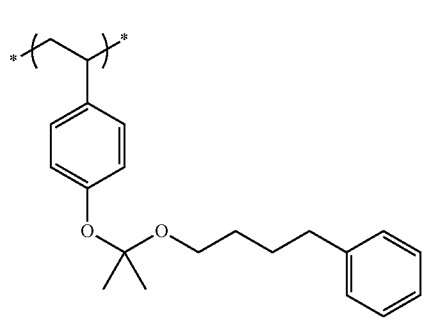
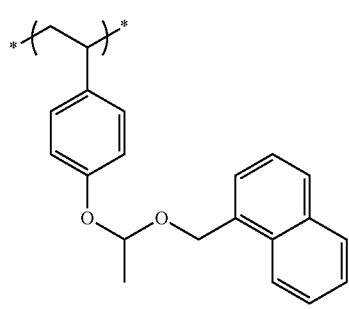
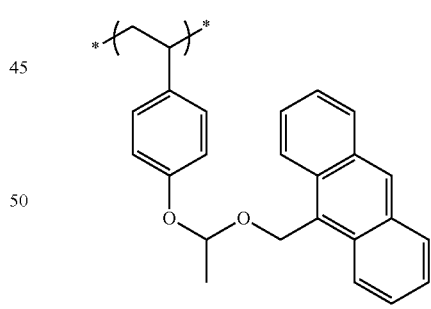
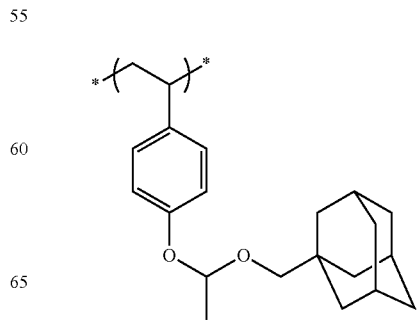

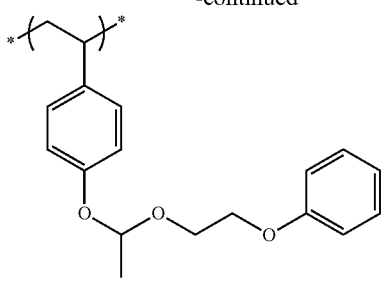
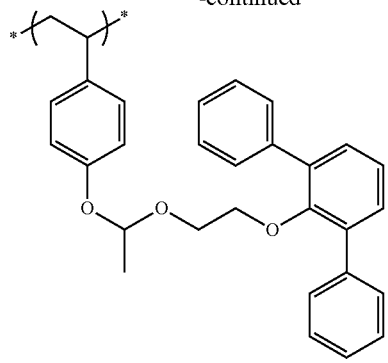
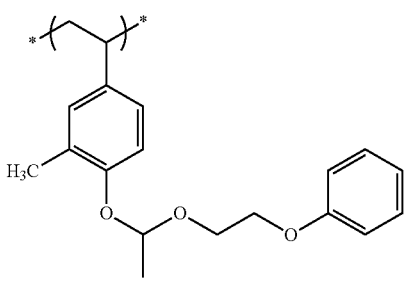
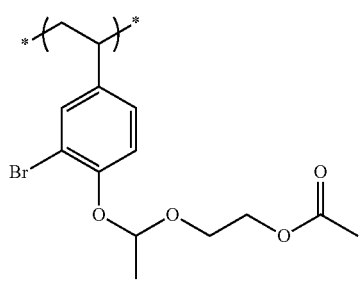
[Chem. 19]
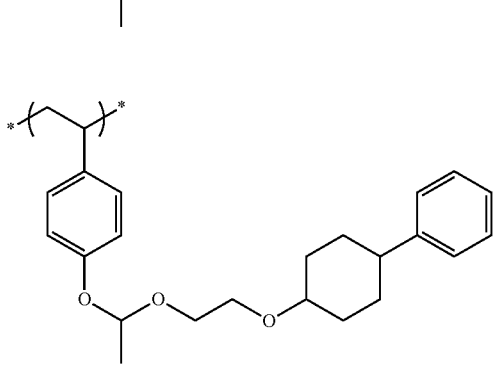
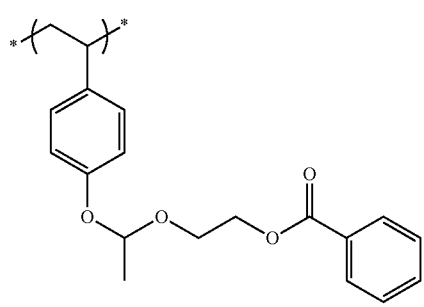
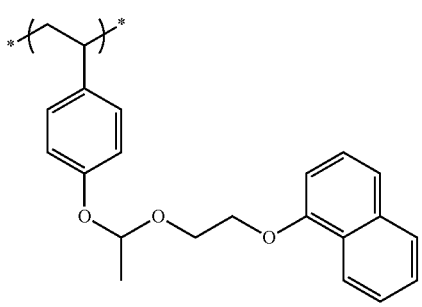
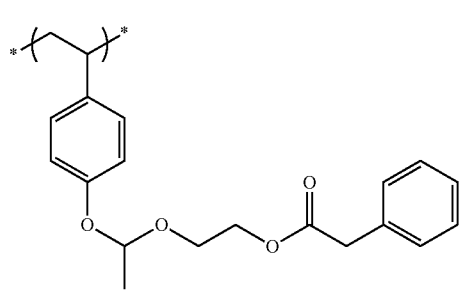

53
-continued
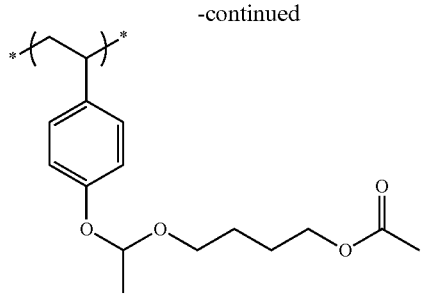
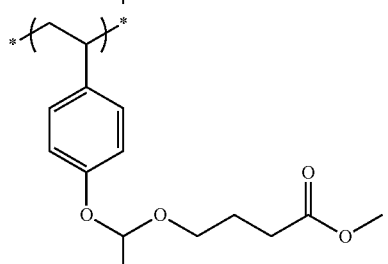
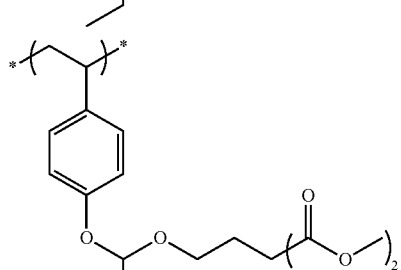
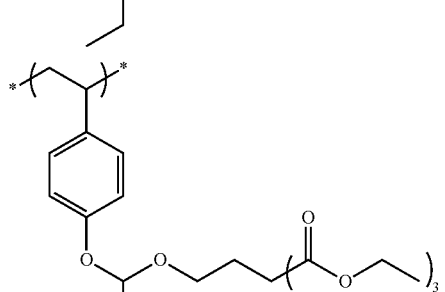
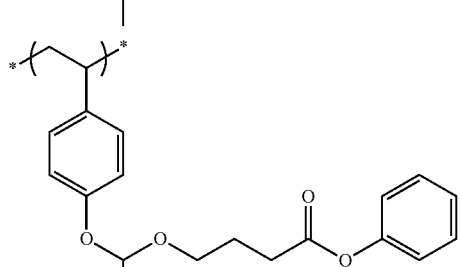
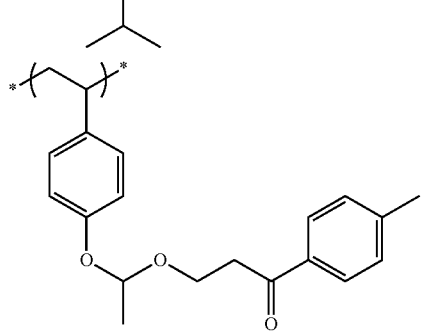
54
-continued
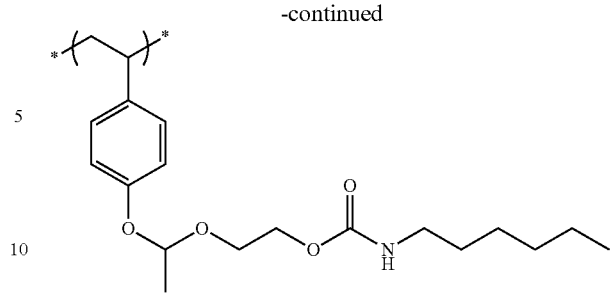
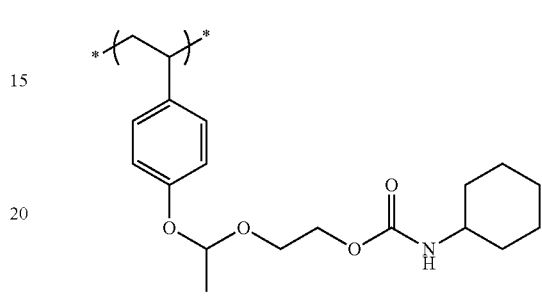
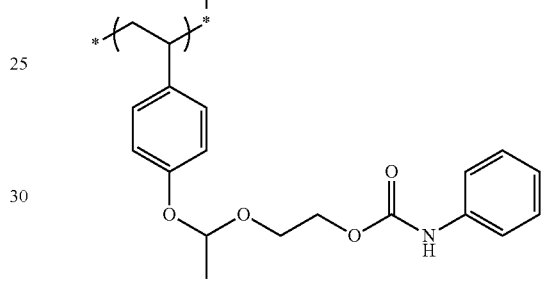
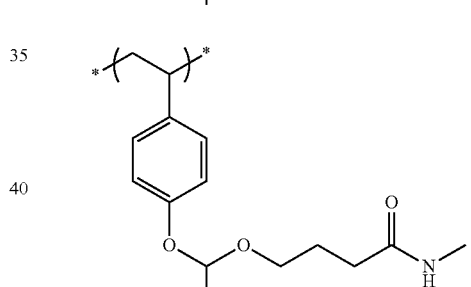
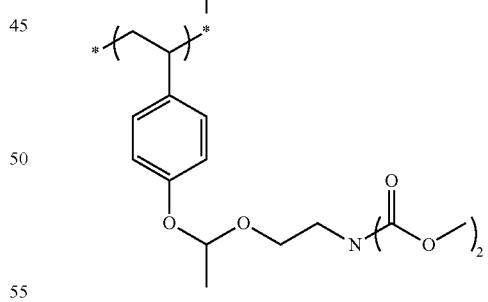
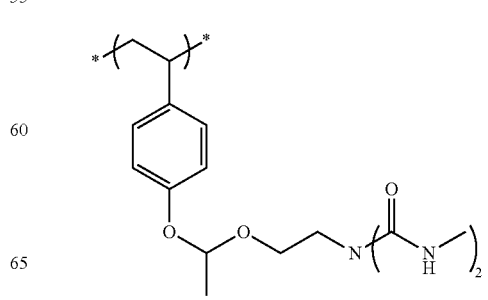

55
-continued
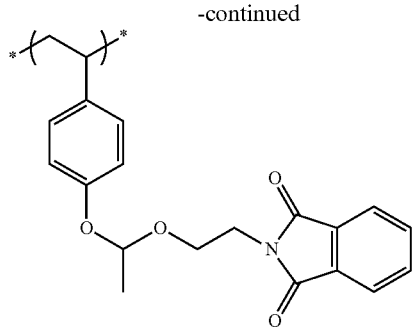
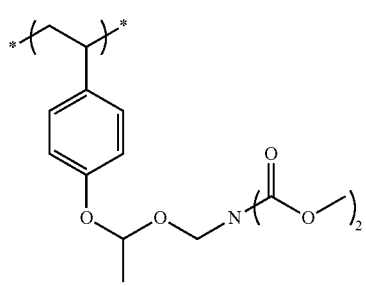
[Chem. 20]
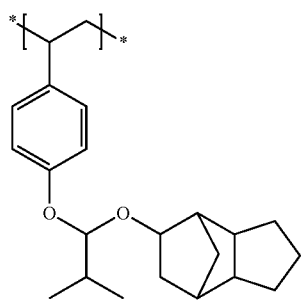
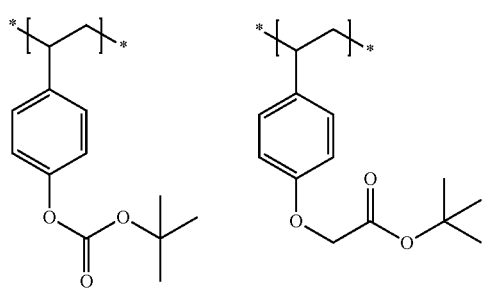
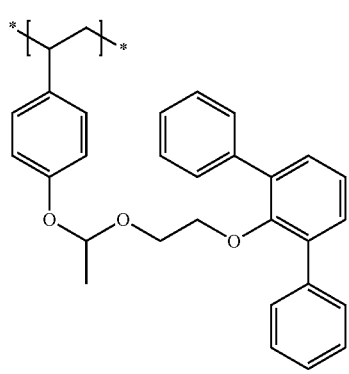
56
-continued
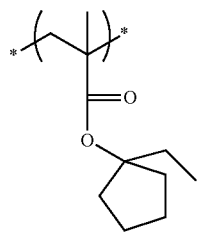
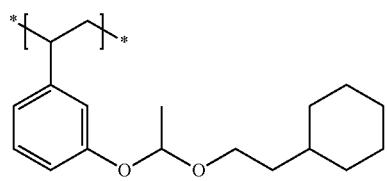
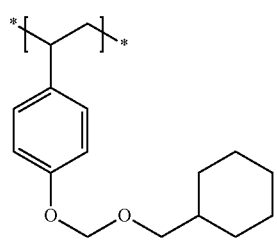
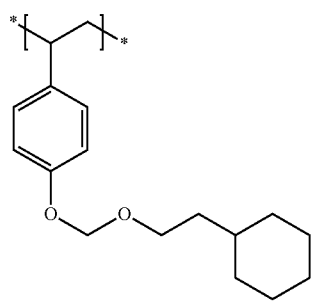
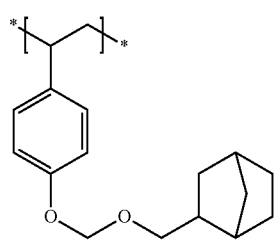
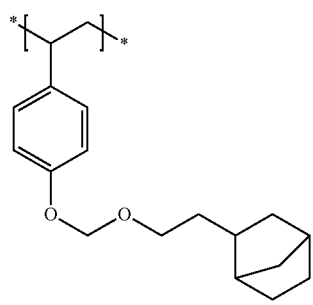

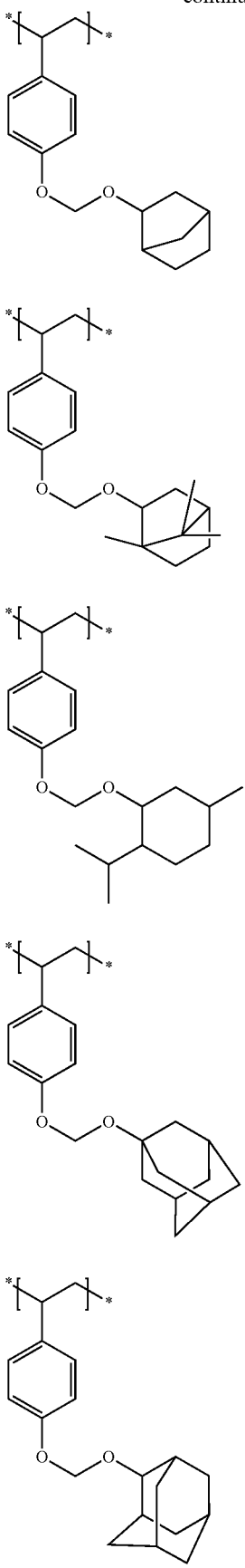

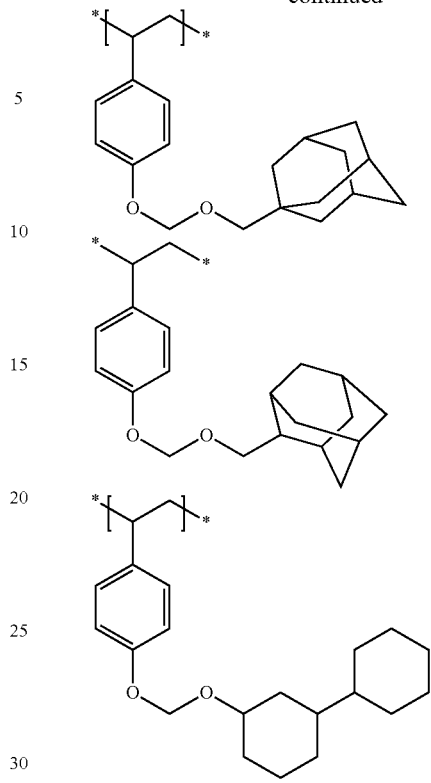

The content of the repeating units represented by Formula (A) in the resin (C) preferably ranges from 10 mol % to 90 mol %, more preferably from 10 mol % to 70 mol % and particularly preferably from 20 mol % to 60 mol %, based on the total of repeating units.

The resin (C) may contain a repeating unit represented by Formula (X) below as a repeating unit having an acid-decomposable group.

[Chem. 21]

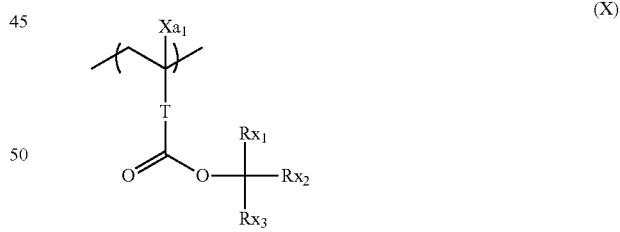

(X)

In Formula (X), $Xa_1$ represents a hydrogen atom, a methyl group, a trifluoromethyl group or a hydroxymethyl group.

T represents a single bond or a divalent linking group.

Each of $Rx_1$ to $Rx_3$ independently may be a linear or branched alkyl group or a monocyclic or polycyclic cycloalkyl group. At least two of $Rx_1$ to $Rx_3$ may be bound to each other to form a monocyclic or polycyclic cycloalkyl group.

As for the divalent linking group as T, for example, an alkylene group, —(COO-Rt)- and —(O-Rt)- may be exemplified. Here, Rt represents an alkylene group or a cycloalkylene group.

T preferably represents a single bond or —(COO-Rt)—. Here, Rt is preferably an alkylene group having 1 to 5 carbon atoms, and is more preferably —CH$_2$—, —(CH$_2$)$_2$— or —(CH$_2$)$_3$—.

The alkyl group as for Rx$_1$ to Rx$_3$ is preferably an alkyl group having 1 to 4 carbon atoms such as a methyl group, an ethyl group, a n-propyl group, an isopropyl group, a n-butyl group, an isobutyl group and a t-butyl group.

The cycloalkyl group as for Rx$_1$ to Rx$_3$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group and an adamantyl group.

As for the cycloalkyl group which may be formed by a bond of two of R$_{x1}$ to R$_{x3}$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferred. A monocyclic cycloalkyl group having 5 to 6 carbon atoms is particularly preferred.

Particularly, an aspect in which Rx$_1$ is a methyl group or an ethyl group, and Rx$_2$ and Rx$_3$ are bound to each other to form the above described cycloalkyl group is preferred.

Each of the groups described above may have a substituent, and as for the substituent, for example, an alkyl group (1 to 4 carbon atoms), a halogen atom, a hydroxyl group, an alkoxy group (1 to 4 carbon atoms), a carboxyl group, an alkoxycarbonyl group (2 to 6 carbon atoms) may be exemplified, and a group having 8 or less carbon atoms is preferred.

Specific examples of the repeating unit having an acid-decomposable group are described below, but the present invention is not limited thereto.

[Chem. 22]

1
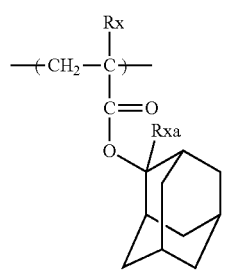

2
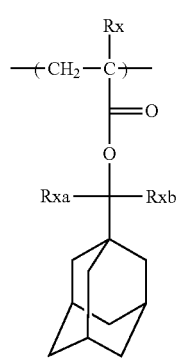

3
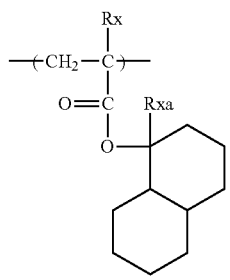

4
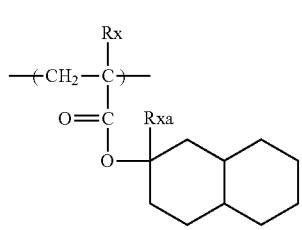

5
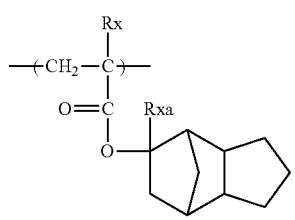

6
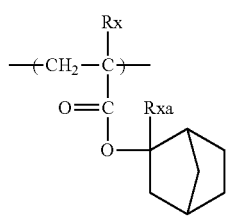

7
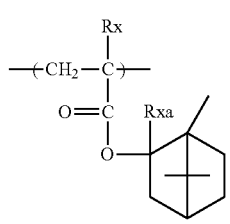

8
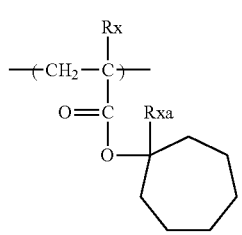

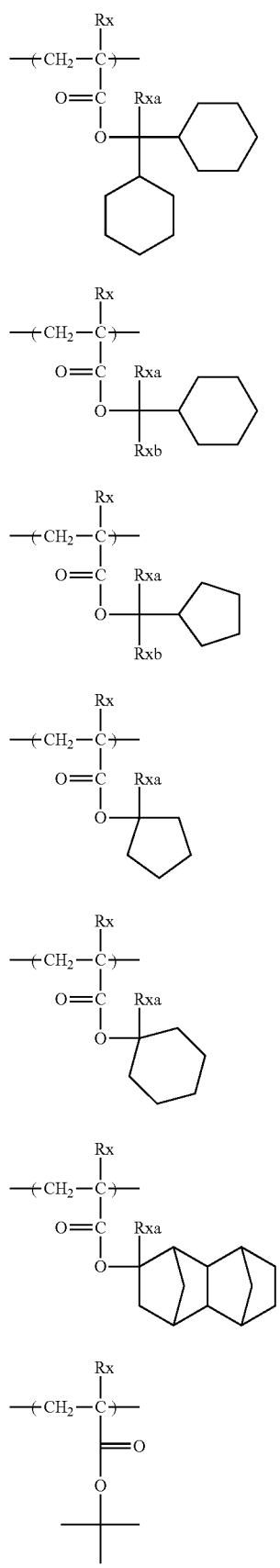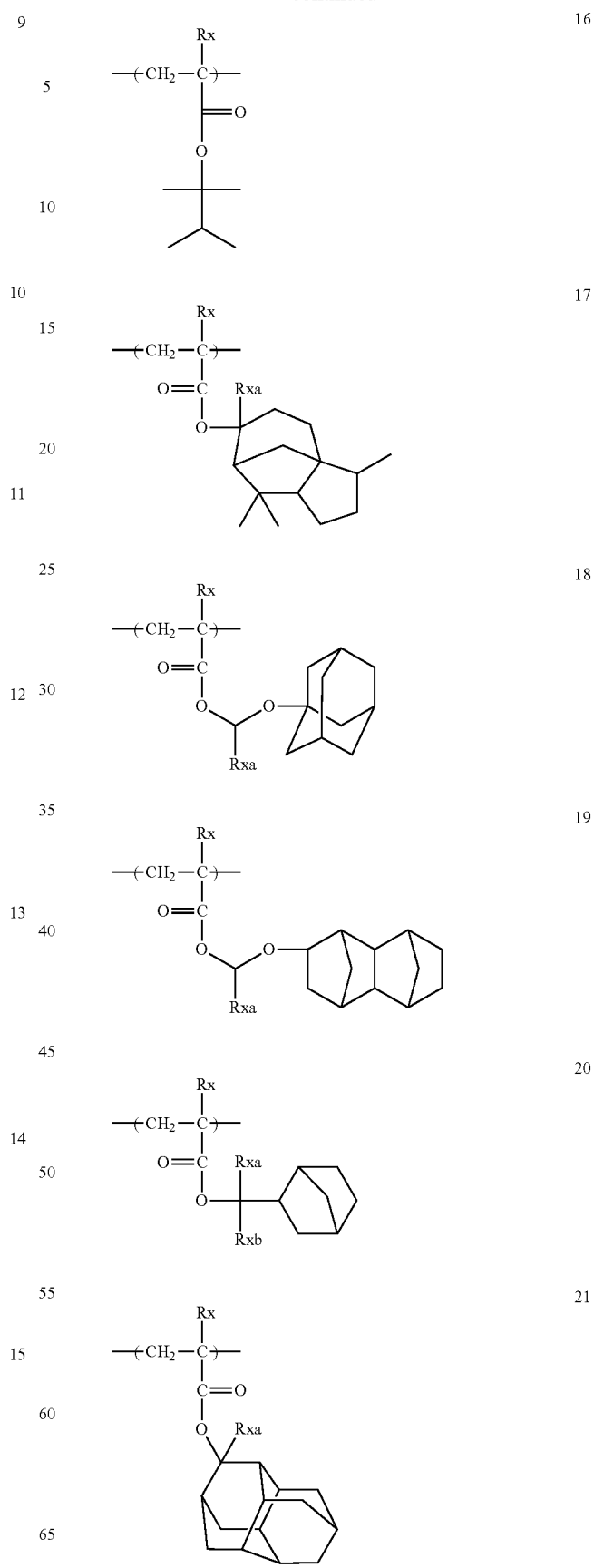

-continued

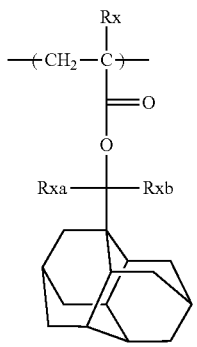
22

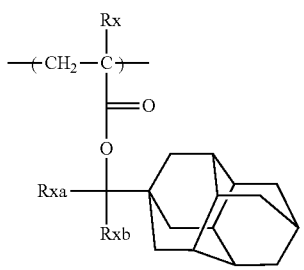
23

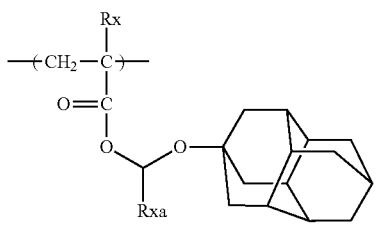
24

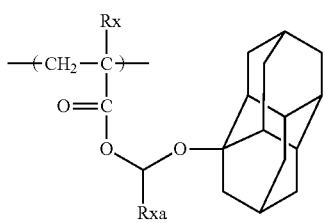
25

(In formula, Rx is H, CH$_3$, CF$_3$, or CH$_2$OH, and each of Rxa and Rxb is an alkyl group having 1 to 4 carbon atoms)

The content of the repeating units represented by Formula (X) in the resin preferably ranges from 3 mol % to 90 mol %, more preferably from 5 mol % to 80 mol % and particularly preferably from 7 mol % to 70 mol %, based on the total of repeating units.

The content of the group capable of decomposing by an acid is calculated by formula B/(B+S) using the number (B) of groups capable of decomposing by an acid in the resin and the number (S) of alkali-soluble groups not protected by a group capable of leaving by an acid. The content preferably ranges from 0.01 to 0.7, more preferably from 0.05 to 0.50, and still more preferably from 0.05 to 0.40.

The resin (C) preferably has a repeating unit represented by Formula (2) below.

[Chem. 23]

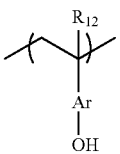
(2)

In Formula (2), R$_{12}$ represents a hydrogen atom or a methyl group.

Ar represents an aromatic ring.

R$_{12}$ represents a hydrogen atom or a methyl group, and a hydrogen atom is preferred in view of developability.

The aromatic ring of Ar is a monocyclic or polycyclic aromatic ring, and an aromatic hydrocarbon ring having 6 to 18 carbon atoms, such as a benzene ring, a naphthalene ring, an anthracene ring, a fluorene ring, and a phenanthrene ring, or an aromatic heterocyclic ring including a hetero ring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring, may be exemplified. Among them, a benzene ring, and a naphthalene ring are preferred in view of resolution, and a benzene ring is the most preferred in view of sensitivity.

The aromatic ring of Ar may have a substituent other than the group represented by —OH, and as for the substituent, for example, an alkyl group, a cycloalkyl group, a halogen atom, a hydroxyl group, an alkoxy group, a carboxyl group, an alkoxy carbonyl group, an alkylcarbonyl group, an alkylcarbonyloxy group, an alkylsulfonyloxy group, and an arylcarbonyl group may be exemplified.

As for the repeating unit represented by Formula (2), a repeating unit derived from hydroxystyrene (that is, a repeating unit in which R$_{12}$ is a hydrogen atom, and Ar is a benzene ring in Formula (2)) is preferred in view of sensitivity.

The content of the repeating units represented by Formula (2) preferably ranges from 10 mol % to 90 mol %, more preferably from 20 mol % to 85 mol % and still more preferably from 30 mol % to 85 mol % based on the total of repeating units of the resin (C).

Hereinafter, examples of the repeating unit represented by Formula (2) will be described, but are not limited thereto.

[Chem. 24]

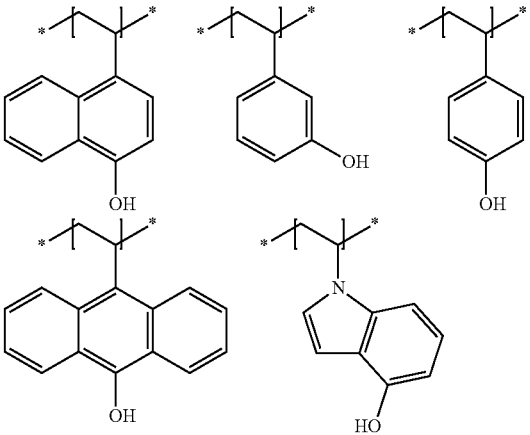

-continued
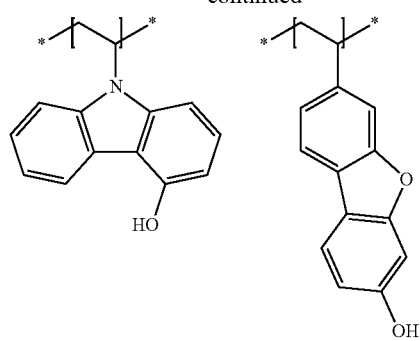
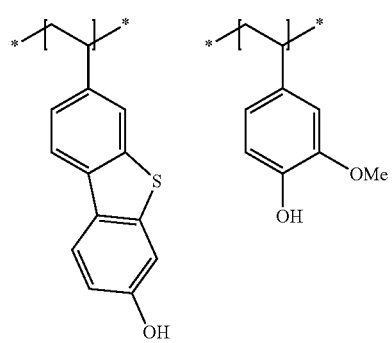
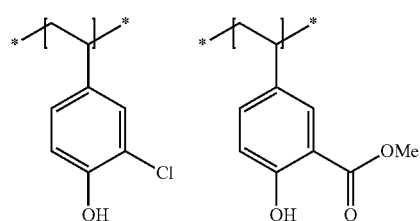
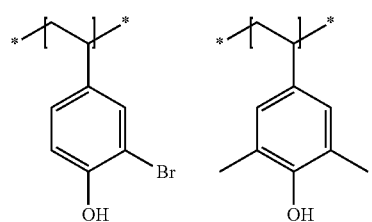
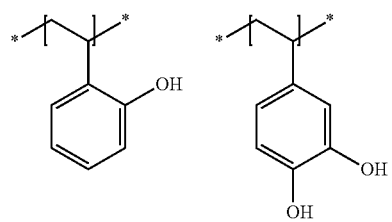
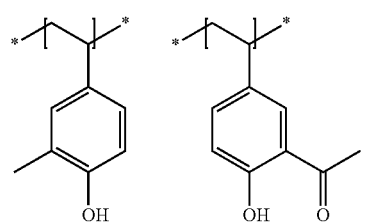
-continued
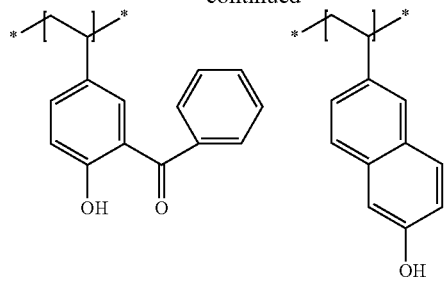
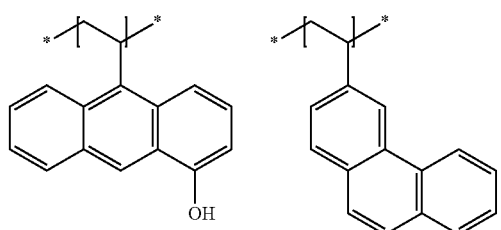
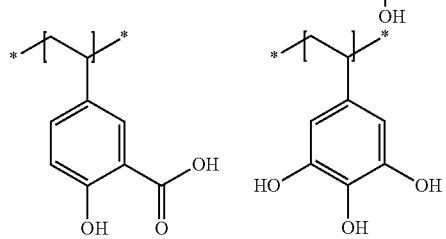
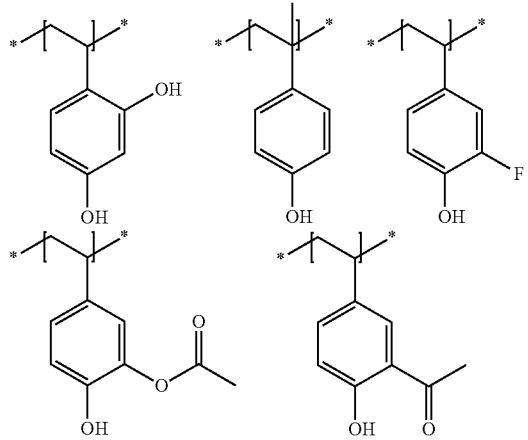
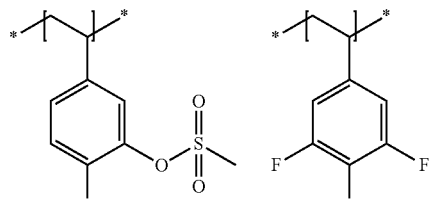
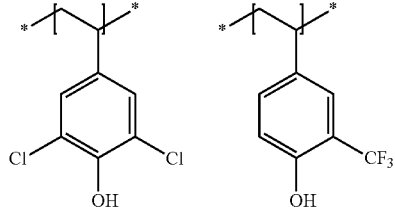

-continued

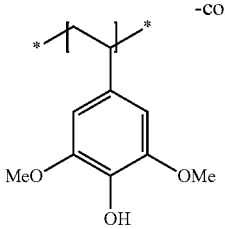

In the case where ArF excimer laser light is irradiated on the composition of the present invention, the resin preferably has a monocyclic or polycyclic alicyclic hydrocarbon structure. Meanwhile, hereinafter, such a resin is referred to as an "alicyclic hydrocarbon-based acid-decomposable resin."

As for the alicyclic hydrocarbon-based acid-decomposable resin, a resin which contains at least one kind selected from the group consisting of repeating units having alicyclic hydrocarbon-containing partial structures as represented by Formulas (pI) to (pV) below and a repeating unit represented by Formula (II-AB) below is preferred.

[Chem. 25]

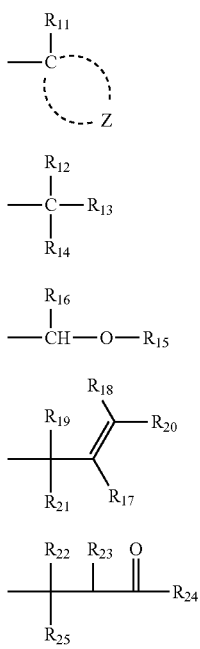

(pI)
(pII)
(pIII)
(pIV)
(pV)

In Formulas (pI) to (pV), $R^{11}$ represents a methyl group, an ethyl group, a n-propyl group, an isopropyl group, a n-butyl group, an isobutyl group or a sec-butyl group, and Z represents an atomic group required for forming a cycloalkyl group together with the carbon atom.

Each of $R_{12}$ to $R_{16}$ independently represents a linear or branched alkyl or cycloalkyl group having 1 to 4 carbon atoms. Meanwhile, at least one of $R_{12}$ to $R_{14}$ represents a cycloalkyl group. Any one of $R_{15}$ and $R_{16}$ represents a cycloalkyl group.

Each of $R_{17}$ to $R_{21}$ independently represents a hydrogen atom or a linear or branched alkyl or cycloalkyl group having 1 to 4 carbon atoms. Meanwhile, at least one of $R_{17}$ to $R_{21}$ represents a cycloalkyl group. Any one of $R_{19}$ and $R_{21}$ represents a linear or branched alkyl or cycloalkyl group having 1 to 4 carbon atoms.

Each of $R_{22}$ to $R_{25}$ independently represents a hydrogen atom or a linear or branched alkyl or cycloalkyl group having 1 to 4 carbon atoms. Meanwhile, at least one of $R_{22}$ to $R_{25}$ represents a cycloalkyl group. Meanwhile, $R_{23}$ and $R_{24}$ may be bound to each other to form a ring structure.

[Chem. 26]

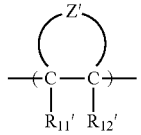

(II-AB)

In Formula (II-AB), each of $R_{11}'$ and $R_{12}'$ independently represents a hydrogen atom, a cyano group, a halogen atom or an alkyl group.

Z' represents an atomic group required for forming an alicyclic structure together with two bonded carbon atoms (C—C).

Also, Formula (II-AB) above is more preferably Formula (II-AB1) or Formula (II-AB2) below.

[Chem. 27]

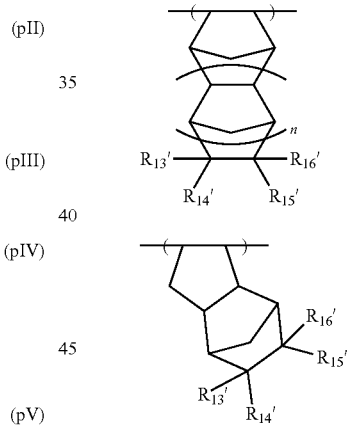

(II-AB1)

(II-AB2)

In Formulas (II-AB1) and (II-AB2), each of $R_{13}'$ to $R_{16}'$ independently represents a hydrogen atom, a halogen atom, a cyano group, a hydroxyl group, —COOH, —COOR$_5$, a group capable of decomposing by the action of an acid, —C(=O)—X-A'-R$_{17}'$, an alkyl group or a cycloalkyl group. Here, $R_5$ represents an alkyl group, a cycloalkyl group or a group having a lactone structure. X represents an oxygen atom, a sulfur atom, —NH—, —NHSO$_2$— or —NHSO$_2$NH—. A' represents a single bond or a divalent linking group. $R_{17}'$ represents —COOH, —COOR$_5$, —CN, a hydroxyl group, an alkoxy group, —CO—NH—R$_6$, —CO—NH—SO$_2$—R$_6$ or a group having a lactone structure. Here, $R_6$ represents an alkyl group or a cycloalkyl group. Meanwhile, at least two of $R_{13}'$ to $R_{16}'$ may be bound to each other to form a ring structure.

n represents 0 or 1.

In Formulas (pI) to (pV), in $R_{12}$ to $R_{25}$, the alkyl group is preferably a linear or branched alkyl group having 1 to 4 carbon atoms, and for example, a methyl group, an ethyl group, a propyl group, a n-butyl group, a sec-butyl group, and a t-butyl group may be exemplified.

The cycloalkyl group in $R_{12}$ to $R_{25}$, or the cycloalkyl group formed by Z and carbon atoms may be a monocyclic cycloalkyl group, or a polycyclic cycloalkyl group. Specifically, a group of a monocyclo, bicyclo, tricyclo or tetracyclo structure, which has 5 or more carbon atoms, may be exemplified. The number of carbon atoms preferably ranges from 6 to 30, and particularly preferably from 7 to 25.

As a preferred cycloalkyl group, for example, an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, and a cyclodecanyl group and a cyclododecanyl group may be exemplified. More preferably, an adamantyl group, a norbornyl group, a cyclohexyl group, a cyclopentyl group, a tetracyclododecanyl group and a tricyclodecanyl group may be exemplified.

Each of the alkyl group and the cycloalkyl group may have a substituent. As for the substituent, for example, an alkyl group (1 to 4 carbon atoms), a halogen atom, a hydroxyl group, an alkoxy group (1 to 4 carbon atoms), a carboxyl group, and an alkoxycarbonyl group (2 to 6 carbon atoms) may be exemplified. These substituents may further have substituents. As for further substituents, for example, a hydroxyl group, a halogen atom and an alkoxy group may be exemplified.

The structures represented by Formulas (pI) to (pV) may be used for protecting an alkali-soluble group. As for the alkali-soluble group, various groups known in this technical field may be exemplified.

Specifically, for example, a structure in which a hydrogen atom of a carboxylic acid group, a sulfonic acid group, a phenol group and a thiol group is substituted with structures represented by Formulas (pI) to (pV) may be exemplified. Preferably, a structure in which a hydrogen atom of a carboxylic acid group or a sulfonic acid group is substituted with structures represented by Formulas (pI) to (pV) may be exemplified.

As for the repeating unit having the alkali-soluble group protected by the structures represented by Formulas (pI) to (pV), a repeating unit represented by Formula (pA) below is preferred.

[Chem. 28]

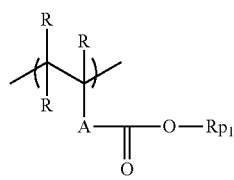

(pA)

In Formula (pA),

R represents a hydrogen atom, a halogen atom, or a linear or branched alkyl group having 1 to 4 carbon atoms. Each of a plurality of R's may be the same or different.

A is selected from the group consisting of a single bond, an alkylene group, an ether group, a thioether group, a carbonyl group, an ester group, an amide group, a sulfonamide group, an urethane group, an urea group and a combination of two or more thereof, and is preferably a single bond.

$Rp_1$ is a group represented by any one of Formulas (pI) to (pV) above.

The repeating unit represented by Formula (pA) is most preferably a repeating unit by 2-alkyl-2-adamantyl (meth)acrylate or dialkyl(1-adamantyl)methyl(meth)acrylate.

Specific examples of the repeating unit represented by Formula (pA) may be the same as those exemplified as above as the repeating unit represented by Formula (X), and other specific examples of the repeating unit represented by Formula (pA) will be described below.

[Chem. 29]

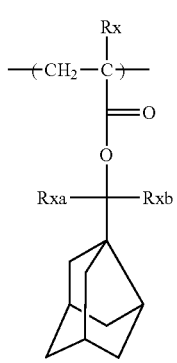

1

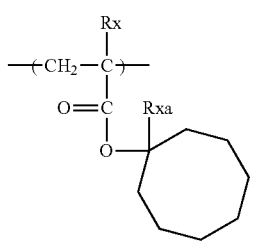

2

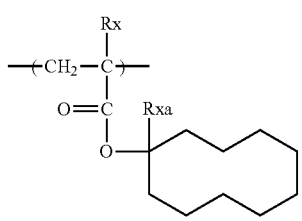

3

In each structural formula above, Rx represents H, $CH_3$, $CF_3$ or $CH_2OH$, and each of Rxa and Rxb independently represents an alkyl group having 1 to 4 carbon atoms.

The halogen atom as $R_{11}'$ or $R_{12}'$ in Formula (II-AB) is, for example, a chlorine atom, a bromine atom, a fluorine atom or an iodine atom.

As for the alkyl group as $R_{11}'$ or $R_{12}'$, a linear or branched alkyl group having 1 to 10 carbon atoms is preferred, and for example, a methyl group, an ethyl group, a n-propyl group, an isopropyl group, a linear or branched butyl group, a pentyl group, a hexyl group, and a heptyl group may be exemplified.

The atomic group represented by Z' is an atomic group which forms a repeating unit of an alicyclic hydrocarbon which may have a substituent in the resin. As for the atomic group, a group capable of forming a repeating unit of a bridged alicyclic hydrocarbon is preferred.

As for the skeleton of the formed alicyclic hydrocarbon, the same as that in the cycloalkyl group of $R_{12}$ to $R_{25}$ in Formulas (pI) to (pVI) may be exemplified.

The skeleton of the alicyclic hydrocarbon may have a substituent. As for the substituent, for example, $R_{13}'$ to $R_{16}'$ in Formulas (II-AB1) and (II-AB2) above may be exemplified.

In the alicyclic hydrocarbon-based acid-decomposable resin, a group capable of decomposing by the action of an acid may be contained in at least one of a repeating unit having an alicyclic hydrocarbon-containing partial structure as represented by Formulas (pI) to (pV) above, a repeating unit represented by Formula (II-AB), and a repeating unit of a copolymerization component as described below.

In Formulas (II-AB1) and (II-AB2) above, each substituent in $R_{13}'$ to $R_{16}'$ may also be a substituent of an atomic group Z' for forming an alicyclic structure or a bridged alicyclic structure in Formula (II-AB) above.

As for the repeating unit represented by Formula (II-AB1) or Formula (II-AB2) above, the specific examples will be described below, but the present invention is not limited thereto.

[Chem. 30]

[II-1]
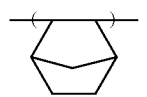

[II-2]
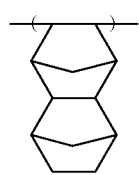

[II-3]
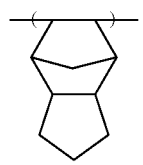

[II-4]
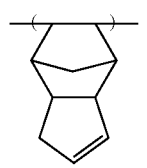

[II-5]
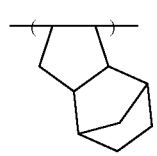

[II-6]
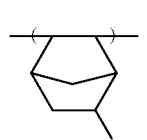

[II-7]
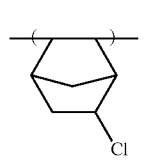

-continued

[II-8]
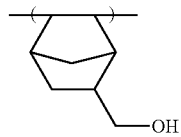

[II-9]
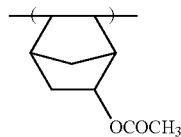

[II-10]
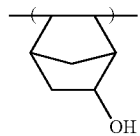

[II-11]
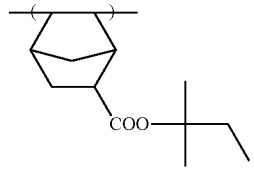

[II-12]
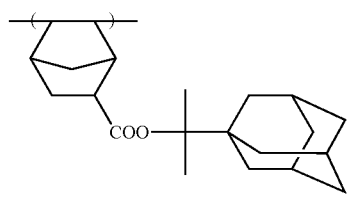

[II-13]
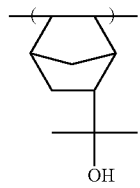

[II-14]
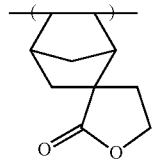

[II-15]
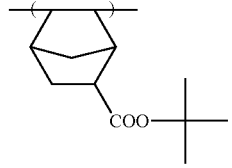

[II-16]
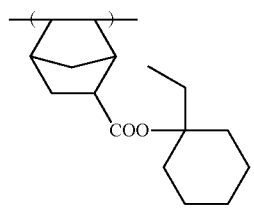

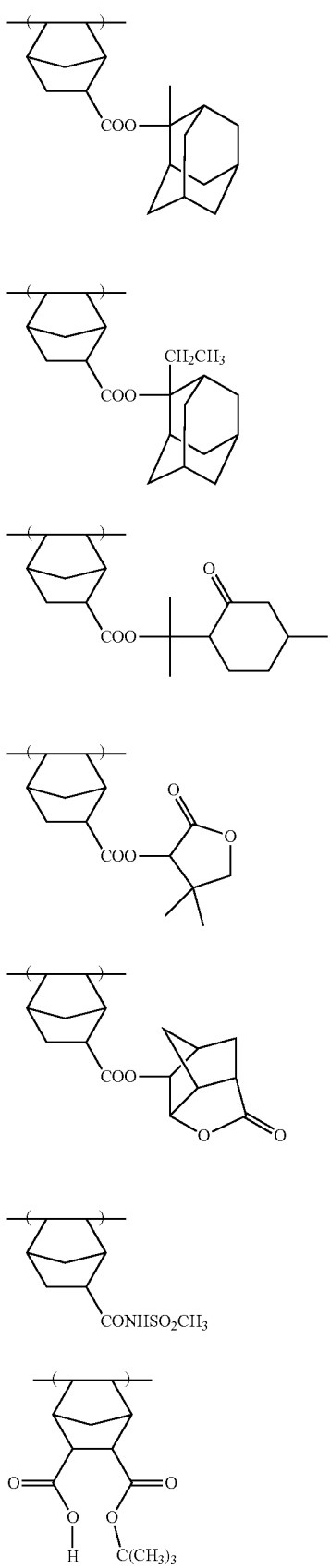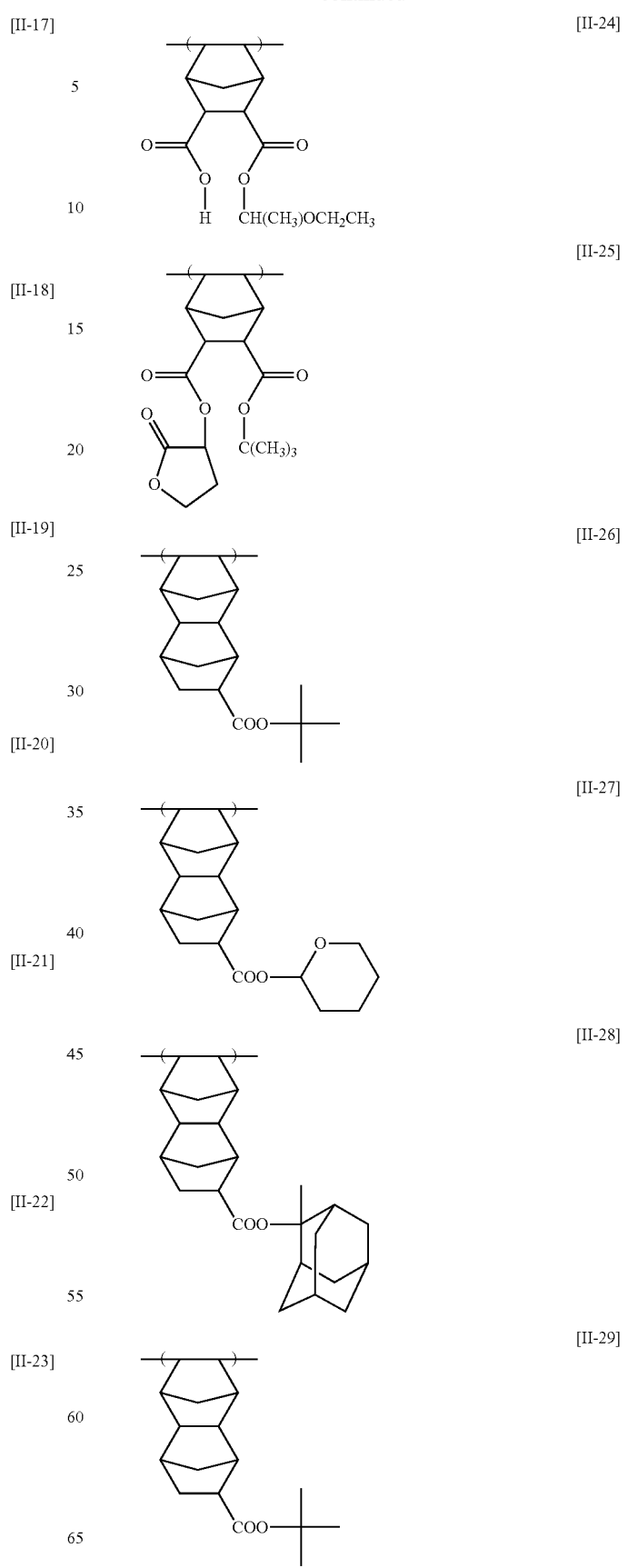

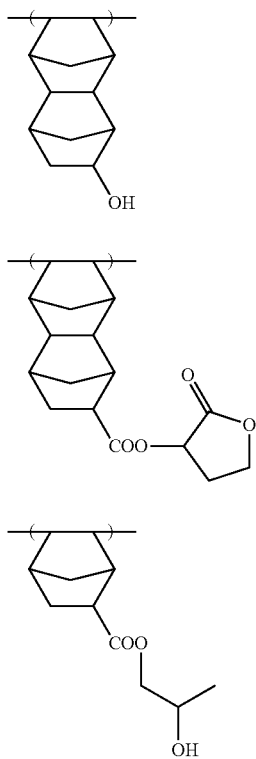

The resin (C) preferably has a repeating unit containing a lactone group. The lactone group is preferably a group having a 5 to 7 membered ring lactone structure, and particularly preferably, another ring structure is condensed to the 5 to 7 membered ring lactone structure so as to form a bicyclo structure or a spiro structure.

More preferably, the resin (C) contains a repeating unit having a group containing a lactone structure represented by any one of Formulas (LC1-1) to (LC1-17) below. Meanwhile, the group having the lactone structure may be directly bonded to a main chain. As a preferred lactone structure, (LC1-1), (LC1-4), (LC1-5), (LC1-6), (LC1-13), (LC1-14) and (LC1-17) may be exemplified. By using a specific lactone structure, line edge roughness and development defect may be further reduced.

[Chem. 31]

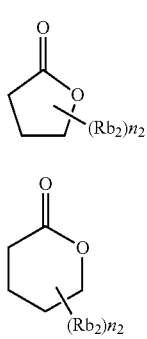

LC1-1

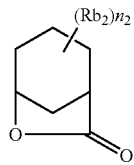

LC1-2

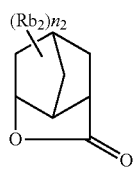

LC1-3

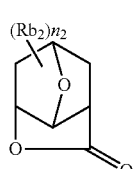

LC1-4

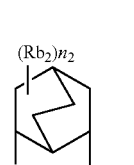

LC1-5

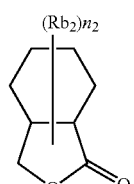

LC1-6

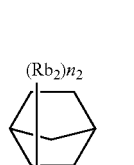

LC1-7

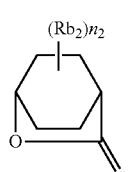

LC1-8

LC1-9

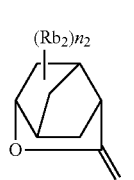

LC1-10

-continued

LC1-11
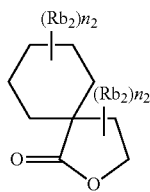

LC1-12
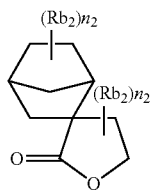

LC1-13
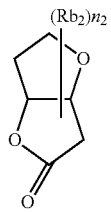

LC1-14
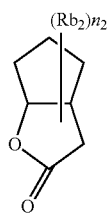

LC1-15

LC1-16
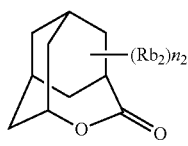

LC1-17
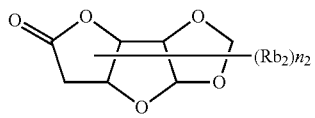

The lactone structure moiety may or may not have a substituent ($Rb_2$). As for a preferred substituent ($Rb_2$), for example, an alkyl group having 1 to 8 carbon atoms, a cycloalkyl group having 3 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group and an acid-decomposable group may be exemplified.

$n_2$ represents an integer of 0 to 4. When $n_2$ is an integer of 2 or more, a plurality of $Rb_2$'s may be the same or different. Also, in this case, the plurality of $Rb_2$'s may be bound to each other to form a ring structure.

As for a repeating unit having a group containing a lactone structure represented by any one of Formulas (LC1-1) to (LC1-17), for example, any one of $R_{13}'$ to $R_{16}'$ in Formulas (II-AB1) and (II-AB2) above which has a group represented by Formulas (LC1-1) to (LC1-17) and a repeating unit represented by Formula (AI) below may be exemplified. Meanwhile, as for the former example, a structure in which, $R_5$ of —$COOR_5$ is a group represented by Formulas (LC1-1) to (LC1-17) may be exemplified.

[Chem. 32]

(AI)

In Formula (AI), $Rb_0$ represents a hydrogen atom, a halogen atom, or an alkyl group having 1 to 4 carbon atoms.

The alkyl group as $Rb_0$ is, for example, a methyl group, an ethyl group, a propyl group, a n-butyl group, a sec-butyl group or a t-butyl group. These alkyl groups may have substituents. As for the substituents, for example, a hydroxyl group and a halogen atom may be exemplified.

As for the halogen atom of $Rb_0$, a fluorine atom, a chlorine atom, a bromine atom and an iodine atom may be exemplified.

$Rb_0$ is preferably a hydrogen atom or a methyl group.

Ab represents an alkylene group, a divalent linking group having a monocyclic or polycyclic alicyclic hydrocarbon structure, single bond, an ether group, an ester group, a carbonyl group, or a combination thereof. Ab is preferably a single bond or a linking group represented by -$Ab_1$-$CO_2$—.

$Ab_1$ is a linear or branched alkylene group, or a monocyclic or polycyclic cycloalkylene group, and is preferably a methylene group, an ethylene group, a cyclohexylene group, an adamantylene group or a norbornylene group.

V is a group represented by any one of Formulas (LC1-1) to (LC1-17).

Meanwhile, in the repeating unit having a lactone structure, an optical isomer is generally present, and any optical isomer may be used. Also, one kind of optical isomer may be used alone, or a plurality of optical isomers may be used as a mixture. When one kind of optical isomer is mainly used, the optical purity is preferably 90% ee or more, and more preferably 95% ee or more.

Particularly preferably, as for the repeating unit having a lactone group, the following repeating units may be exemplified. By selecting an optimum lactone group, a pattern profile and an iso/dense bias may be improved. In Formulas, Rx and R represent H, $CH_3$, $CH_2OH$ or $CF_3$.

[Chem. 33]

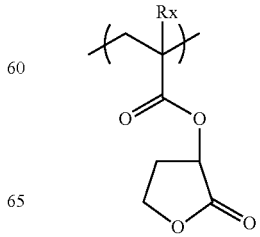

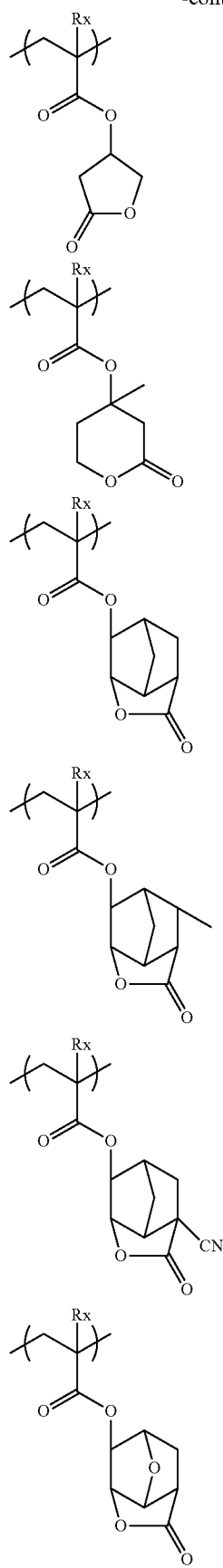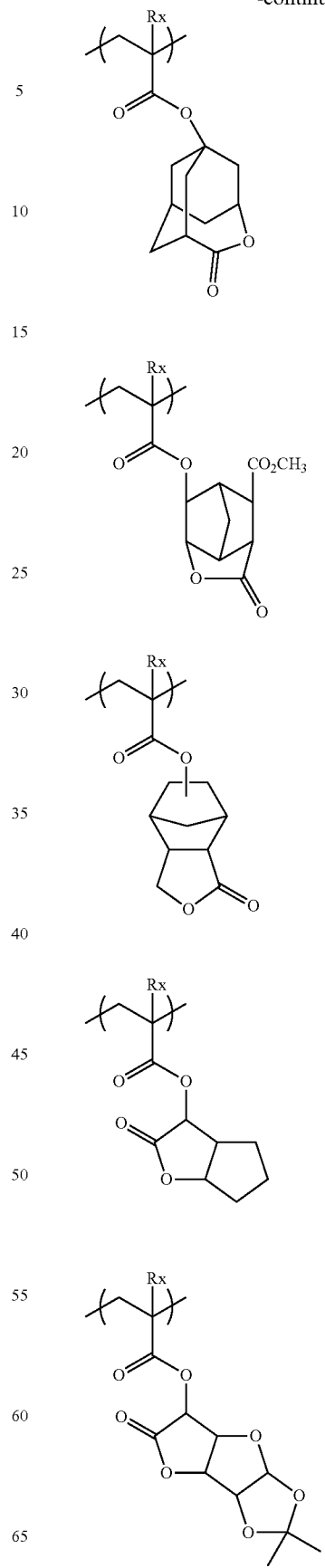

-continued
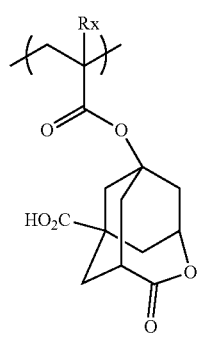
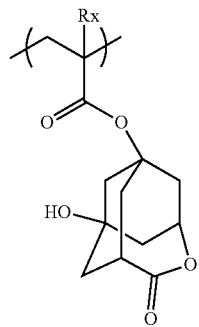
[Chem. 34]
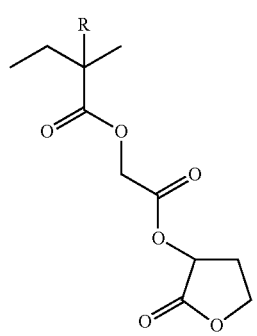
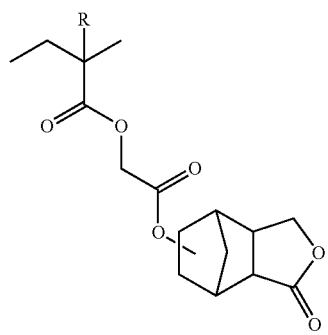
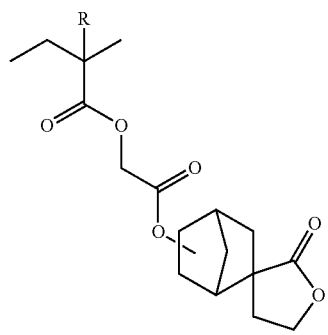
-continued
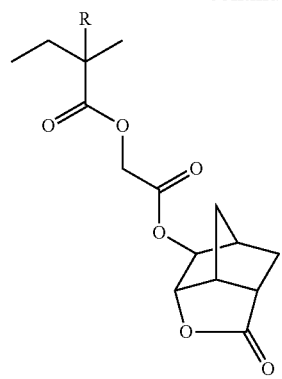
[Chem. 35]
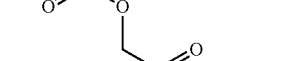
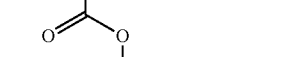

83
-continued
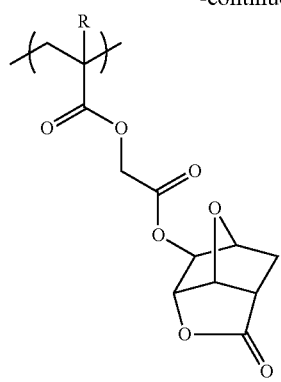
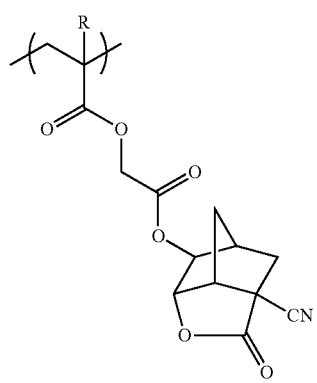
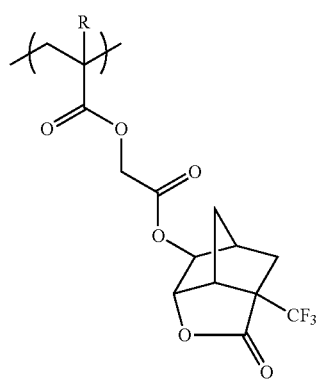
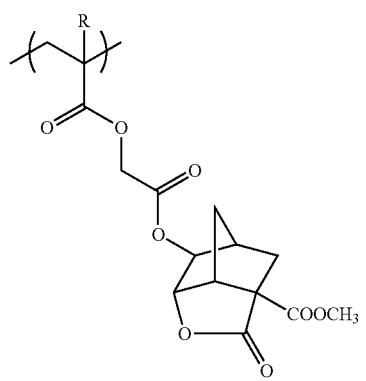
84
-continued
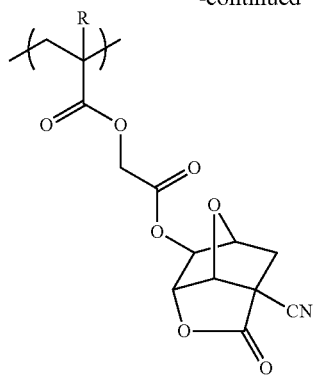
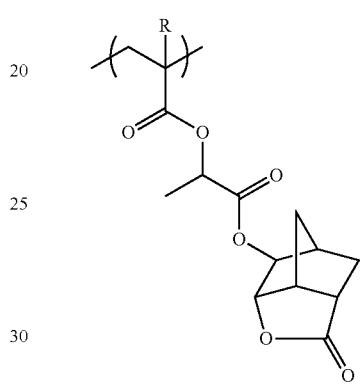
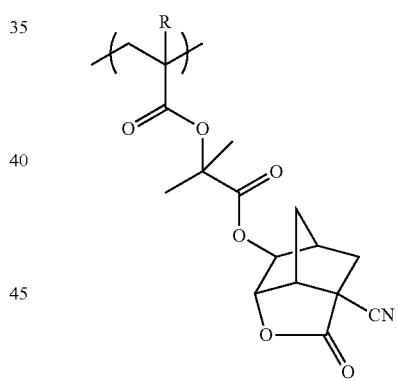
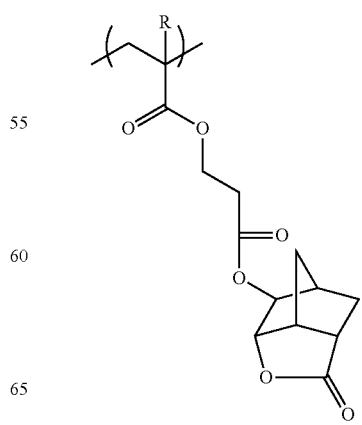

85
-continued
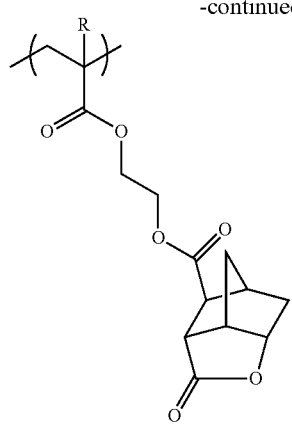
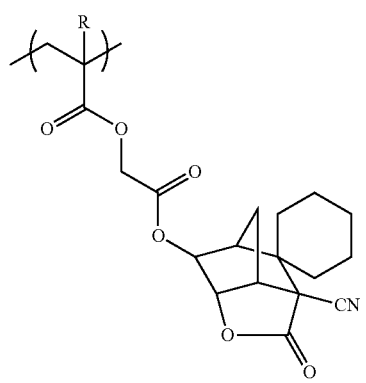
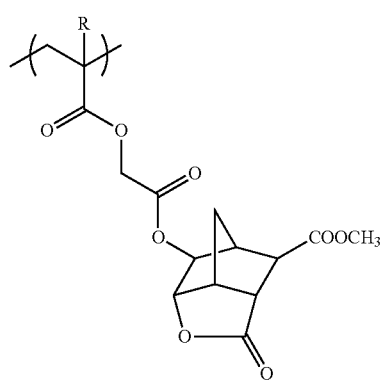
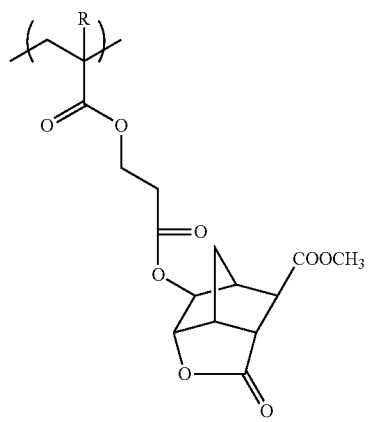
86
-continued
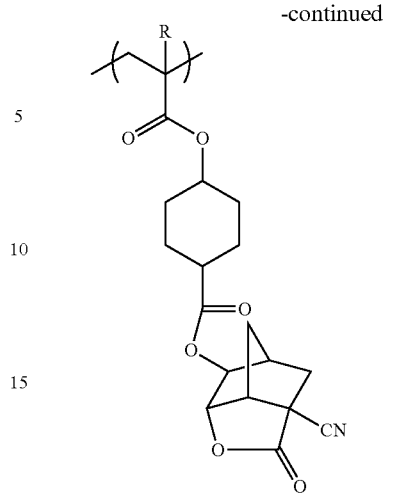
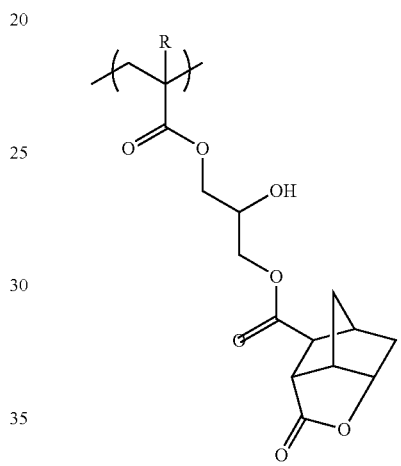
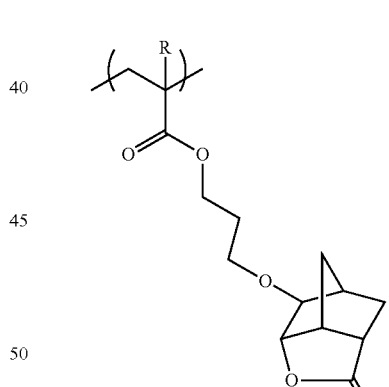
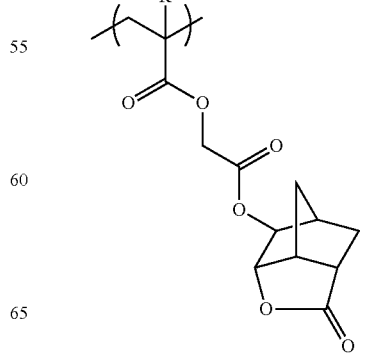

The resin (C) may contain a plurality of repeating units including lactone groups. In this case, preferably, either (1) two repeating units having a single bond and -Ab$_1$-CO$_2$— as Abs, respectively, in Formula (AI), or (2) two repeating units each of which has only -Ab$_1$-CO$_2$— as Ab in Formula (AI) may be exemplified.

The content of the repeating unit containing a lactone group (a total of repeating units containing a plurality of lactone groups) preferably ranges from 3 mol % to 70 mol % and more preferably from 5 mol % to 60 mol % based on the total of repeating units of the resin (C).

The resin (C) preferably has a repeating unit containing an alicyclic hydrocarbon structure substituted with a polar group. This may improve the adhesion to a substrate and the developer affinity. As for the polar group, a hydroxyl group or a cyano group is preferable. Meanwhile, the hydroxyl group as the polar group forms an alcoholic hydroxyl group.

As for the alicyclic hydrocarbon structure substituted with the polar group, for example, the structure represented by Formula (VIIa) or (VIIb) below may be exemplified.

[Chem. 36]

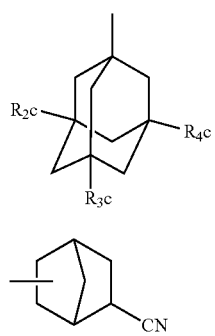

(VIIa)

(VIIb)

In Formula (VIIa), each of R$_2$c to R$_4$c independently represents a hydrogen atom, a hydroxyl group or a cyano group. Meanwhile, at least one of R$_2$c to R$_4$c represents a hydroxyl group or a cyano group. Preferably, one or two of R$_2$c to R$_4$c is(are) a hydroxyl group(s), and the rest are(is) hydrogen atoms. More preferably, two of R$_2$c to R$_4$c are hydroxyl groups, and the rest is a hydrogen atom.

The group represented by Formula (VIIa) is preferably a dihydroxy body or a monohydroxy body, and more preferably a dihydroxy body.

As for a repeating unit having a group represented by Formula (VIIa) or (VIIb), at least one of R$_{13}$' to R$_{16}$' in Formula (II-AB1) or (II-AB2) above which has a group represented by Formula (VIIa) or (VIIb) above, and a repeating unit represented by Formula (AIIa) or (AIIb) below may be exemplified. As for the former example, a structure in which R$_5$ of —COOR$_5$ is a group represented by Formula (VIIa) or (VIIb) may be exemplified.

[Chem. 37]

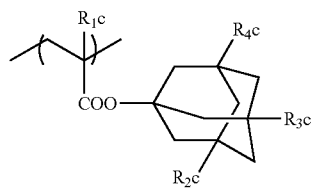

(AIIa)

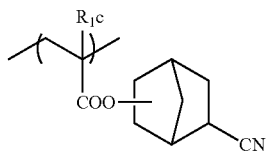

(AIIb)

In Formulas (AIIa) and (AIIb),

R$_1$c represents a hydrogen atom, a methyl group, a trifluoromethyl group or a hydroxymethyl group.

R$_2$c to R$_4$c are the same as R$_2$c to R$_4$c in Formula (VIIa).

Specific examples of the repeating unit represented by Formula (AIIa) or (AIIb) will be described below, but the present invention is not limited thereto.

[Chem. 38]

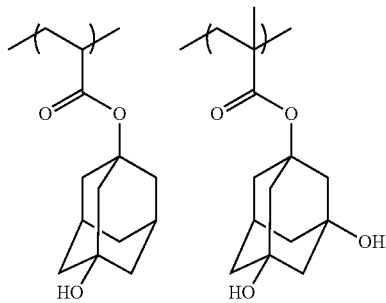

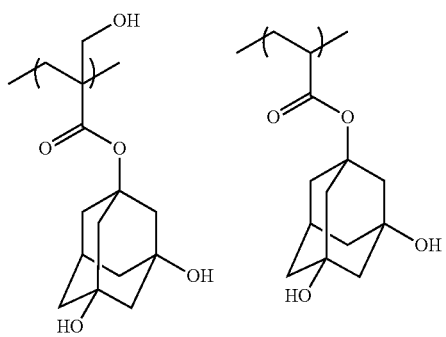

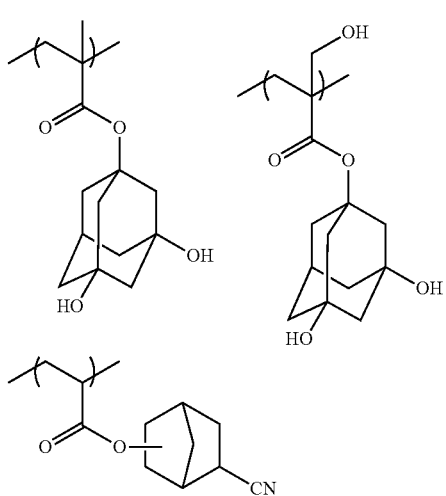

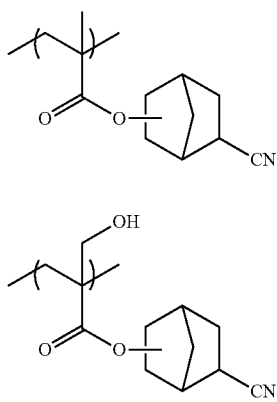

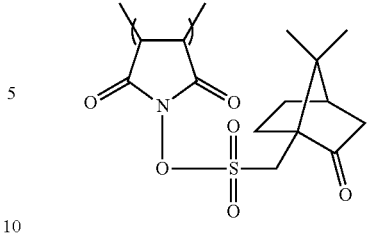

The resin (C) may or may not contain the repeating unit described above. However, when the repeating unit is contained, the content of the repeating unit (or the total of a plurality of corresponding repeating units) preferably ranges from 3 mol % to 30 mol %, and more preferably from 5 mol % to 25 mol % based on the total of repeating units of the resin.

The resin (C) may have a repeating unit represented by Formula (VIII) below.

[Chem. 39]

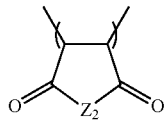

(VIII)

In Formula (VIII), $Z_2$ represents —O— or —N($R^{41}$)—. $R_{41}$ represents a hydrogen atom, a hydroxyl group, an alkyl group or —$OSO_2$—$R_{42}$. Here, $R^{42}$ represents an alkyl group, a cycloalkyl group or a camphor residue. The alkyl group as $R_{41}$ or $R_{42}$ may be substituted by, for example, a halogen atom. In this case, as for the halogen atom, a fluorine atom is preferred.

Specific examples of the repeating unit represented by Formula (VIII) will be described below, but the present invention is not limited thereto.

[Chem. 40]

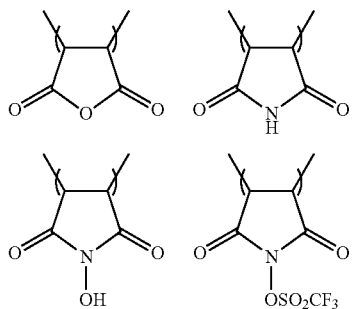

The resin (C) preferably has a repeating unit containing an alkali-soluble group, and more preferably a repeating unit containing a carboxyl group. This may improve the resolution in the use for a contact hole.

As for the repeating unit containing a carboxyl group, both a repeating unit having a carboxyl group directly bonded to a main chain of a resin, and a repeating unit having a carboxyl group bonded to a main chain of a resin through a linking group are preferred.

As for the former example, a repeating unit by an acrylic acid or a methacrylic acid may be exemplified. In the latter example, the linking group may have a monocyclic or polycyclic cycloalkyl structure.

As for the repeating unit containing a carboxyl group, a repeating unit by an acrylic acid or a methacrylic acid is the most preferred.

A mass-average molecular weight of the resin capable of decomposing by the action of an acid to increase the solubility in an alkali developer, in terms of polystyrene obtained through GPC, preferably ranges from 2,000 to 200,000. When the mass-average molecular weight is 2,000 or more, it is possible to particularly improve the heat resistance and the dry etching resistance. When the mass-average molecular weight is 200,000 or less, the developability may be particularly improved, and at the same time, the film forming property may also be improved due to the lowering of the viscosity of a composition.

A more preferred molecular weight ranges from 2,500 to 50,000, and more preferably from 3,000 to 20,000. In the fine pattern formation using electron beam, X-rays, or high-energy beam having a wavelength of 50 nm or less (e.g., EUV), it is the most preferred that the mass-average molecular weight ranges from 3,000 to 10,000. By adjusting the molecular weight, it is possible to achieve the improvement of the heat resistance and resolution of the composition as well as the reduction of the development defect.

The polydispersity (Mw/Mn) of the resin capable of decomposing by the action of an acid to increase the solubility in an alkali developer preferably ranges from 1.0 to 3.0, more preferably from 1.2 to 2.5, and still more preferably from 1.2 to 1.6. By adjusting the polydispersity, for example, a ling edge roughness performance may be improved.

Specific examples of the resin described above will be described below, but the present invention is not limited thereto.

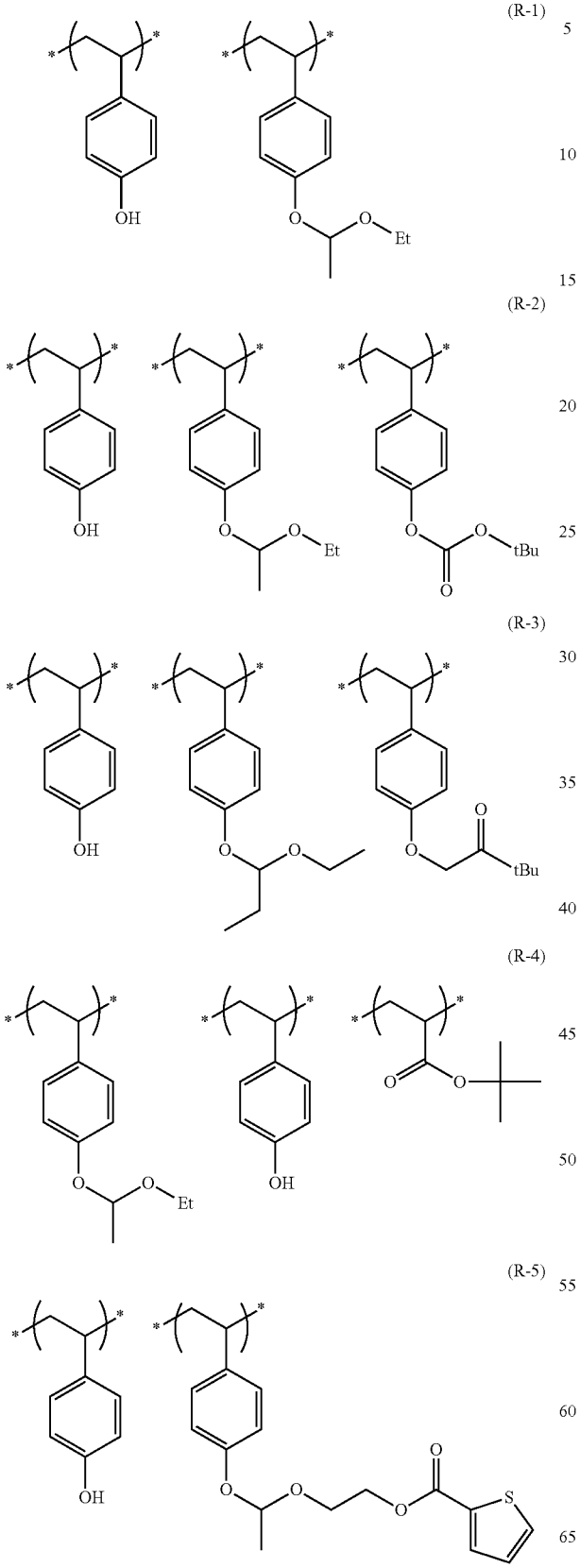

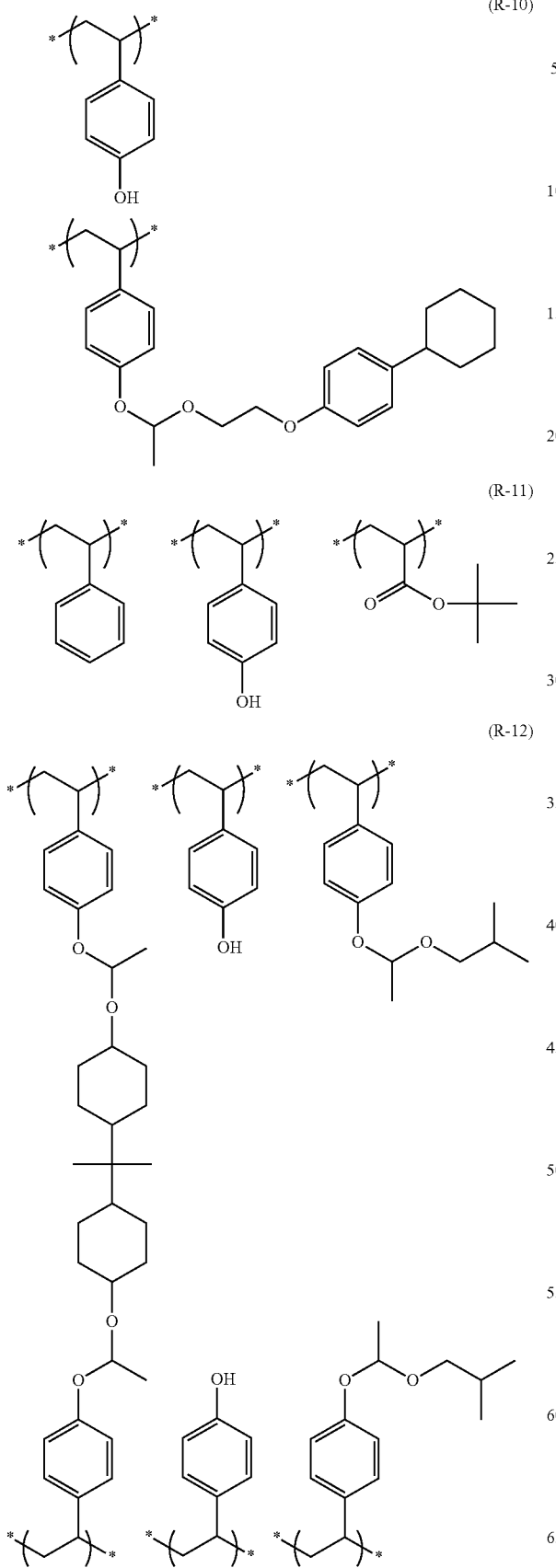
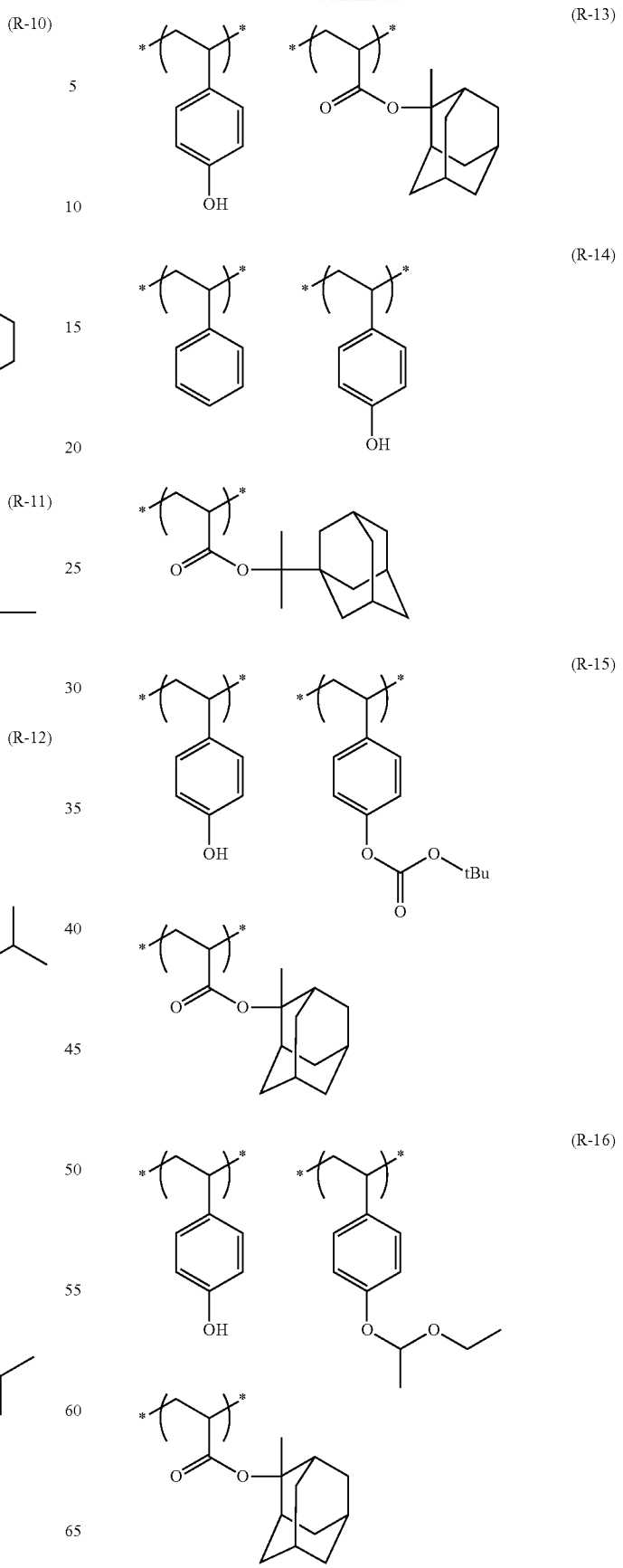

(R-17)
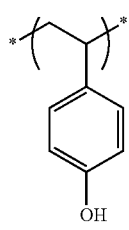 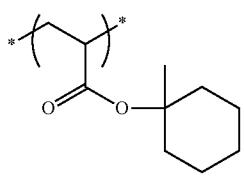
[Chem. 42]
(R-18)
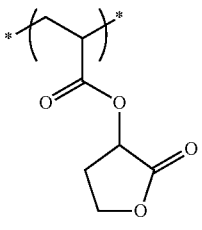
[Chem. 43]
R-22
(R-19)
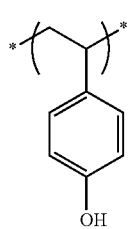 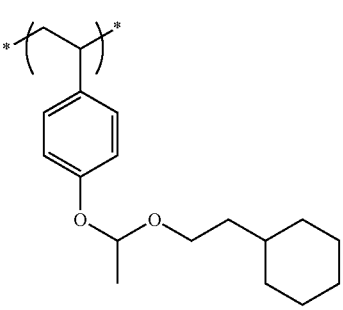
R-23
(R-20)
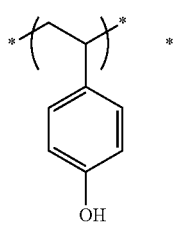 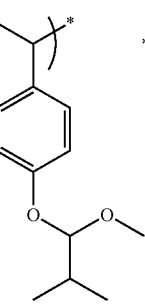 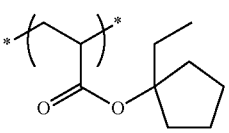
R-24
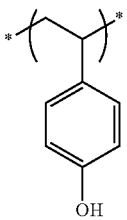 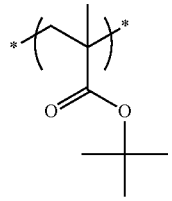
R-25
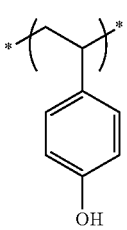 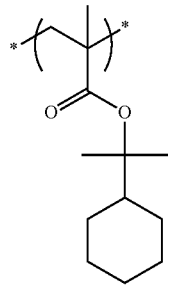
(R-21)
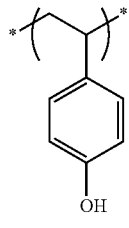 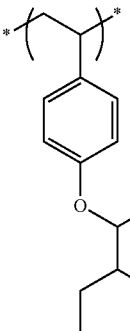 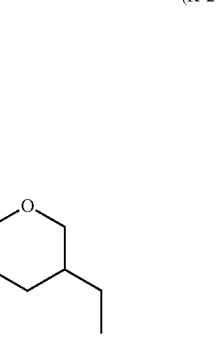
R-26
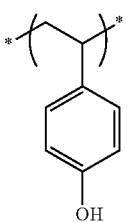 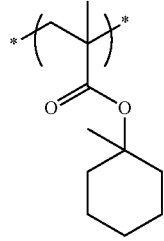
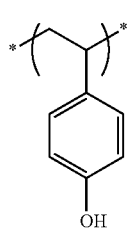 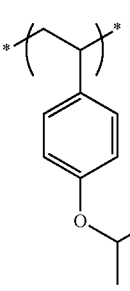 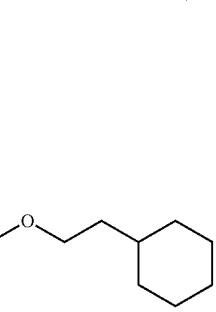
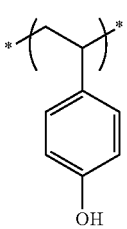 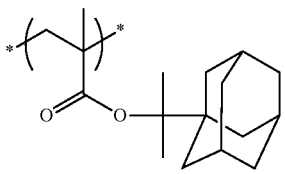

-continued

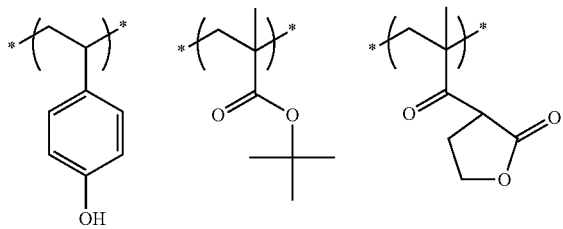

R-27

In the specific examples, tBu represents a t-butyl group.

The resin (C) may be used either alone or in combination of two or more kinds thereof.

The blending ratio of the resin (C) in the composition according to the present invention preferably ranges from 5% to 99.9% by mass, more preferably from 50% to 95% by mass, and still more preferably from 60% to 93% by mass based on the total solid content.

The chemical amplification resist composition of the present invention may also be used in a process where after coating, film formation, and exposure, a development is performed using a developer mainly containing an organic solvent to obtain a negative-type pattern. As for such a process, for example, a process described in Japanese Patent Application Laid-Open No. 2010-217884 may be used.

As for the developer mainly containing an organic solvent, polar solvents, such as ester solvents (e.g., butyl acetate, ethyl acetate), ketone solvents (e.g., 2-heptanone, cyclohexanone), alcohol solvents, amide solvents, ether solvents, and hydrocarbon solvents may be used. The water content of the developer mainly containing an organic solvent is preferably less than 10% by mass, and more preferably, the developer contains substantially no moisture.

[4] (E) Compound Having Phenolic Hydroxyl Group

The chemical amplification resist composition of the present invention preferably contains a compound (E) having a phenolic hydroxyl group (hereinafter, also referred to as a compound (E)) when forming a negative-type pattern.

The phenolic hydroxyl group in this specification refers to a group formed by substituting a hydrogen atom of an aromatic ring group with a hydroxyl group. The aromatic ring of the aromatic ring group is a monocyclic or polycyclic aromatic ring, and a benzene ring or a naphthalene ring may be exemplified.

According to the chemical amplification resist composition of the present invention, at the exposed portion, by the action of an acid generated from a compound (B) capable of generating an acid upon irradiation with an actinic ray or radiation, or the action of a sulfonic acid generated from the compound (A) represented by Formula (I) by the action of an acid, a crosslinking reaction between the phenolic hydroxyl group-containing compound (E) and a crosslinking agent (D) described below is performed to form a negative-type pattern.

Here, the compound (E) is a compound having a solubility which decreases in an organic solvent-containing developer when the reaction between the compound (E) and the crosslinking agent (D) described below is performed by the action of an acid generated from the acid generator described above.

Also, the compound (E) is a resin having a solubility which decreases in an alkali developer when the reaction between the compound (E) and the crosslinking agent (D) described below is performed by the action of an acid generated from the acid generator described above.

The phenolic hydroxyl group-containing compound (E) is not particularly limited as long as it has a phenolic hydroxyl group, and may be a compound having a relatively low molecular weight such as a molecular resist, or a polymer compound. Meanwhile, as for the molecular resist, for example, a low-molecular-weight cyclic polyphenol compound described in Japanese Patent Application Laid-Open Nos. 2009-173623 and 2009-173625 may be used.

The phenolic hydroxyl group-containing compound (E) is preferably a polymer compound in view of the reactivity and sensitivity.

When the phenolic hydroxyl group-containing compound (E) of the present invention is a polymer compound, the polymer compound preferably contains a repeating unit having at least one kind of phenolic hydroxyl group. The repeating unit having the phenolic hydroxyl group is not particularly limited, but the repeating unit represented by Formula (1) below is preferred.

[Chem. 44]

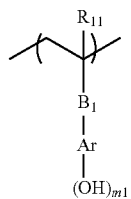

(1)

In Formula (1), $R_{11}$ represents a hydrogen atom, a methyl group which may have a substituent, or a halogen atom.

$B_1$ represents a single bond or a divalent linking group.

Ar represents an aromatic ring.

m1 represents an integer of 1 or more.

As for the methyl group which may have a substituent, in $R^{11}$, a trifluoromethyl group, or a hydroxymethyl group may be exemplified.

$R^{11}$ is preferably a hydrogen atom or a methyl group, and a hydrogen atom is preferred in view of developability.

As for the divalent linking group of $B_1$, a carbonyl group, an alkylene group (preferably having 1 to 10 carbon atoms, and more preferably having 1 to 5 carbon atoms), a sulfonyl group (—S(=O)$_2$—), —O—, —NH— or a divalent linking group having a combination thereof is preferred.

$B_1$ preferably represents a single bond, a carbonyloxy group (—C(=O)—O—) or —C(=O)—NH—, more preferably a single bond or a carbonyloxy (—C(=O)—O—), and particularly preferably a single bond in view of improvement of dry etching resistance.

The aromatic ring of Ar is a monocyclic or polycyclic aromatic ring, and examples thereof may include an aromatic hydrocarbon ring which may have a substituent having 6 to 18 carbon atoms, such as a benzene ring, a naphthalene ring, an anthracene ring, a fluorene ring, and a phenanthrene ring, or an aromatic heterocyclic ring including a hetero ring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Among them, a benzene ring, and a naphthalene ring are preferred in view of resolution, and a benzene ring is the most preferred in view of sensitivity.

m1 is preferably an integer of 1 to 5, and most preferably 1. When m1 is 1, and Ar is a benzene ring, the substitution position of —OH may be a para position, a meta position or an ortho position with respect to the binding position with $B_1$ of a benzene ring (or a polymer backbone when $B_1$ is a single bond), but in view of crosslinking reactivity, a para position and a meta position are preferred, and a para position is more preferred.

The aromatic ring of Ar may have a substituent other than the group represented by —OH, and as for the substituent, for example, an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkylsulfonyloxy group, and an arylcarbonyl group may be exemplified.

As for the repeating unit having a phenolic hydroxyl group, the repeating unit represented by Formula (2) below is preferred in view of the crosslinking reactivity, developability, and dry etching resistance.

[Chem. 45]

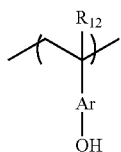

(2)

In Formula (2), $R_{12}$ represents a hydrogen atom or a methyl group.

Ar represents an aromatic ring.

$R_{12}$ represents a hydrogen atom or a methyl group, and the hydrogen atom is preferred in view of the developability.

Ar in Formula (2) is the same as Ar in Formula (1), and its preferred range is also the same as that in Formula (1). As for the repeating unit represented by Formula (2), a repeating unit derived from hydroxystyrene (that is, a repeating unit of Formula (2) in which $R_{12}$ is a hydrogen atom and Ar is a benzene ring) is preferred in view of the sensitivity.

The compound (E) as for the polymer compound may be constituted by only the above described repeating unit having a phenolic hydroxyl group. The compound (E) as for the polymer compound may have a repeating unit as described below as well as the above described repeating unit having a phenolic hydroxyl group. in this case, the content of the repeating unit having a phenolic hydroxyl group preferably ranges from 10 mol % to 98 mol %, more preferably from 30 mol % to 97 mol % and still more preferably from 40 mol % to 95 mol % based on the total of repeating units of the compound (E) as for the polymer compound. Accordingly, particularly, when the resist film is a thin film (for example, a resist film thickness ranging from 10 nm to 150 nm), it is possible to more securely reduce the dissolution rate of an exposed portion of the resist film of the present invention, which is formed using the compound (E), in the alkali developer (that is, it is possible to more securely control the dissolution resist of the resist film employing the compound (E) to an optimum level). As a result, the sensitivity may be more securely improved.

Hereinafter, the examples of the repeating unit having a phenolic hydroxyl group will be described below, but are not limited thereto.

[Chem. 46]

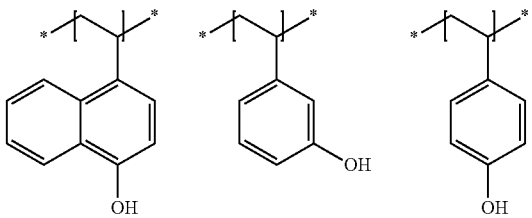

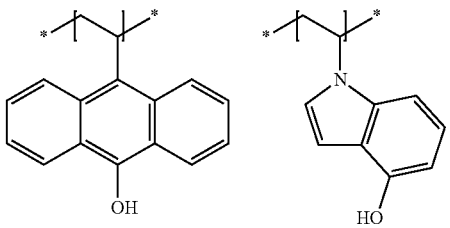

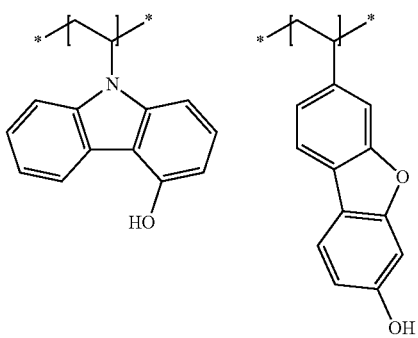

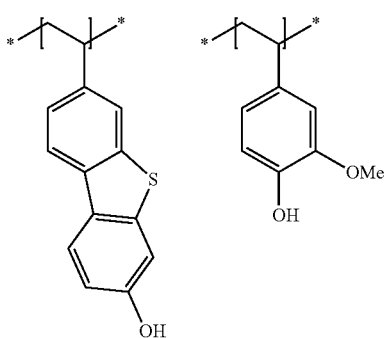

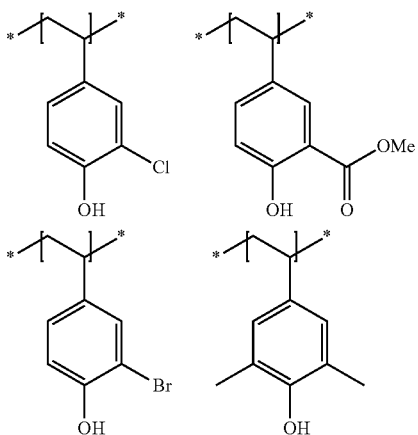

101
-continued
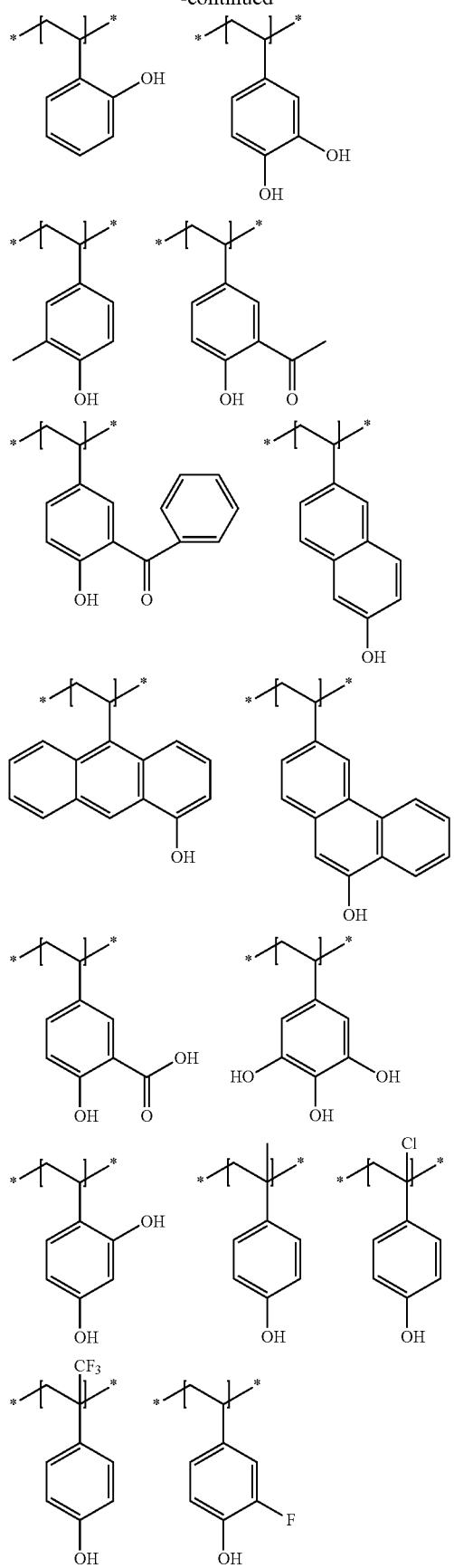
102
-continued
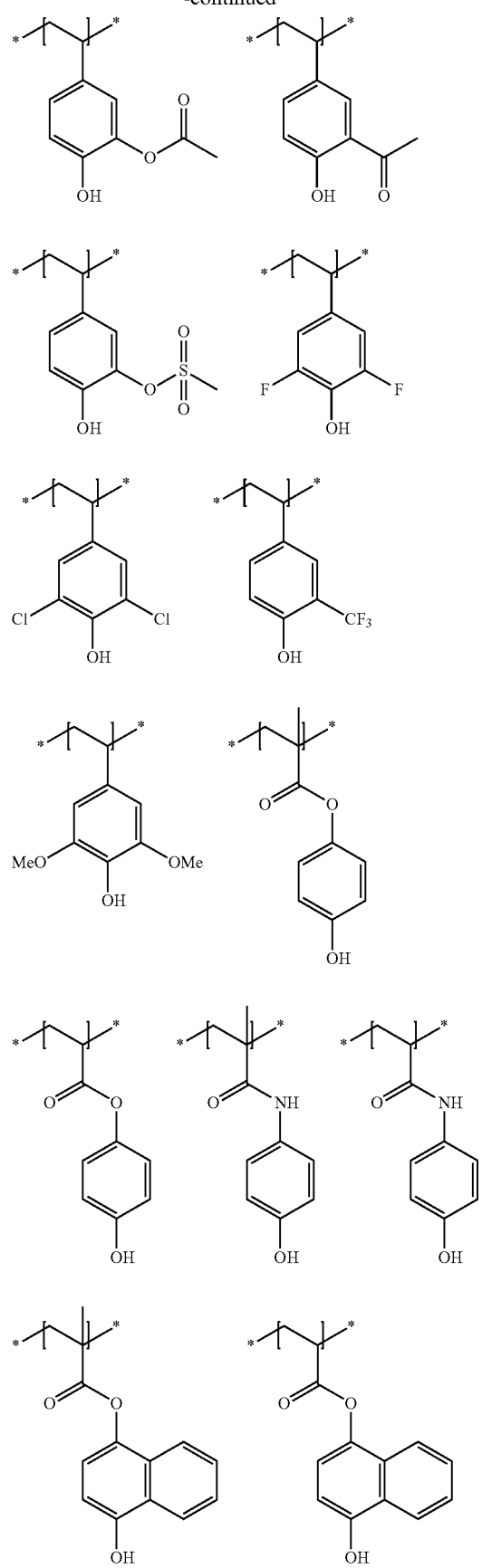

-continued

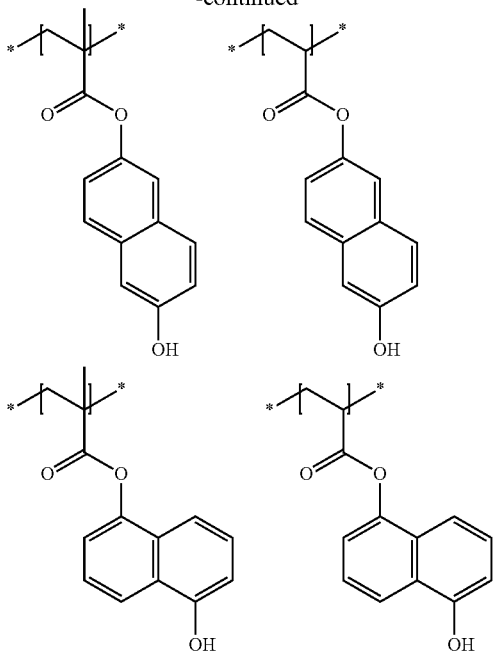

The compound (E) is a group having a non-acid-decomposable polycyclic alicyclic hydrocarbon structure, and preferably has a structure in which a hydrogen atom of the phenolic hydroxyl group is substituted in view of obtaining a high glass transition temperature (Tg), and improving the dry etching resistance.

When the compound (E) has the above described specific structure, the glass transition temperature (Tg) of the compound (E) is increased, thereby forming a very hard resist film. Thus, the diffusivity of an acid or the dry etching resistance may be controlled. Accordingly, since the diffusivity of an acid at an exposed portion to actinic rays such as electron beam or extreme UV rays, or radiation is highly suppressed, the resolution, pattern shape and LER in a fine pattern may be more excellent. It is thought that the non-acid-decomposable polycyclic alicyclic hydrocarbon structure contained in the compound (E) contributes to a further improvement of the dry etching resistance. Also, although details are unclear, it is assumed that the polycyclic alicyclic hydrocarbon structure is highly hydrogen-radical donating and thus serves as a hydrogen source at the decomposition of the compound (B) capable of generating an acid upon irradiation with an actinic ray or radiation (which is a photo-acid generator), thereby further improving the decomposition efficiency of the photo-acid generator, and further increasing the acid generation efficiency. Also, it is thought that this contributes to a higher sensitivity.

In the above described specific structure which the compound (E) according to the present invention may have, an aromatic ring such as a benzene ring and a group having a non-acid-decomposable polycyclic alicyclic hydrocarbon structure are linked through an oxygen atom derived from a phenolic hydroxyl group. As described above, the structure not only contributes to a high dry etching resistance but also increases the glass transition temperature (Tg) of the compound (E), and it is assumed that due to the effect of a combination of these, a higher resolution is provided.

In the present invention, a non-acid-decomposable property means a property which does not cause a decomposition reaction by an acid generated from the compound (B) capable of generating an acid upon irradiation with an actinic ray or radiation.

More specifically, a group having a non-acid-decomposable polycyclic alicyclic hydrocarbon structure is preferably a group stable in acid and alkali. The group stable in acid and alkali refers to a group which does not show an acid-decomposable property or an alkali decomposable property. Here, the acid-decomposable property means a property which causes a decomposition reaction by the action of an acid generated from the compound (B) capable of generating an acid upon irradiation with an actinic ray or radiation, and as for the group showing the acid-decomposable property, acid-decomposable groups described below in "a repeating unit having an acid-decomposable group" may be exemplified.

Also, the alkali decomposable property means a property which causes a decomposition reaction by the action of an alkali developer, and as for the group showing the alkali decomposable property, a group capable of decomposing by the action of a conventionally known alkali developer to increase the dissolution rate in the alkali developer, which is included in a resin suitably used in the positive-type chemical amplification resist composition (e.g., a group having a lactone structure) may be exemplified.

A group having a polycyclic alicyclic hydrocarbon structure is not particularly limited as long as it is a monovalent group having a polycyclic alicyclic hydrocarbon structure, but the number of the carbon atoms in total preferably ranges from 5 to 40, and more preferably from 7 to 30. The polycyclic alicyclic hydrocarbon structure may have an unsaturated bond in the ring.

In the group having a polycyclic alicyclic hydrocarbon structure, the polycyclic alicyclic hydrocarbon structure refers to a structure having a plurality of monocyclic alicyclic hydrocarbon groups, or a polycyclic alicyclic hydrocarbon structure, and may be a bridged type structure. As for the monocyclic alicyclic hydrocarbon group, a cycloalkyl group having 3 to 8 carbon atoms is preferred, and for example, a cyclopropyl group, a cyclopentyl group, a cyclohexyl group, a cyclobutyl group, and a cyclooctyl group may be exemplified, and the structure having a plurality of monocyclic alicyclic hydrocarbon groups has a plurality of these groups. The structure having a plurality of monocyclic alicyclic hydrocarbon groups preferably has 2 to 4 monocyclic alicyclic hydrocarbon groups, and particularly preferably has 2 monocyclic alicyclic hydrocarbon groups.

As for the polycyclic alicyclic hydrocarbon structure, a bicyclo, tricyclo, tetracyclo structure having 5 or more carbon atoms may be exemplified. A polycyclic cyclo structure having 6 to 30 carbon atoms is preferred, and for example, an adamantane structure, a decalin structure, a norbornane structure, a norbornene structure, a cedrol structure, an isobornane structure, a bornane structure, a dicyclopentane structure, an α-pinene structure, a tricyclodecane structure, a tetracyclododecane structure or an androstane structure may be exemplified. A part of carbon atoms in the monocyclic or polycyclic cycloalkyl group may be substituted with hetero atoms such as an oxygen atom.

As for preferred examples of the polycyclic alicyclic hydrocarbon structure, an adamantane structure, a decalin structure, a norbornane structure, a norbornene structure, a cedrol structure, a structure having a plurality of cyclohexyl groups, a structure having a plurality of cycloheptyl groups, a structure having a plurality of cyclooctyl groups, a structure having a plurality of cyclodecanyl groups, a group having a plurality of cyclododecanyl groups, and a tricyclodecane structure may be exemplified, and an adamantane structure is the most preferred in view of the dry etching resistance (that is, a group having the non-acid-decomposable polycyclic alicyclic hydrocarbon structure is most preferably a group having a non-acid-decomposable adamantane structure).

Chemical formulas for the polycyclic alicyclic hydrocarbon structure (in a case of a structure having a plurality of monocyclic alicyclic hydrocarbon groups, monocyclic alicyclic hydrocarbon structures corresponding to the monocyclic alicyclic hydrocarbon groups (specifically, structures of Formulas (47) to (50) below)) will be described below.

[Chem. 47]

 (1)

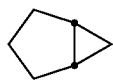 (2)

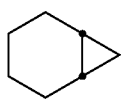 (3)

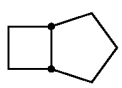 (4)

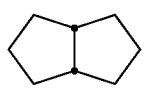 (5)

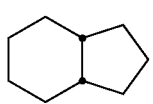 (6)

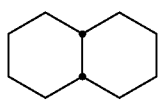 (7)

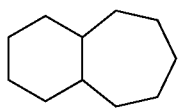 (8)

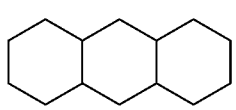 (9)

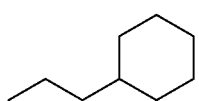 (10)

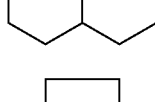 (11)

-continued

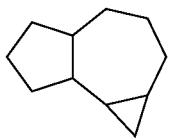 (12)

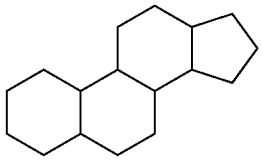 (13)

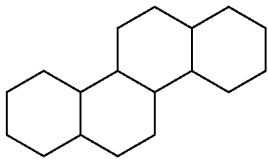 (14)

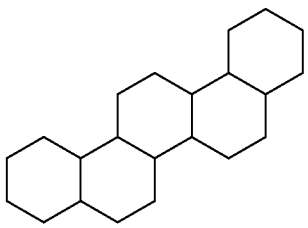 (15)

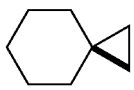 (16)

 (17)

 (18)

 (19)

 (20)

 (21)

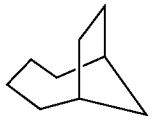 (22)

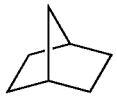 (23)

-continued
(24) 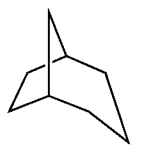
(25) 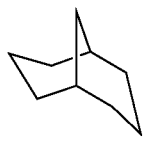
(26) 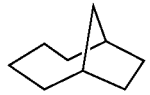
(27) 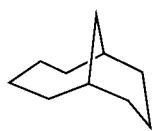
(28) 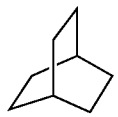
(29) 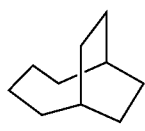
(30) 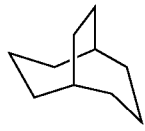
(31) 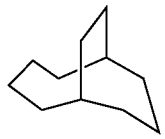
(32) 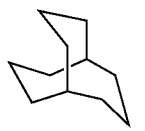
(33) 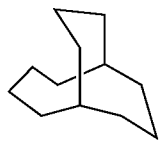
(34) 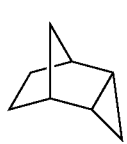
-continued
(35) 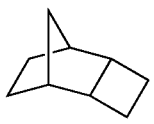
(36) 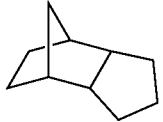
(37) 
(38) 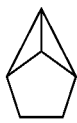
(39) 
(40) 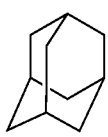
(41) 
(42) 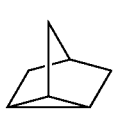
(43) 
(44) 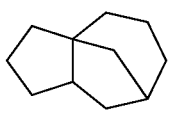
(45) 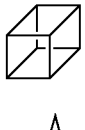
(46) 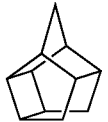

-continued

(47)

(48)

(49)

(50)
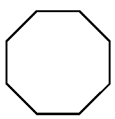

[Chem. 48]

(51)

Further, the polycyclic alicyclic hydrocarbon structure may have a substituent, and as for the substituent, for example, an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, a carbonyl group, a thiocarbonyl group, an alkoxycarbonyl group (preferably having 2 to 7 carbon atoms) and a group having a combination of these groups (preferably having 1 to 30 carbon atoms in total, more preferably 1 to 15 carbon atoms in total) may be exemplified.

As for the polycyclic alicyclic hydrocarbon structure, a structure represented by any of Formulas (7), (23), (40), (41) and (51) above, or a structure having two monovalent groups each of which includes any one hydrogen atom in the structure of Formula (48) as a bond is preferred, a structure represented by any of Formulas (23), (40) and (51), or a structure having two monovalent groups each of which includes any one hydrogen atom in the structure of Formula (48) above as a bond is more preferred, and a structure represented by Formula (40) above is the most preferred.

As for the group having a polycyclic alicyclic hydrocarbon structure, a monovalent group including any one hydrogen atom in the polycyclic alicyclic hydrocarbon structure as above as a bond is preferred.

The above described group having a non-acid-decomposable polycyclic alicyclic hydrocarbon structure, which has a structure in which a hydrogen atom of the phenolic hydroxyl group is substituted, is preferably contained as a repeating unit having the group having a non-acid-decomposable polycyclic alicyclic hydrocarbon structure, which has a structure in which a hydrogen atom of the phenolic hydroxyl group is substituted, in the compound (E) as the polymer compound, and is more preferably contained, as a repeating unit represented by Formula (3) below, in the compound (E).

[Chem. 49]

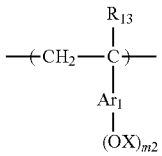

(3)

In Formula (3), $R_{13}$ represents a hydrogen atom or a methyl group.

X represents a group having a non-acid-decomposable polycyclic alicyclic hydrocarbon structure.

$Ar_1$ represents an aromatic ring.

m2 is an integer of 1 or more.

In Formula (3), $R_{13}$ represents a hydrogen atom or a methyl group, but a hydrogen atom is particularly preferred.

As for the aromatic ring of $Ar_1$ in Formula (3), for example, an aromatic hydrocarbon ring having 6 to 18 carbon atoms, which may have a substituent, such as a benzene ring, a naphthalene ring, an anthracene ring, a fluorene ring, and a phenanthrene ring, or an aromatic heterocyclic ring including a hetero ring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring, may be exemplified. Among them, a benzene ring, and a naphthalene ring are preferred in view of resolution, and a benzene ring is the most preferred.

The aromatic ring of Ar may have a substituent other than the group represented by —OX, and as for the substituent, for example, an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, an alkoxycarbonyl group (preferably having 2 to 7 carbon atoms) may be exemplified. An alkyl group, an alkoxy group, and an alkoxycarbonyl group are preferred, and an alkoxy group is more preferred.

X represents a group having a non-acid-decomposable polycyclic alicyclic hydrocarbon structure. Specific examples and preferred ranges of the group having a non-acid-decomposable polycyclic alicyclic hydrocarbon structure, represented by X, are the same as those described above. More preferably, X is a group represented by —Y—$X_2$ in Formula (4) described below.

m2 is preferably an integer of 1 to 5, and is most preferably 1. When m2 is 1, and Ar is a benzene ring, the substitution position of —OX may be a para position, a meta position or an ortho position with respect to the binding position with a polymer backbone of a benzene ring, but a para position or a meta position is preferred, and a para position is more preferred.

In the present invention, the repeating unit represented by Formula (3) above is preferably a repeating unit represented by Formula (4) below.

When a polymer compound (E) having the repeating unit represented by Formula (4) is used, Tg of the polymer compound (E) is increased, thereby forming a very hard resist film. Thus, the diffusivity of an acid or the dry etching resistance may be more securely controlled.

[Chem. 50]

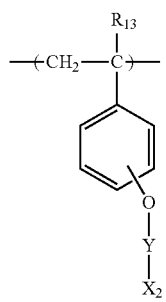

(4)

In Formula (4), $R_{13}$ represents a hydrogen atom or a methyl group.

Y represents a single bond or a divalent linking group.

$X_2$ represents a non-acid-decomposable polycyclic alicyclic hydrocarbon group.

Preferred examples of the repeating unit represented by Formula (4) above, which are used in the present invention, will be described below.

In Formula (4), $R_{13}$ represents a hydrogen atom or a methyl group, but a hydrogen atom is particularly preferred.

In Formula (4), Y is preferably a divalent linking group. As for a preferred group as a divalent linking group of Y, a carbonyl group, a thiocarbonyl group, an alkylene group (preferably having 1 to 10 carbon atoms, more preferably 1 to 5 carbon atoms), a sulfonyl group, —COCH$_2$—, —NH— or a divalent linking group having a combination thereof (preferably having 1 to 20 carbon atoms in total, more preferably 1 to 10 carbon atoms in total) may be exemplified. A carbonyl group is more preferred, —COCH$_2$—, a sulfonyl group, —CONH—, or —CSNH— is more preferred, a carbonyl group or —COCH$_2$— is still more preferred, and a carbonyl group is particularly preferred.

$X_2$ represents a polycyclic alicyclic hydrocarbon group, and is non-acid-decomposable. The total number of carbon atoms of the polycyclic alicyclic hydrocarbon group preferably ranges from 5 to 40, and more preferably from 7 to 30. The polycyclic alicyclic hydrocarbon group may have an unsaturated bond in the ring.

Such a polycyclic alicyclic hydrocarbon group may be a group having a plurality of monocyclic alicyclic hydrocarbon groups, or a polycyclic alicyclic hydrocarbon group, and may be a bridged type group. as for the monocyclic alicyclic hydrocarbon group, a cycloalkyl group having 3 to 8 carbon atoms is preferred, and for example, a cyclopropyl group, a cyclopentyl group, a cyclohexyl group, a cyclobutyl group, and a cyclooctyl group may be exemplified, and the group may have a plurality of these groups. The group having a plurality of monocyclic alicyclic hydrocarbon groups preferably has 2 to 4 monocyclic alicyclic hydrocarbon groups, and particularly preferably has 2 monocyclic alicyclic hydrocarbon groups.

As for the polycyclic alicyclic hydrocarbon group, a group having a bicyclo, tricyclo, tetracyclo structure having 5 or more carbon atoms may be exemplified. A group having a polycyclic cyclo structure having 6 to 30 carbon atoms is preferred, and for example, an adamantyl group, a norbornyl group, a norbornenyl group, an isobornyl group, a camphanyl group, a dicyclopentyl group, an α-pinel group, a tricyclodecanyl group, a tetracyclododecyl group or an androstanyl group may be exemplified. A part of carbon atoms in the monocyclic or polycyclic cycloalkyl group may be substituted with hetero atoms such as an oxygen atom.

As for the polycyclic alicyclic hydrocarbon group of $X_2$, an adamantyl group, a decalin group, a norbornyl group, a norbornenyl group, a cedrol group, a group having a plurality of cyclohexyl groups, a group having a plurality of cycloheptyl groups, a group having a plurality of cyclooctyl groups, a group having a plurality of cyclodecanyl groups, a group having a plurality of cyclododecanyl groups, and a tricyclodecanyl group are preferred, and an adamantyl group is the most preferred in view of the dry etching resistance. As for the chemical formulas of a polycyclic alicyclic hydrocarbon structure in the polycyclic alicyclic hydrocarbon group of $X_2$, the same as chemical formulas of the polycyclic alicyclic hydrocarbon structure in the group having the polycyclic alicyclic hydrocarbon structure as described above may be exemplified, and the preferred ranges thereof are also the same. As for the polycyclic alicyclic hydrocarbon group of $X_2$, a monovalent group including any one hydrogen atom in the polycyclic alicyclic hydrocarbon structure as above as a bond may be exemplified.

Further, the alicyclic hydrocarbon group may have a substituent, and as for the substituent, the same as those described above as the substituent which the polycyclic alicyclic hydrocarbon structure may have may be exemplified.

In the Formula (4), the substitution position of —O—Y—$X_2$ may be a para position, a meta position or an ortho position with respect to the binding position with the polymer backbone of a benzene ring, but a para position is preferred.

In the present invention, the repeating unit represented by Formula (3) above is most preferably a repeating unit represented by Formula (4') below.

[Chem. 51]

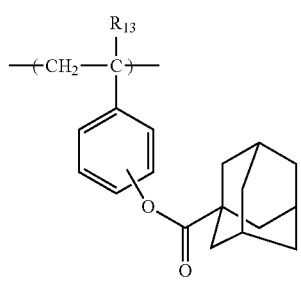

(4')

In Formula (4'), $R_{13}$ represents a hydrogen atom or a methyl group.

In Formula (4'), $R_{13}$ represents a hydrogen atom or a methyl group, and a hydrogen atom is particularly preferred.

In Formula (4'), the substitution position of an adamantylester group may be a para position, a meta position or an ortho position with respect to the binding position with the polymer backbone of a benzene ring, but a para position is preferred.

Specific examples of the repeating unit represented by Formula (3) will be described below.

[Chem. 52]
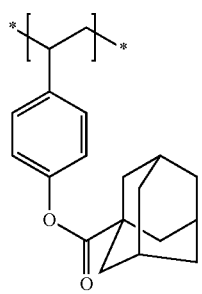
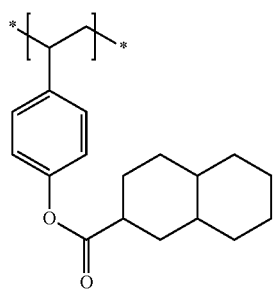
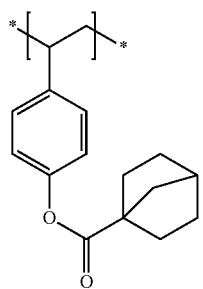
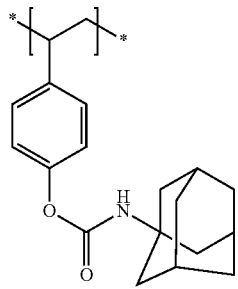
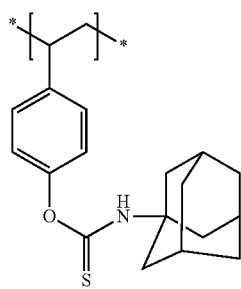
-continued
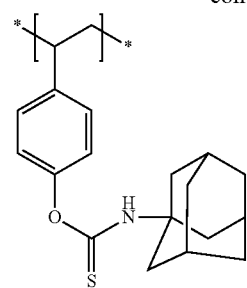
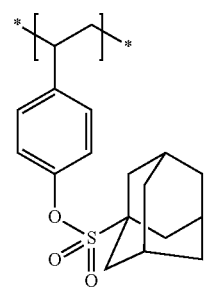
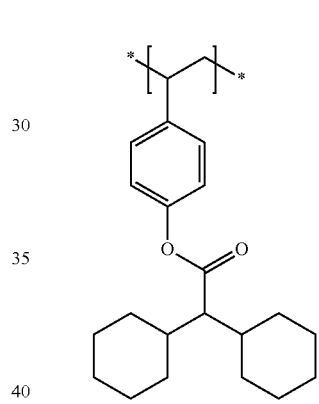
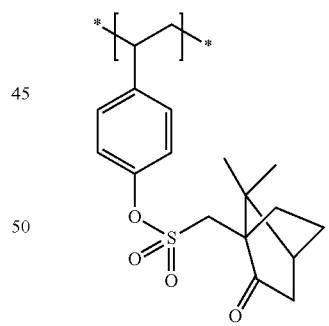
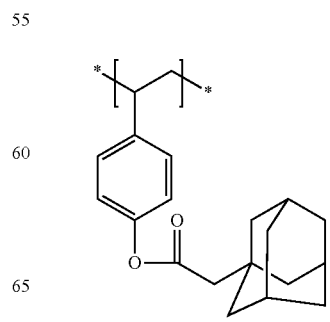

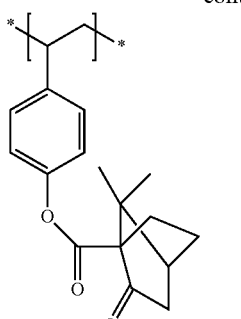
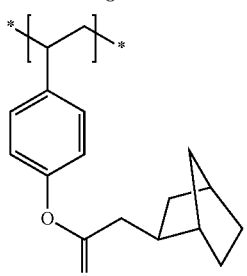
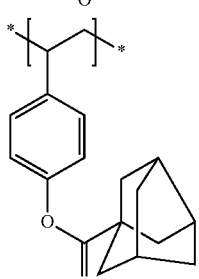
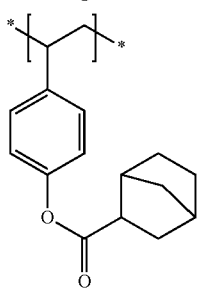
[Chem. 53]
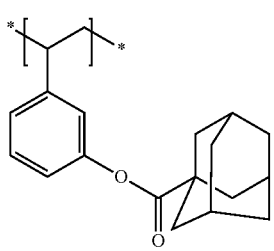
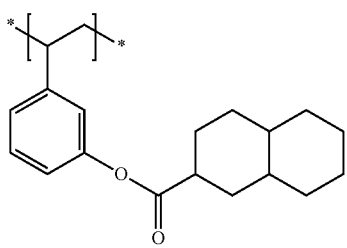
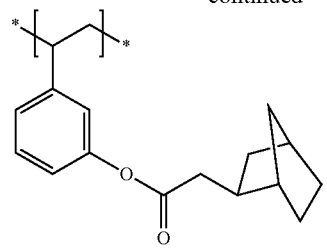
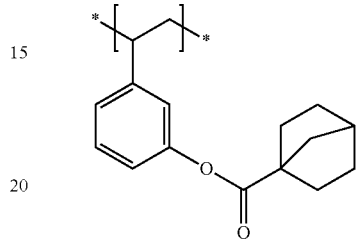
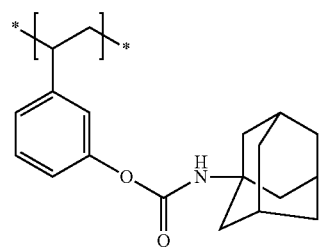
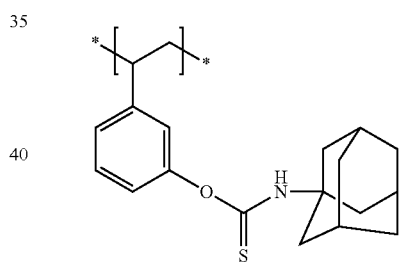
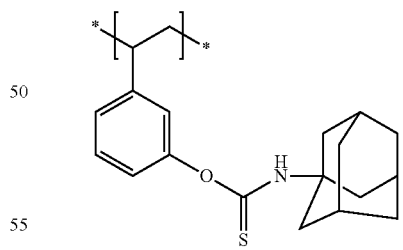
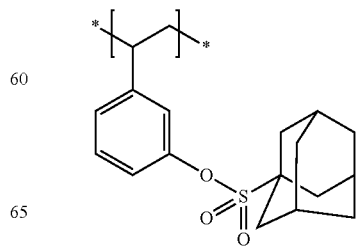

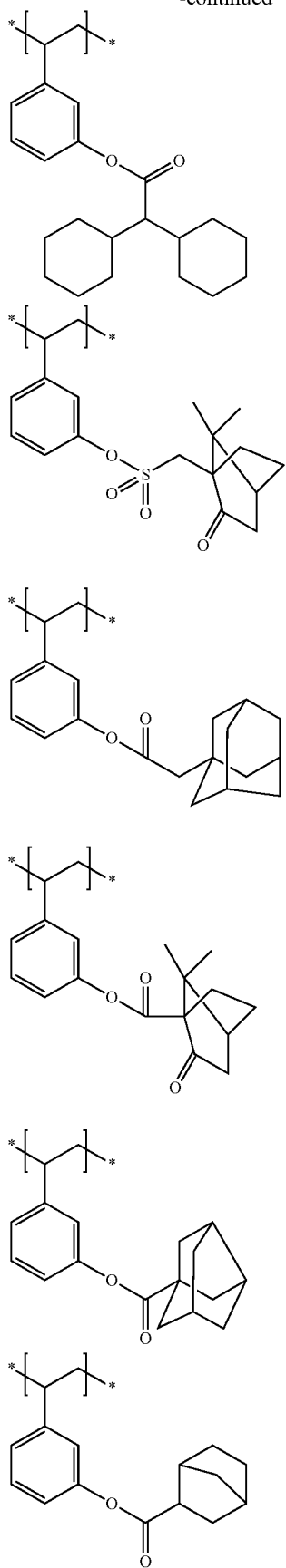
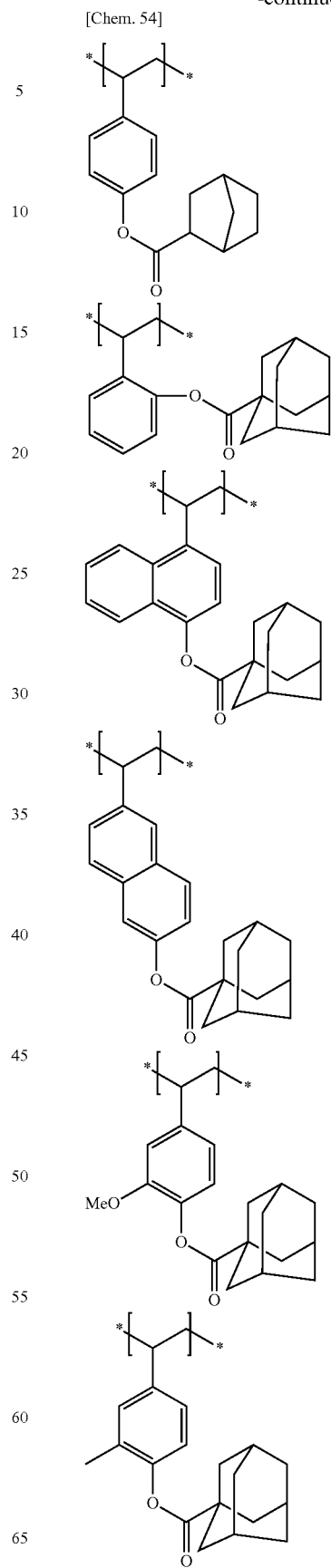
[Chem. 54]

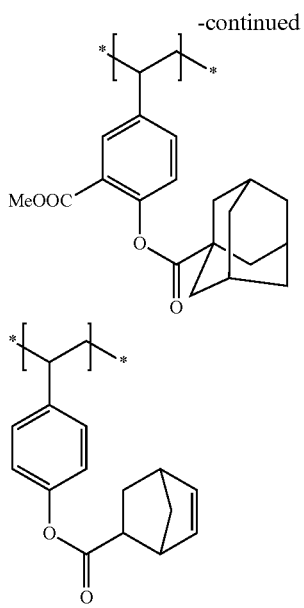

When the compound (E) is a polymer compound, and contains the above described repeating unit having a group which has a non-acid-decomposable polycyclic alicyclic hydrocarbon structure, in which a hydrogen atom of the phenolic hydroxyl group is substituted, the content of the repeating units preferably ranges from 1 mol % to 40 mol %, and more preferably from 2 mol % to 30 mol % based on the total of repeating units of the compound (E) as for the polymer compound.

Preferably, the compound (E) as for the polymer compound used in the present invention may further include the following repeating unit (hereinafter, also referred to as "other repeating unit") as a repeating unit other than the above described repeating unit.

Examples of a polymerizable monomer for forming these other repeating units may include styrene, alkyl-substituted styrenes, alkoxy-substituted styrene, halogen-substituted styrene, O-alkylated styrene, O-acylated styrene, hydrogenated hydroxystyrene, maleic anhydride, acrylic acid derivatives (e.g., acrylic acid, acrylic acid ester), a methacrylic acid derivative (e.g., methacrylic acid and methacrylic acid ester), N-substituted maleimide, acrylonitrile, methacrylonitrile, vinyl naphthalene, vinyl anthracene, and indene which may have a substituent.

The compound (E) as for the polymer compound may or may not contain these other repeating units. However, when these other repeating units are contained, the content of these other repeating units in the compound (E) as for the polymer compound generally from 1 mol % to 30 mol %, preferably from 1 mol % to 20 mol %, and more preferably from 2 mol % to 10 mol % based on the total repeating units which constitute the compound (E) as for the polymer compound.

The compound (E) as for the polymer compound may be synthesized by a conventionally known method such as a radical polymerization method, an anionic polymerization method or a living radical polymerization (e.g., an iniferter method). For example, in the anionic polymerization method, vinyl monomers are dissolved in an appropriate organic solvent, and reacted usually under a cooling condition by using a metal compound (e.g., butyllithium) as an initiator, thereby obtaining a polymer.

As for the compound (E) as the polymer compound, a polyphenol compound produced by a condensation reaction of an aromatic ketone or aromatic aldehyde and a compound containing 1 to 3 phenolic hydroxyl groups (e.g., Japanese Patent Application Laid-Open No. 2008-145539), a calixarene derivative (e.g., Japanese Patent Application Laid-Open No. 2004-18421), a noria derivative (e.g., Japanese Patent Application Laid-Open No. 2009-222920), or a polyphenol derivative (e.g., Japanese Patent Application Laid-Open No. 2008-94782) may also be employed, and these may be modified by a polymer reaction to synthesize the compound.

Also, the compound (E) as the polymer compound is preferably synthesized by modifying a polymer synthesized by a radical polymerization or anionic polymerization, through a polymer reaction.

The weight average molecular weight of the compound (E) as the polymer compound preferably ranges from 1,000 to 200,000, more preferably from 2,000 to 50,000, and still more preferably from 2,000 to 15,000.

The polydispersity (molecular weight distribution) (Mw/Mn) of the compound (E) as the polymer compound is preferably 2.5 or less and more preferably ranges from 1.0 to 2.5, still more preferably from 1.0 to 1.6, and most preferably from 1.0 to 1.25 from the standpoint of enhancing the sensitivity and resolution. The use of living polymerization such as living anionic polymerization is preferred because the obtained polymer compound may have a uniform polydispersity (molecular weight distribution). The weight average molecular weight and the polydispersity of the compound (E) as the polymer compound are defined as values in terms of polystyrene by GPC measurement.

The compound (E) may be used either alone or in combination of two or more kinds thereof.

The addition amount of the compound (E) used in the chemical amplification resist composition of the present invention preferably ranges from 30% by mass to 95% by mass, more preferably from 40% by mass to 90% by mass, and particularly preferably from 50% by mass to 85% by mass, based on the total solid content of the composition.

Specific examples of the compound (E) will be described below, but the present invention is not limited thereto.

[Chem. 55]

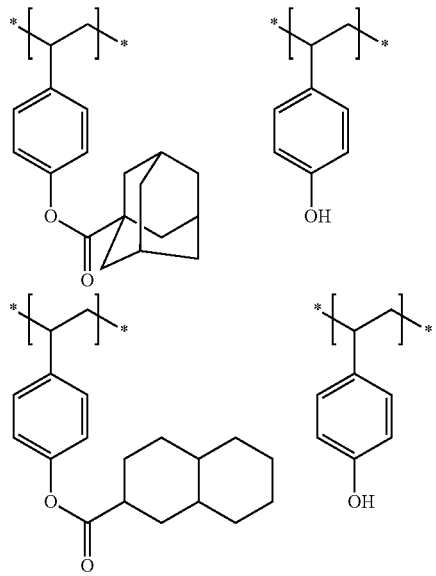

121
-continued
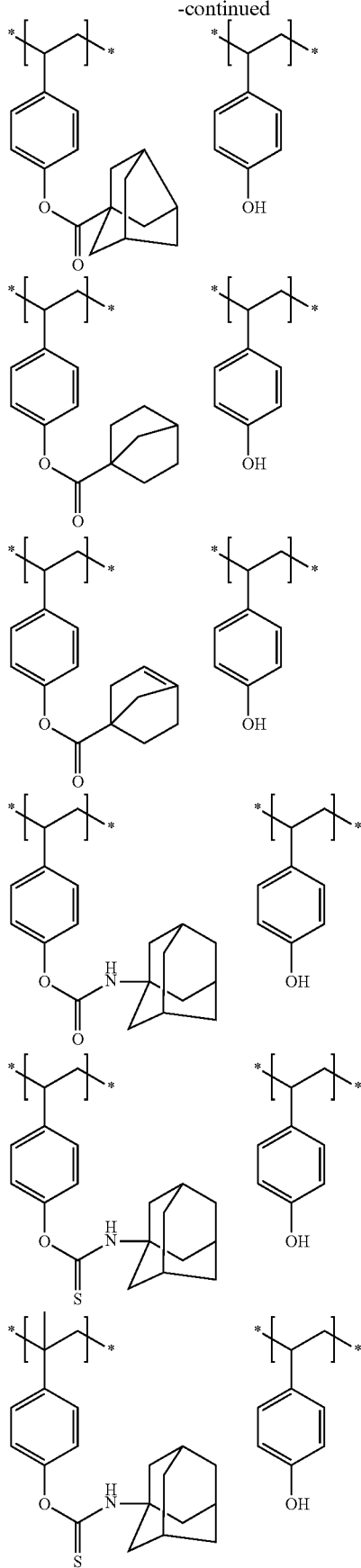
122
-continued
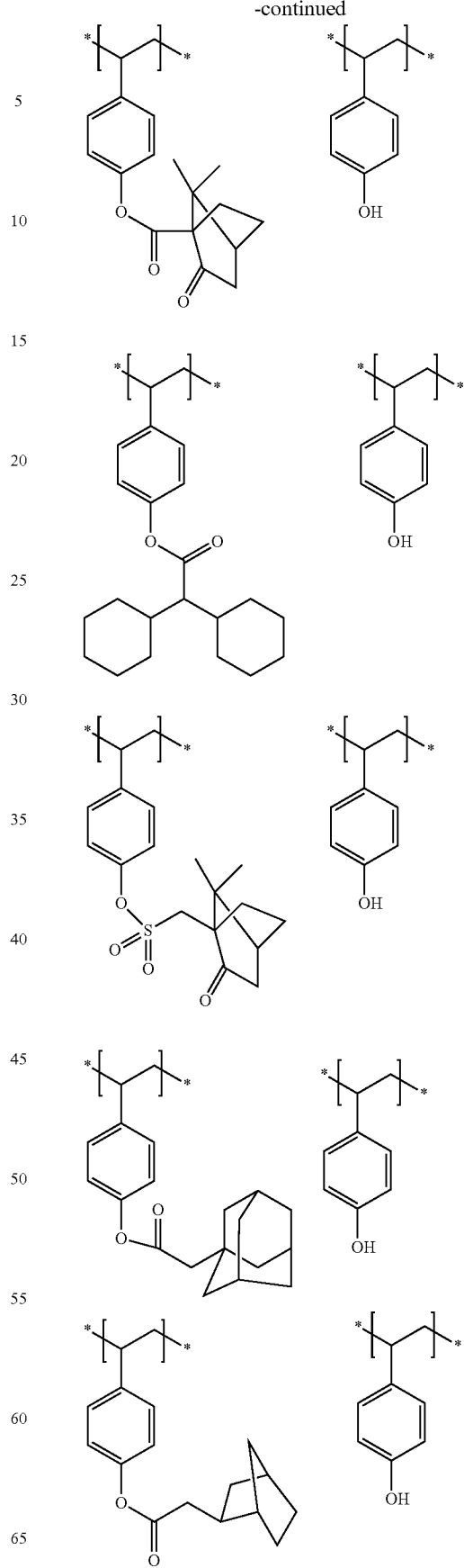

123
-continued
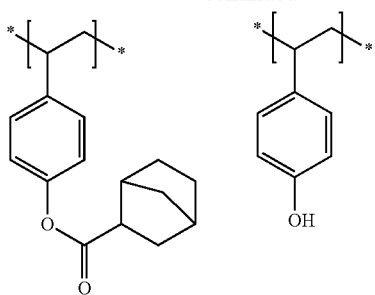
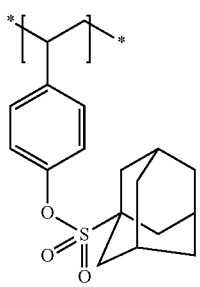
[Chem. 56]
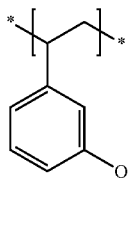
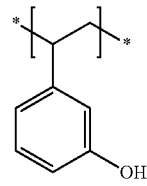
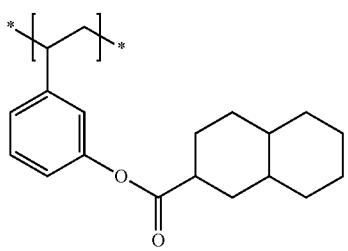
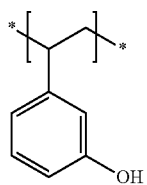
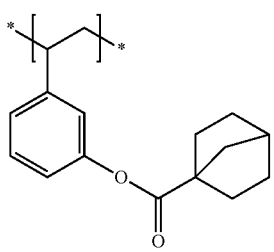
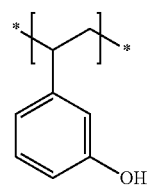
124
-continued
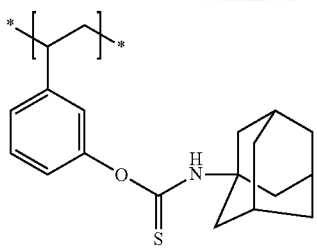
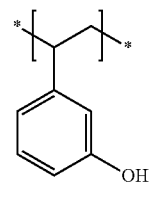
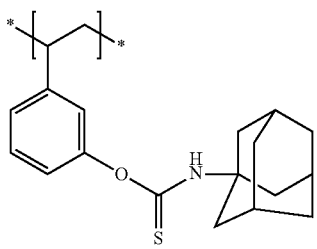
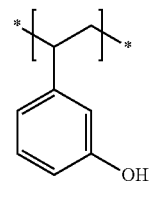
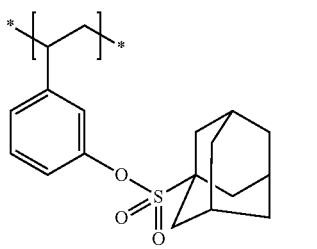
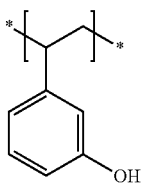
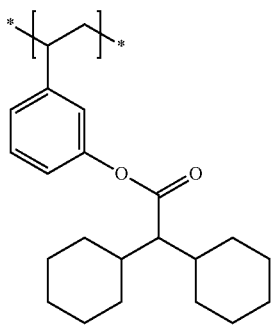
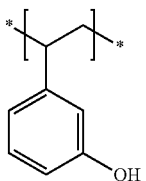
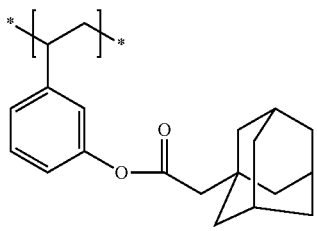
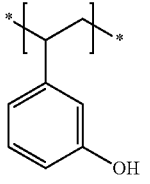
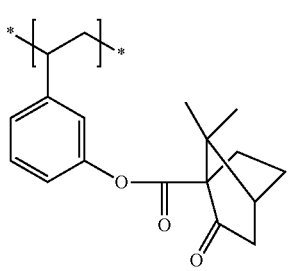
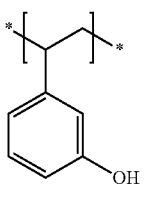

125
-continued
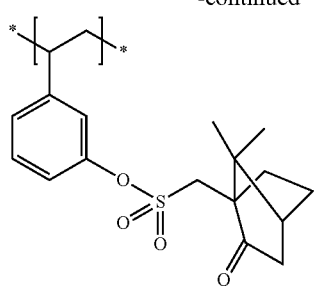 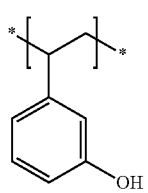
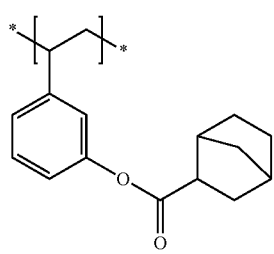 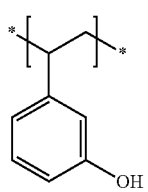
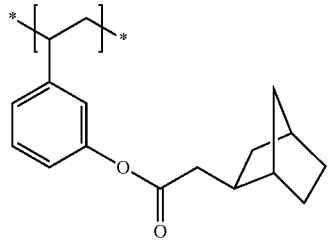 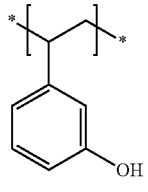
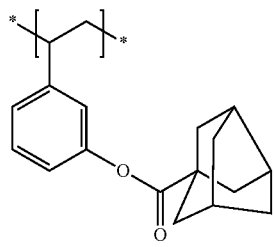 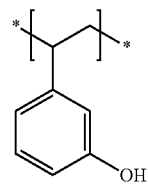
[Chem. 57]
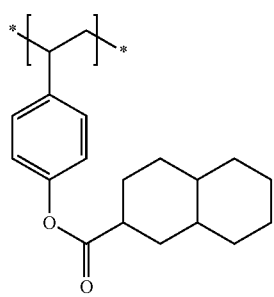 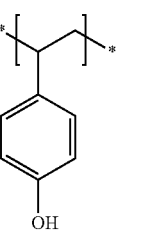
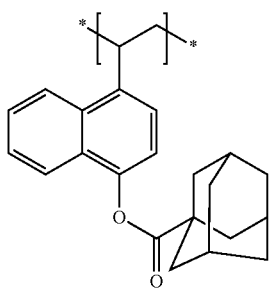 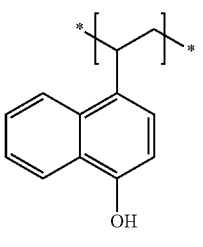
126
-continued
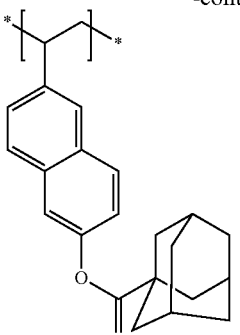 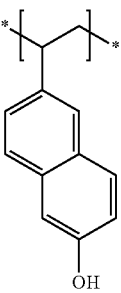
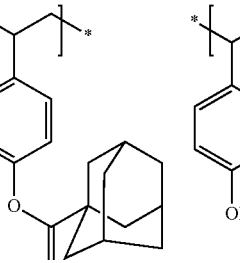 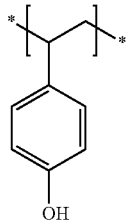
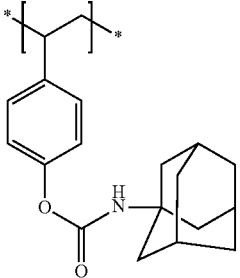 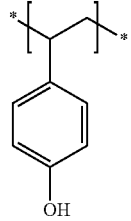 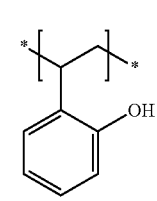
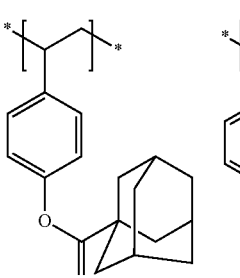 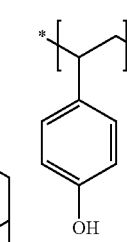 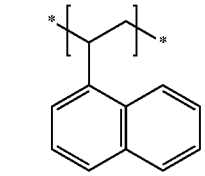
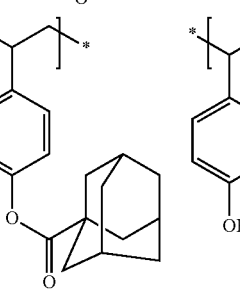 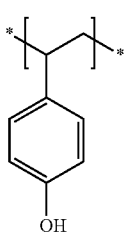 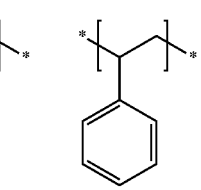
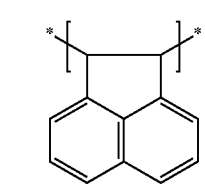

-continued

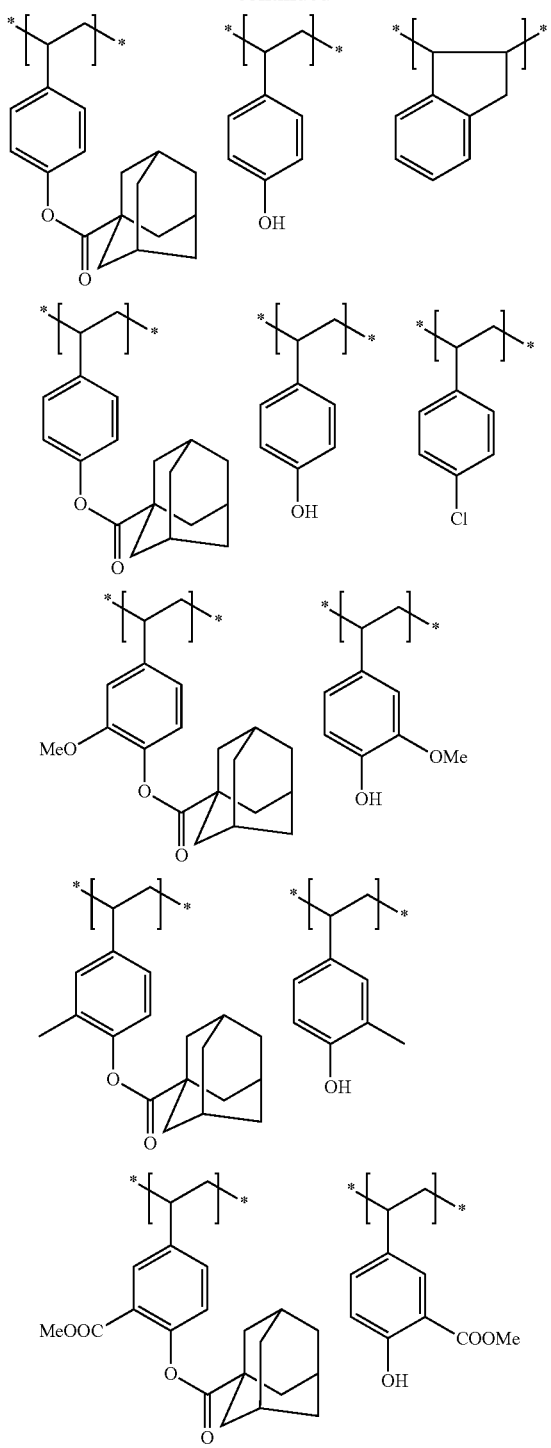

[Chem. 58]

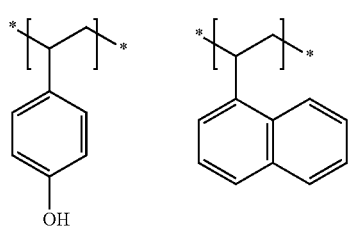

-continued

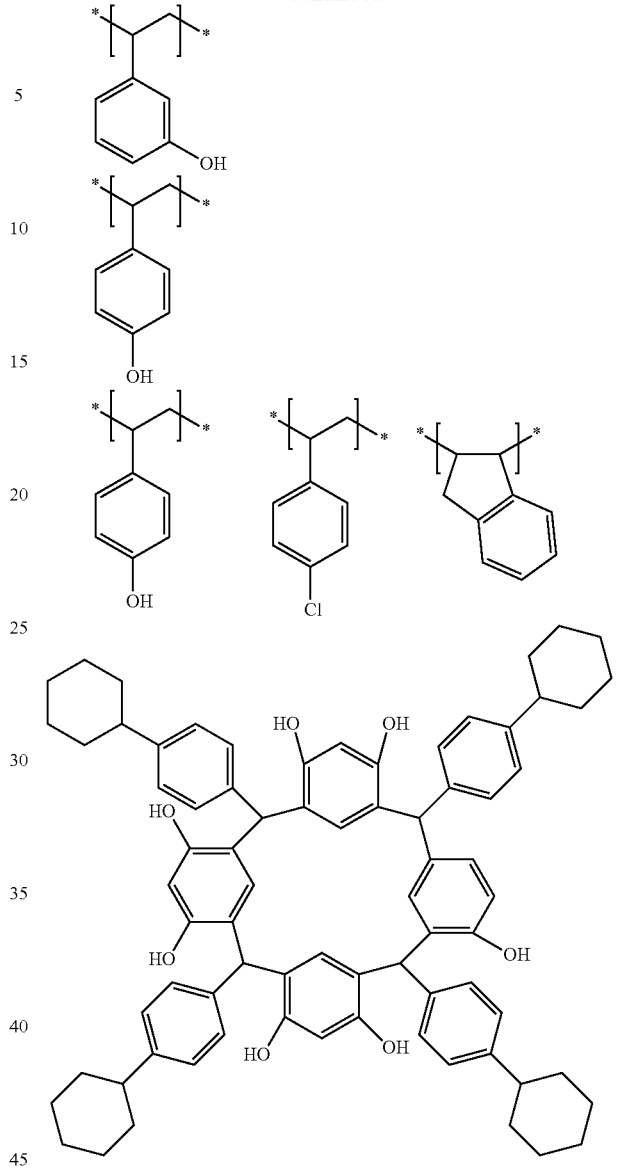

[5] (D) Crosslinking Agent

The chemical amplification resist composition of the present invention preferably contains a crosslinking agent (D) (hereinafter, properly referred to as an acid crosslinking agent or simply as a crosslinking agent) when a negative-type pattern is formed.

The chemical amplification resist composition of the present invention more preferably contains a compound having two or more hydroxyl methyl groups or alkoxy methyl groups in the molecule, as for the crosslinking agent (D).

As for the preferred crosslinking agent, hydroxymethylated or alkoxymethylated phenol compounds, alkoxymethylated melamine compounds, alkoxymethyl glycoluril-based compounds, and alkoxymethylated urea-based compounds may be exemplified, and among them, hydroxymethylated or alkoxymethylated phenol compounds are preferred in view of obtaining a good pattern shape. As for the compound (D) as the particularly preferred cross-linking agent, a phenol derivative having a molecular weight of 1,200 or less and containing, per molecule, from 3 to 5 benzene rings and a total of two or more hydroxymethyl groups or alkoxymethyl groups, a melamine-formaldehyde derivative having at least two free N-alkoxymethyl groups, or an alkoxymethyl glycoluril derivative may be exemplified.

In view of a pattern shape, the chemical amplification resist composition of the present invention, as for the crosslinking agent (D), more preferably contains at least two kinds of compounds each of which has two or more alkoxymethyl groups per molecule, and still more preferably contains at least two kinds of phenol compounds each of which has two or more alkoxymethyl groups per molecule, and particularly preferably, at least one kind of the at least two kinds of phenol compounds is a phenol derivative having a molecular weight of 1,200 or less and containing, per molecule, from 3 to 5 benzene rings and a total of two or more alkoxymethyl groups.

As for the alkoxymethyl group, a methoxymethyl group, or an ethoxymethyl group is preferred.

Among the crosslinking agents, a phenol derivative having a hydroxymethyl group may be obtained by reacting a corresponding phenol compound having no hydroxymethyl group with formaldehyde in the presence of a base catalyst. Also, a phenol derivative having an alkoxymethyl group may be obtained by reacting a corresponding phenol derivative having a hydroxymethyl group with an alcohol in the presence of an acid catalyst.

Among the phenol derivatives synthesized as described above, a phenol derivative having an alkoxymethyl group is particularly preferred in view of the sensitivity and storage stability.

As for other preferred examples of the crosslinking agent, compounds having an N-hydroxymethyl group or an N-alkoxymethyl group, such as alkoxymethylated melamine-based compounds, alkoxymethyl glycoluril-based compounds and alkoxymethylated urea-based compounds may be exemplified.

As for such compounds, hexamethoxymethylmelamine, hexaethoxymethylmelamine, tetramethoxymethyl glycoluril, 1,3-bismethoxymethyl-4,5-bismethoxyethyleneurea, and bismethoxymethylurea may be exemplified, which are disclosed in EP0,133,216A, West German Patent Nos. 3,634,671, and 3,711,264, and EP0,212,482A.

Among these crosslinking agents, particularly preferred examples will be described below.

[Chem. 59]

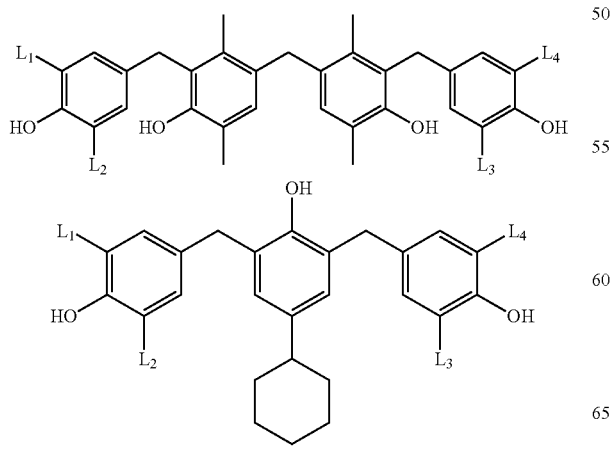

-continued

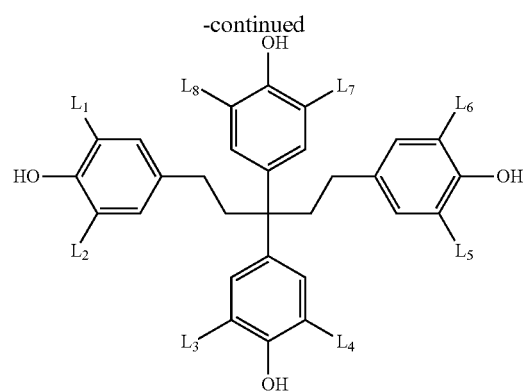

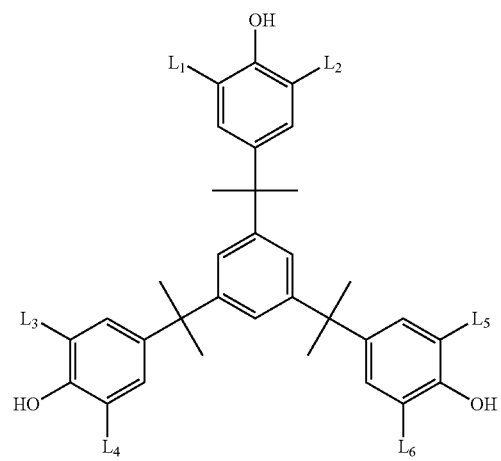

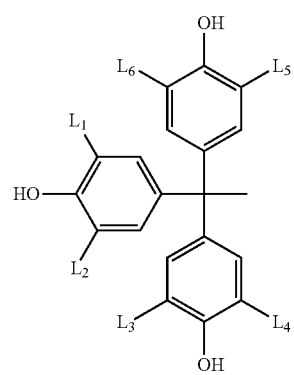

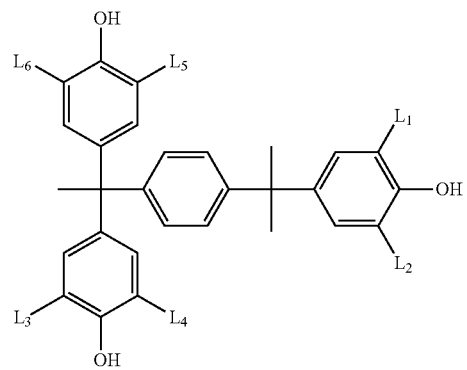

-continued

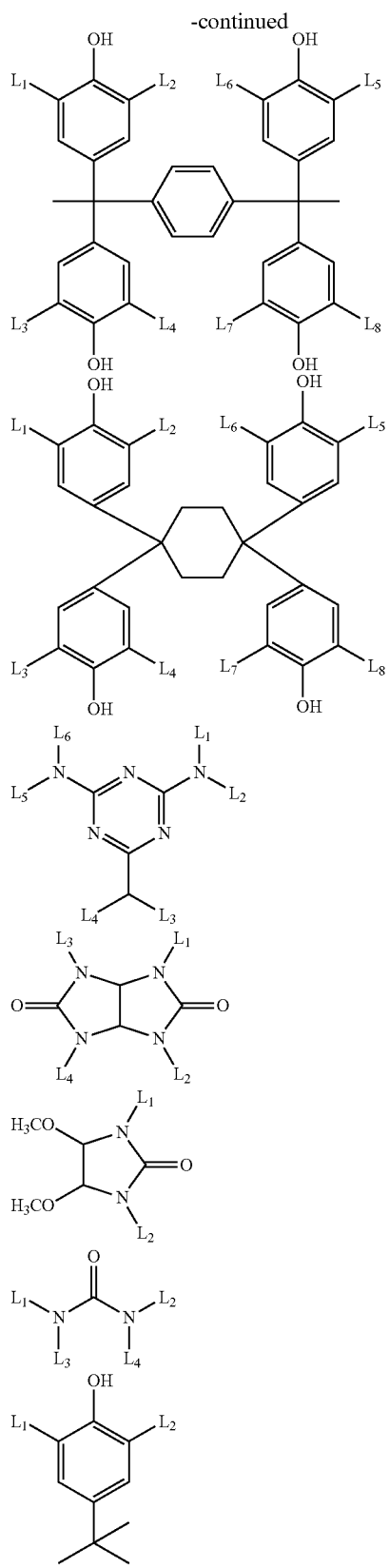

In the formulas, each of $L_1$ to $L_8$ independently represents a hydrogen atom, a hydroxymethyl group, a methoxymethyl group, an ethoxymethyl group or an alkyl group having 1 to 6 carbon atoms.

The crosslinking agent in the present invention is used in an addition amount preferably in a range of 3% by mass to 65% by mass, more preferably of 5% by mass to 50% by mass, and still more preferably of 5% by mass to 30% by mass based on the solid content of the resist composition. When the addition amount of the crosslinking agent ranges from 3% by mass to 65% by mass, it is possible to suppress the residual film ratio and the resolution from being reduced, and also to maintain a good stability during the storage of a resist liquid.

In the present invention, the crosslinking agent may be used either alone or in combination of two or more kinds thereof, and in view of a pattern shape, the use in combination of two or more kinds is preferred.

For example, in the case of using the phenol derivative together with another crosslinking agent, for example, the above-described compound having an N-alkoxymethyl group, in combination, the ratio between the phenol derivative and another crosslinking agent preferably, in terms of molar ratio, ranges from 100/0 to 20/80, preferably from 90/10 to 40/60, more preferably from 80/20 to 50/50.

[6] Basic Compound

The chemical amplification resist composition of the present invention preferably contains a basic compound, in addition to the components described above, as an acid scavenger. By using the basic compound, the change of performance with aging from exposure to post-heating may be reduced. As for such a basic compound, an organic basic compound is preferred, and more specifically, aliphatic amines, aromatic amines, heterocyclic amines, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, amide derivatives, and imide derivatives may be exemplified. An amine oxide compound (preferably having a methyleneoxy unit and/or an ethyleneoxy unit, e.g., compounds described in Japanese Patent Application Laid-Open No. 2008-102383) and an ammonium salt (preferably a hydroxide or a carboxylate; more specifically, a tetraalkylammonium hydroxide typified by tetrabutyl ammonium hydroxide is preferred in view of LER) may also be appropriately used.

Furthermore, a compound capable of increasing the basicity by the action of an acid may also be used as a kind of the basic compound.

Specific examples of the amines may include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, 2,4,6-tri(t-butyl)aniline, triethanolamine, N,N-dihydroxyethylaniline, tris(methoxyethoxyethyl)amine, the compounds exemplified in column 3, line 60 et seq. of U.S. Pat. No. 6,040,112, 2-[2-2-(2,2-dimethoxy-phenoxyethoxy)ethyl-bis-(2-methoxyethyl)]-amine, and compounds (C1-1) to (C3-3) exemplified in paragraph [0066] of U.S. Patent Application Publication No. 2007/0224539A1. Examples of the compound having a nitrogen-containing heterocyclic structure may include 2-phenylbenzimidazole, 2,4,5-triphenylimidazole, N-hydroxyethylpiperidine, bis(1,2,2,6,6-pentamethyl-4-piperidyl) sebacate, 4-dimethylaminopyridine, antipyrine, hydroxyantipyrine, 1,5-diazabicyclo[4.3.0]-non-5-ene, 1,8-diazabicyclo[5.4.0]-undeca-7-ene, and tetrabutyl ammonium hydroxide.

In addition, a photodecomposable basic compound (a compound which initially exhibits basicity due to the action of the basic nitrogen atom as a base but decomposes upon irradiation with an actinic ray or radiation to generate a zwitterionic compound having a basic nitrogen atom and an organic acid moiety and resulting from their neutralization in the molecule, is reduced in or deprived of the basicity; e.g., onium salts described in Japanese Registered Patent No. 3577743, Japanese Patent Application Laid-Open Nos. 2001-215689, 2001-166476, and 2008-102383), and a photobase generator (e.g., compounds described in Japanese Patent Application Laid-Open No. 2010-243773) may also be appropriately used.

Among these basic compounds, an ammonium salt or a photodecomposable basic compound is preferred in view of achieving a good LER.

In the present invention, the basic compound may be used either alone or in combination of two or more kinds thereof.

The content of the basic compound used in the present invention preferably ranges from 0.01% to 10% by mass, more preferably from 0.03% to 5% by mass, and particularly preferably from 0.05% to 3% by mass based on the total solid content of the resist composition.

[7] Surfactant

The chemical amplification resist composition of the present invention may contain a surfactant in order to improve the coatability. The surfactant is not particularly limited, but examples thereof may include a nonionic surfactant such as polyoxyethylene alkyl ethers, polyoxyethylene alkylallyl ethers, polyoxyethylene-polyoxypropylene block copolymers, sorbitan fatty acid esters and polyoxyethylene sorbitan fatty acid esters, a fluorine-based surfactant such as Megaface F171, F176 (manufactured by DIC Corporation), Florad FC430 (manufactured by Sumitomo 3M, Inc.), Surfynol E1004 (manufactured by Asahi Glass Co., Ltd.), and PF656 and PF6320 manufactured by OMNOVA, and an organosiloxane polymer such as a polysiloxane polymer KP-341 (manufactured by Shin-Etsu Chemical Co., Ltd.).

When the resist composition contains a surfactant, the use amount of the surfactant preferably ranges from 0.0001% to 2% by mass, and more preferably from 0.0005% to 1% by mass based on the total amount of the resist composition (excluding the solvent).

[8] Organic Carboxylic Acid

It is preferred that the chemical amplification resist composition of the present invention contains an organic carboxylic acid in addition to the components described above, in view of scum characteristics. As for the organic carboxylic acid compound, an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid, a benzoic acid derivative, a phthalic acid, a terephthalic acid, an isophthalic acid, a 2-naphthoic acid, a 1-hydroxy-2-naphthoic acid, and a 2-hydroxy-3-naphthoic acid may be exemplified. However, when the electron beam exposure is performed in vacuum, the organic carboxylic acid may vaporize from the resist film surface to contaminate the inside of a lithography chamber. Thus, a preferred compound is an aromatic organic carboxylic acid, and above all, for example, a benzoic acid, a 1-hydroxy-2-naphthoic acid, and a 2-hydroxy-3-naphthoic acid are preferred.

The blending amount of the organic carboxylic acid preferably ranges from 0.01 parts by mass to 10 parts by mass, more preferably from 0.01 parts by mass to 5 parts by mass, and still more preferably from 0.01 parts by mass to 3 parts by mass, based on 100 parts by mass of the phenolic hydroxyl group-containing compound (E).

The chemical amplification resist composition of the present invention, as necessary, may further contain, for example, a dye, a plasticizer, and an acid proliferating agent other than the compound (A) (described in International Publication Pamphlet Nos. WO95/29968, and WO98/24000, Japanese Patent Application Laid-Open Nos. H8-305262, H9-34106, and H8-248561, Japanese National Phase Patent Laid-Open Publication No. H8-503082, U.S. Pat. No. 5,445,917, Japanese National Phase Patent Laid-Open Publication No. H8-503081, U.S. Pat. Nos. 5,534,393, 5,395,736, 5,741,630, 5,334,489, 5,582,956, 5,578,424, 5,453,345, and 5,445,917, European Patent Nos. 665,960, 757,628 and 665,961, U.S. Pat. No. 5,667,943, Japanese Patent Application Laid-Open Nos. H10-1508, H10-282642, and H9-512498, Japanese Patent Application Laid-Open Nos. 2000-62337, 2005-17730, and 2008-209889). As for these compounds, respective compounds described in Japanese Patent Application Laid-Open No. 2008-268935 may be exemplified.

[Onium Carboxylate]

The chemical amplification resist composition of the present invention may contain an onium carboxylate. Examples of the onium carboxylate may include sulfonium carboxylate, iodonium carboxylate and ammonium carboxylate. Particularly, as for the onium carboxylate, iodonium carboxylate or sulfonium carboxylate is preferred. Also, in the present invention, it is preferred that the carboxylate residue of the onium carboxylate does not contain an aromatic group and a carbon-carbon double bond. The anion moiety is particularly preferably a linear or branched, monocyclic or polycyclic alkylcarboxylate anion having a carbon number of 1 to 30, and more preferably the carboxylate anion above in which the alkyl group is partially or entirely fluorine-substituted. Also, the alkyl chain may contain an oxygen atom. Accordingly, the transparency to light at 220 nm or less is ensured, and thus the sensitivity and resolution are enhanced, and the iso/dense bias and exposure margin are improved.

As for the solvent used in the chemical amplification resist composition of the present invention, for example, ethylene glycol monoethyl ether acetate, cyclohexanone, 2-heptanone, propylene glycol monomethyl ether (PGME, another name: 1-methoxy-2-propanol), propylene glycol monomethyl ether acetate (PGMEA, another name: 1-methoxy-2-acetoxypropane), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methylpyrrolidone, N,N-dimethylformamide, γ-butyrolactone, N,N-dimethylacetamide, propylene carbonate and ethylene carbonate are preferred. These solvents are used individually or in combination.

The solid component of the resist composition is dissolved in the solvent, and is dissolved at a solid content concentration preferably in a range of 1% by mass to 40% by mass, more preferably of 1% by mass to 30% by mass, and still more preferably of 3% by mass to 20% by mass.

The present invention also relates to a resist film formed by the chemical amplification resist composition of the present invention, and such a resist film is formed by coating, for example, the resist composition on a support such as a substrate. The thickness of the resist film preferably ranges from 0.02 m to 0.1 m. As for the method of coating the resist composition on the substrate, an appropriate coating method such as spin-coating, roll-coating, flow coating, dip coating, spray coating, and doctor coating may be used. The spin-coating is preferred, and the rotational speed preferably ranges from 1000 rpm to 3000 rpm. The coating film is pre-baked at 60° C. to 150° C. for 1 min to 20 min, and preferably at 80° C. to 120° C. for 1 min to 10 min to form a thin film.

As for a material which constitutes a substrate to be processed and its outermost layer, for example, in a case of a wafer for a semiconductor, a silicon wafer may be used, and as an example of a material used as the outermost layer, Si, $SiO_2$, SiN, SiON, TiN, WSi, BPSG, SOG, and an organic antireflection film may be exemplified.

Also, the present invention also relates to resist-coated mask blanks coated with the resist film obtained as described above. When a resist pattern is formed on photomask blanks for manufacturing a photomask in order to obtain such resist-coated mask blanks, for example, a transparent substrate such as quartz and calcium fluoride is used. In general, a light-shielding film, an antireflection film, further a phase shift film, and additionally a required functional film such as an etching stopper film and an etching mask film, are stacked on the substrate. As for the material of the functional film, a film containing silicon or a transition metal such as chromium, molybdenum, zirconium, tantalum, tungsten, titanium and niobium is stacked. As the material used for the outermost layer, a material containing, as a main constituent component, a material which contains silicon or contains silicon and oxygen and/or nitrogen; a silicon compound containing, as a main constituent component, the material described above which further contains a transition metal; and a transition metal compound material containing, as a main constituent component, a material which contains a transition metal, particularly, one or more transition metals selected from chromium, molybdenum, zirconium, tantalum, tungsten, titanium and niobium, or further contains one or more elements selected from oxygen, nitrogen and carbon exemplified.

The light-shielding film may have a single-layer structure but more preferably has a multilayer structure where a plurality of materials are applied one on another. In the case of a multilayer structure, the film thickness per layer is not particularly limited but preferably ranges from 5 nm to 100 nm, more preferably from 10 nm to 80 nm. The thickness of the entire light-shielding film is not particularly limited but preferably ranges from 5 nm to 200 nm, and more preferably from 10 nm to 150 nm.

When pattern formation is performed using a negative-type chemical amplification resist composition on the photomask blanks having the material containing chromium and oxygen or nitrogen in the outermost layer thereof among the materials described above, a so-called undercut shape having a waisted shape near the substrate is likely to be formed in general. However, when the present invention is used, the undercut problem may be improved as compared with the conventional mask blanks.

Subsequently, this resist film is irradiated with an actinic ray or radiation (e.g., electron beam), then preferably baked (usually at 80° C. to 150° C., more preferably from 90° C. to 130° C., usually for 1 min to 20 min, preferably for 1 min to 10 min), and subsequently developed. Accordingly, a good pattern may be obtained. Etching, ion implantation or the like is appropriately performed by using this pattern as the mask to produce, for example, a semiconductor fine circuit, an imprint mold structure, or a photomask.

Meanwhile, the process for preparing an imprint mold by using the composition of the present invention is described, for example, in Japanese Patent No. 4,109,085, Japanese Patent Application Laid-Open No. 2008-162101, and "Basic and Technology Expansion-Application Development of Nanoimprint-Substrate Technology of Nanoimprint and Latest Technology Expansion-edited: Yoshihiko Hirai (Frontier Publishing)."

The usage form of the chemical amplification resist composition of the present invention and the resist pattern forming method will be subsequently described.

The present invention also relates to a resist pattern forming method which includes exposing the resist film or the resist-coated mask blanks, and developing the exposed resist film or resist-coated mask blanks. In the present invention, the exposure is preferably performed using electron beam or extreme UV rays.

In the manufacturing of a precision integrated circuit element, at the exposure on the resist film (a pattern forming step), first, it is preferred to perform irradiation of electron beam or extreme-ultraviolet rays (EUV) on the resist film of the present invention, in a pattern shape. The exposure is performed at an exposure amount ranging from about 0.1 $\mu C/cm^2$ to 20 $\mu C/cm^2$, and preferably from about 3 $\mu C/cm^2$ to 15 $\mu C/cm^2$ in a case of electron beam, and an exposure amount ranging from about 0.1 $mJ/cm^2$ to 20 $mJ/cm^2$ and preferably from about 3 $mJ/cm^2$ to 15 $mJ/cm^2$ in a case of EUV. Then, on a hot plate, the film is subjected to post-exposure baking (PEB) at 60° C. to 150° C. for 1 min to 20 min, preferably at 80° C. to 120° C. for 1 min to 10 min, and then is developed, rinsed and dried to form a resist pattern.

The development is performed using an aqueous alkali solution such as tetramethylammonium hydroxide (TMAH) or tetrabutylammonium hydroxide (TBAH) (preferably 0.1% to 5% by mass, more preferably of 2% to 3% by mass) as for the developer through a conventional method such as a dip method, a puddle method, or a spraying method for preferably 0.1 min to 3 min and more preferably 0.5 min to 2 min. To the alkali developer, alcohols and/or surfactant may be added in an appropriate amount. The pH of the alkali developer generally ranges from 10.0 to 15.0. Particularly, an aqueous solution including 2.38% by mass of tetramethylammoniumhydroxyde is preferred.

As necessary, to the developer, alcohols and/or surfactant may be added in an appropriate amount.

The surfactant is not particularly limited but, for example, ionic or nonionic fluorine-based and/or silicon-based surfactant may be used. Examples of the fluorine and/or silicon-based surfactant may include surfactants described in Japanese Patent Application Laid-Open Nos. S62-36663, S61-226746, S61-226745, S62-170950, S63-34540, H7-230165, H8-62834, H9-54432, and H9-5988, and U.S. Pat. Nos. 5,405,720, 5,360,692, 5,529,881, 5,296,330, 5,436,098, 5,576,143, 5,294,511, and 5,824,451, and a nonionic surfactant is preferred. The nonionic surfactant is not particularly limited, but a fluorine-based surfactant or a silicon-based surfactant is more preferably used.

The amount of the surfactant in use ranges usually from 0.001% by mass to 5% by mass, preferably from 0.005% by mass to 2% by mass, and more preferably from 0.01% by mass to 0.5% by mass, based on the total amount of the developer.

As for the developing method, it is possible to apply, for example, a method of dipping a substrate in a bath filled with a developer for a predetermined time (a dipping method), a method of heaping up a developer on a substrate surface by a surface tension and keeping the substrate still for a fixed time, thereby performing development (a puddle method), a method of spraying a developer on a substrate surface (a spraying method), and a method of continuously ejecting a developer on a substrate spinning at a constant speed while scanning a developer ejecting nozzle at a constant rate (a dynamic dispense method).

When the aforementioned various developing methods include ejecting a developer toward a resist film from a development nozzle of a developing apparatus, the ejection pressure of the ejected developer (the flow velocity per unit area of the ejected developer) is preferably 2 mL/sec/mm$^2$ or less, more preferably 1.5 mL/sec/mm$^2$ or less, and still more preferably 1 mL/sec/mm$^2$ or less. The flow velocity has no particular lower limit, but is preferably 0.2 mL/sec/mm$^2$ or more in consideration of throughput.

By setting the ejection pressure of the ejected developer to the above-described range, pattern defects resulting from the resist residue after development may be significantly reduced.

Details on the mechanism are not clear, but it is thought that it is because by setting the ejection pressure in the above-described range, the pressure imposed on the resist film by the developer is decreased and the resist film or resist film is suppressed from being inadvertently cut or collapsing.

Further, the ejection pressure (mL/sec/mm$^2$) of the developer is the value at the outlet of the development nozzle in the developing apparatus.

Examples of the method for adjusting the ejection pressure of the developer may include a method of adjusting the ejection pressure by, for example, a pump, and a method of supplying a developer from a pressurized tank and adjusting the pressure to change the ejection pressure.

Further, after the step of performing development using a developer, a step of stopping the development while replacing the solvent with another solvent may be performed.

As for the rinsing liquid in the rinse treatment performed after the alkali development, pure water is used, and an appropriate amount of a surfactant may be added to be used.

In this manner, a desired pattern is formed on the substrate in which when the chemical amplification resist composition of the present invention is a negative type composition, a resist film at an unexposed portion is dissolved, and an exposed portion is hardly dissolved in the developer due to crosslinking of a polymer compound, while when the chemical amplification resist composition of the present invention is a positive-type composition, an exposed portion is dissolved in the developer, and an unexposed portion is hardly dissolved in the developer.

The present invention also relates to a photomask obtained by exposing and developing resist-coated mask blanks. As for the exposure and development, the steps described above are applied. The photomask is suitably used for manufacturing a semiconductor.

The photomask in the present invention may be a light transmission type mask used in, for example, ArF excimer laser, or a light reflective mask used in a reflective system lithography using EUV light as a light source.

Also, the present invention also relates to a method of manufacturing a semiconductor device, which includes the above described resist pattern forming method of the present invention, and the semiconductor device manufactured by the manufacturing method.

The semiconductor device of the present invention is suitably mounted in electric/electronic devices (e.g., home appliances, OA-media-related devices, optical devices and communication devices).

EXAMPLE

Hereinafter, the present invention will be described in more detail with reference to examples, but descriptions of the present invention are not limited thereto.

As for compounds represented by Formula (I), compounds B-1, B-2, B-6, B-19, B-22, B-26, B-27 and B-32 were synthesized.

Synthesis of Compound B-1

5.0 g of o-aminothiophenol (manufactured by Wako Pure Chemical Industries, Ltd.) and 5.0 g of pivaloylacetonitrile (manufactured by Tokyo Chemical Industry Co., Ltd.) were mixed with each other and stirred at 120° C. for 2 hours. After cooling, the crude product was purified by silica gel column chromatography to obtain 5.7 g of an intermediate B-1A.

THF (tetrahydrofuran) (3 mL) and B-1A (5.6 g) were mixed with each other, and under ice-cooling, 2M hydrochloric acid/THF solution (24 mL), and then isopentyl nitrite (manufactured by Wako Pure Chemical Industries, Ltd., 3.4 g) were added dropwise thereto. The temperature was raised to a room temperature, and the product was stirred for 2 hours. The resultant reaction mixture was separated through addition of water and ethyl acetate, and the organic layer was washed with water, dried with magnesium sulfate, and filtered and concentrated to obtain a crude intermediate B-1B.

The crude intermediate B-1B was mixed with acetone (20 mL), and under ice-cooling, triethylamine (manufactured by Wako Pure Chemical Industries, Ltd., 4.9 g), and piperidine-1-carbonyl chloride (6.9 g) were added thereto. The temperature was raised to a room temperature, and the product was stirred for 1 hour. The resultant reaction mixture liquid was separated through addition of water and ethyl acetate, and the organic phase was dried with magnesium sulfate, and filtered and concentrated to obtain a crude product B-1. After reslurry with methanol, the crude product B-1 was filtered and dried to obtain a compound B-1 (6.0 g).

Synthesis of Compound B-6

3.0 g of 2-aminophenol (manufactured by Tokyo Chemical Industry Co., Ltd.) and 8.7 g of 4,4-dimethyl-3-oxo methyl valerate (manufactured by Wako Pure Chemical Industries, Ltd.) were mixed with each other, and 0.5 g of p-toluenesulfonic acid monohydrate (manufactured by Wako Pure Chemical Industries, Ltd.) was added thereto, and the mixture was heated under a nitrogen atmosphere at 120° C. for 2 hours. After cooling, the crude product was purified by silica gel column chromatography to obtain 4.4 g of an intermediate B-6A.

B-6A (2.0 g) and p-xylene (10 mL) were mixed with each other, and p-toluenesulfonic acid monohydrate (manufactured by Wako Pure Chemical Industries, Ltd., 0.3 g) was added thereto, and the mixture was heated at 140° C. for 6 hours. After cooling, the reaction mixture liquid was separated through addition of water and ethyl acetate, and the organic phase was dried with magnesium sulfate, and filtered and concentrated to obtain a crude product B-6B.

THF (1.5 mL) and the crude product B-6B (total amount) were mixed with each other, and under ice-cooling, 2M hydrochloric acid/THF solution (8.5 mL), and then isopentyl nitrite (manufactured by Wako Pure Chemical Industries, Ltd., 1.2 g) were added dropwise thereto. The temperature was raised to a room temperature, and the product was stirred for 2 hours. The resultant reaction mixture was separated through addition of water and ethyl acetate, and the organic layer was washed with water, dried with magnesium sulfate, and filtered and concentrated to obtain a crude intermediate B-6C.

The crude intermediate B-6C (1.0 g) was mixed with acetone (10 mL), and under ice-cooling, triethylamine (manufactured by Wako Pure Chemical Industries, Ltd.) (0.74 g), and piperidine-1-carbonyl chloride (manufactured by Tokyo Chemical Industry Co., Ltd.) (2.0 g) were added thereto. The temperature was raised to a room temperature and the product was stirred for 1 hour. The resultant reaction mixture liquid was separated through addition of water and ethyl acetate, and the organic phase was dried with magnesium sulfate, and filtered and concentrated to obtain a crude product B-6. After reslurry with methanol, the crude product B-6 was filtered and dried to obtain a compound B-6 (1.0 g).

Synthesis of Compound B-19

5.0 g of 1-(1-naphthyl)-2-thiourea (manufactured by Wako Pure Chemical Industries, Ltd.) was suspended in 100 mL of acetic acid, and 9.6 g of benzyltrimethylammonium tribromide (manufactured by Tokyo Chemical Industry Co., Ltd.) was dividedly added thereto, followed by stirring at a room temperature for 8 hours. The reaction mixture liquid was dropped to a saturated aqueous solution of sodium bicarbonate (1.6 L) in an ice bath, and was separated with ethyl acetate (300 mL), and the organic phase was dried with magnesium sulfate, and filtered and concentrated to obtain a crude product B-19A (4.9 g).

The resultant crude product B-19A (4.9 g) was added to ethylene glycol (50 mL), and 50% aqueous solution of sodium hydroxide (12.2 g) was added thereto, followed by heating at reflux under a nitrogen atmosphere for 48 hours. After cooling, the reaction mixture liquid was added to a mixture liquid of acetic acid (40 mL) and water (120 mL) under ice-cooling, and separated with diethyl ether (150 mL). The organic phase was dried with magnesium sulfate, and filtered and concentrated to obtain a crude product B-19B.

The obtained crude product B-19B (total amount) was mixed with pivaloylacetonitrile (manufactured by Tokyo Chemical Industry Co., Ltd.), and stirred at 140° C. for 6 hours. After cooling, the crude product was purified by silica gel column chromatography to obtain 2.1 g of an intermediate B-19C.

THF (3 mL) and B-19C (2.0 g) were mixed with each other, and under ice-cooling, 2M hydrochloric acid/THF solution (7.1 mL), and then isopentyl nitrite (manufactured by Wako Pure Chemical Industries, Ltd.) (1.0 g) were added dropwise thereto. The temperature was raised to a room temperature, and the product was stirred for 2 hours. The resultant reaction mixture was separated through addition of water and ethyl acetate, and the organic layer was washed with water, dried with magnesium sulfate, and filtered and concentrated to obtain a crude intermediate B-19D.

The crude intermediate B-19D was mixed with acetone (10 mL), and under ice-cooling, trimethylamine (manufactured by Wako Pure Chemical Industries, Ltd.) (1.1 g), and piperidine-1-carbonyl chloride (2.35 g) were added thereto. The temperature was raised to a room temperature, and the product was stirred for 1 hour. The resultant reaction mixture liquid was separated through addition of water and ethyl acetate, and the organic phase was dried with magnesium sulfate, and filtered and concentrated to obtain a crude product B-19. After reslurry with cold methanol, the crude product B-19 was filtered and dried to obtain a compound B-19 (1.7 g). Compounds B-2, B-22, B-26, B-27 and B-32 were synthesized in the same manner.

The compounds used in Comparative Examples are noted in Table 1 below.

TABLE 1

| Compound | Chemical formula |
|---|---|
| Comparative Compound (AC1) | tri(n-octyl)amine |
| Comparative Compound (AC2) | [structure: phthalimide-N-O-C(=O)-HN-$C_8H_{17}$] |
| Comparative Compound (AC3) | [structure: fluorenone oxime derivative with dimethoxyphenyl carbamate] |
| Comparative Compound (AC4) | [structure: benzaldehyde oxime benzoate] |
| Comparative Compound (AC5) | [structure: benzoxazole ketoxime piperidine-1-carboxylate] |

Example 1P

Electron Beam Exposure; Positive-Type (1) Preparation of Support

An oxidized Cr-deposited 6-inch wafer (which had been subjected to shielding-film treatment used for conventional photomask blanks) was prepared.

(2) Preparation of Resist Coating Liquid
(Composition of Coating Liquid of Positive-Type Chemical Amplification Resist Composition P1)

| | |
|---|---|
| Polymer compound (P-4) | 0.60 g |
| Photo-acid generator z5 (structural formula below) | 0.12 g |
| Compound of the present invention (B-1) | 0.02 g |
| Surfactant PF6320 (manufactured by OMNOVA Co., Ltd.) | 0.001 g |
| Propylene glycol monomethyl ether acetate (solvent) | 18.0 g |

The composition solution was finely filtered with a polytetrafluoroethylene filter having a pore diameter of 0.04 m to obtain a resist coating solution with a solid concentration of 3.95% by mass.

(3) Preparation of Resist Film

On the 6-inch wafer, a resist coating solution was coated using a spin coater Mark8 (manufactured by Tokyo Electron Limited), and dried at 110° C. for 90 sec on a hot plate to obtain a resist film with a film thickness of 50 nm. That is, resist-coated mask blanks were obtained.

(4) Manufacturing of Positive-Type Resist Pattern

On the resist film, pattern irradiation was performed using an electron beam drawing apparatus (manufactured by ELIONIX INC.; ELS-7500, an acceleration voltage 50 KeV). After the irradiation, the film was heated at 120° C. for 90 sec on a hot plate, immersed in 2.38% by mass of aqueous tetramethylammonium hydroxide (TMAH) solution for 60 sec, rinsed with water for 30 sec, and dried.

(5) Evaluation of Resist Pattern

On the obtained pattern, the sensitivity, resolution, pattern shape, line edge roughness (LER), scum and temporal stability of a resist composition were evaluated by the following methods.

[Sensitivity]

The cross-sectional shape of the resultant pattern was observed using a scanning electron microscope (S-4300 manufactured by Hitachi Ltd.). The exposure amount (electron beam irradiation dose) when resolving a resist pattern with a line width of 50 nm (line:space=1:1) was set as sensitivity. A smaller value indicates a higher sensitivity.

[Resolution Evaluation (LS)]

The limiting resolution (the minimum line width when the line and space were separated and resolved) at the exposure amount (electron beam irradiation dose) exhibiting the sensitivity was set as LS resolution.

[Resolution Evaluation (IL)]

The limiting resolution (the minimum line width when the line and space were separated and resolved) at a minimum irradiation dose when resolving an isolated line pattern with a line width of 50 nm (line:space=1:>100) was set as IL resolution (nm).

[Pattern Shape]

The cross-sectional shape of the resist pattern with a line width of 50 nm (line:space=1:1) at the exposure amount (electron beam irradiation dose) exhibiting the sensitivity was observed by a scanning electron microscope (S-4300, manufactured by Hitachi Ltd.). The cross-sectional shape of the line pattern was rated "forward taper" when the ratio represented by [line width in the bottom portion of line pattern/line width in the middle portion of line pattern (the position of half the height of line pattern)] is 1.5 or more, rated "slightly forward taper" when the ratio above is 1.2 or more and less than 1.5, and rated "rectangle" when the ratio above is less than 1.2.

[Line Edge Roughness (LER)]

A resist pattern having a line width 50 nm (line:space=1:1) was formed with the exposure amount (electron beam irradiation dose) exhibiting the sensitivity. Then, at arbitrary 30 points included in its longitudinal 50 µm region, the distance from a reference line where the edge should be present was measured using a scanning electron microscope (S-9220 manufactured by Hitachi Ltd.). Then, the standard deviation of the measured distances was determined, and 30 was calculated. A smaller value indicates a better performance.

[Scum Evaluation]

The line pattern was formed by the same method as described above in the [pattern shape]. Then, the cross-sectional SEM was acquired by S4800 (manufactured by Hitachi High-Technologies Corporation), and the residue in the space portion was observed and evaluated as follows.

AA: scum is not seen.
A: scum is seen but connection is not present between patterns.
B: scum is seen and connection is partially present between patterns.

[Temporal Stability of Resist Composition]

After each composition was stored at a room temperature for 1 month, a degree of fluctuation in the sensitivity (in the sensitivity measured in the [Sensitivity] above) before and after the storage was evaluated. This evaluation was based on the following criteria.

(Evaluation Criteria)

A (Good): when fluctuation of sensitivity is less than 1 µC/cm²
B (Fair): when fluctuation of sensitivity is 1 µC/cm² or more and 3 µC/cm² or less
C (Insufficient): when fluctuation of sensitivity is higher than 3 µC/cm².

[Example 2P] to [Example 17P], [Comparative Example 1P] to [Comparative Example 5P]

By resist liquid prescription, preparation of a resist solution with a solid concentration of 3.84% by mass (positive-type resist compositions P2 to P17, positive-type resist comparative compositions P1 to P5), formation of a positive-type pattern, and evaluations thereof were performed in the same manner as in Example 1P except for the components noted in Table 2 and 3 below.

TABLE 2

(electron beam exposure; positive-type)

| Composition | Acid generator (0.12 g) | Resin (C) (0.60 g) | Photobase generator (0.02 g) | Surfactant (0.001 g) | Solvent (parts by mass) (18.0 g) |
|---|---|---|---|---|---|
| P1 | z5 | P-4 | B-1 | W-1 | S1 |
| P2 | z5 | P-4 | B-6 | W-1 | S1/S2 (6/4) |
| P3 | z5 | P-4 | B-19 | W-1 | S1/S2 (6/4) |
| P4 | z5 | P-4 | B-22 | W-1 | S1/S2 (6/4) |
| P5 | z5 | P-4 | B-26 | W-1 | S1/S2 (6/4) |
| P6 | z5 | P-4 | B-27 | W-1 | S1/S2 (6/4) |
| P7 | z5 | P-4 | B-32 | W-1 | S1/S2 (6/4) |

TABLE 2-continued (electron beam exposure; positive-type)

| Composition | Acid generator (0.12 g) | Resin (C) (0.60 g) | Photobase generator (0.02 g) | Surfactant (0.001 g) | Solvent (parts by mass) (18.0 g) |
|---|---|---|---|---|---|
| P8 | z8 | P-1 | B-1 | W-1 | S1/S2 (6/4) |
| P9 | z63 | P-2 | B-1 | W-1 | S1/S2 (6/4) |
| P10 | z65 | P-3 | B-1 | W-1 | S1/S2 (6/4) |
| P11 | z67 | P-5 | B-1 | W-2 | S1/S2 (6/4) |
| P12 | z48 | P-6 | B-1 | W-3 | S1/S2 (6/4) |
| P13 | z68 | P-7 | B-1 | — | S1/S4 (6/4) |
| P14 | z68 | P-8 | B-1 | — | S1/S3 (6/4) |
| P15 | z61 | P-9/P-5 (0.3 g/ 0.3 g) | B-1 | — | S1/S5 (6/4) |
| P16 | z49 | P-10 | B-1 | W-1 | S1/S5 (6/4) |
| P17 | z2/z66 (0.06 g/ 0.06 g) | P-11 | B-1/B-6 (0.01 g/ 0.01 g) | W-1 | S1/S5 (6/4) |

TABLE 3

(subsequent to Table 2)

| Composition | Acid generator (0.12 g) | Resin (C) (0.60 g) | Photobase generator (0.02 g) | Surfactant (0.001 g) | Solvent (mass ratio) (18.0 g) |
|---|---|---|---|---|---|
| Comparative Composition P1 | z48 | P-1 | AC1 | W-1 | S1/S2 (6/4) |
| Comparative Composition P2 | z48 | P-1 | AC2 | W-1 | S1/S2 (6/4) |
| Comparative Composition P3 | z48 | P-1 | AC3 | W-1 | S1/S2 (6/4) |
| Comparative Composition P4 | z48 | P-1 | AC4 | W-1 | S1/S2 (6/4) |
| Comparative Composition P5 | z48 | P-1 | AC5 | W-1 | S1/S2 (6/4) |

The abbreviations of materials used by Examples or Comparative Examples above, other than those described above, are indicated below. Meanwhile, in the description of resin (C), the structure, repeating unit composition ratio (molar ratio), weight average molecular weight and polydispersity of the resin will be described below.

[Acid Generator (Compound (B))]

[Chem. 60]

(z2)

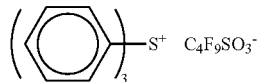

113 Å³

(z5)

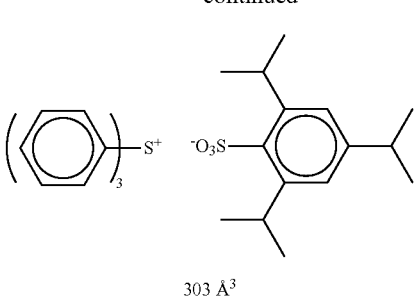

303 Å³

(z8)

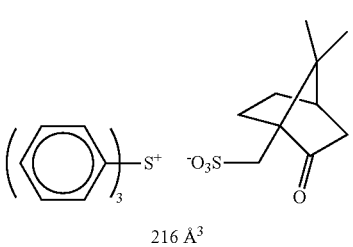

216 Å³

(z37)

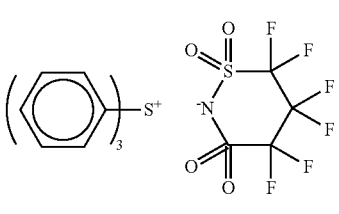

136 Å³

(z42)

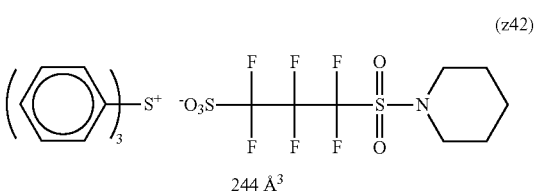

244 Å³

(z45)

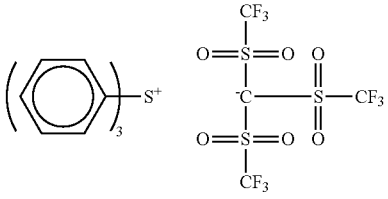

189 Å³

(z48)

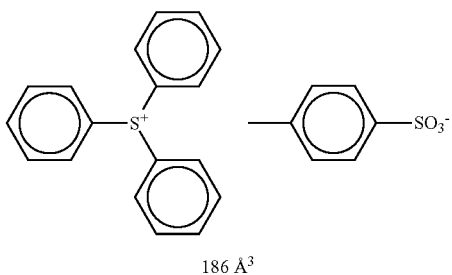

186 Å³

(z49)
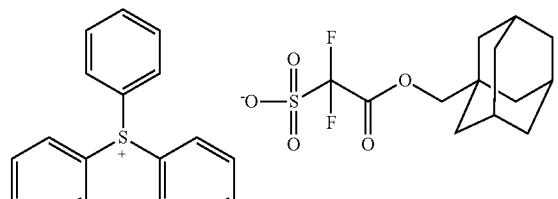
271 Å³
(z61)
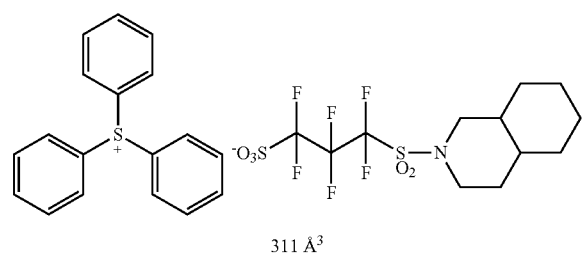
311 Å³
(z63)
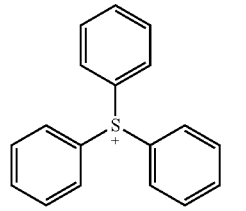
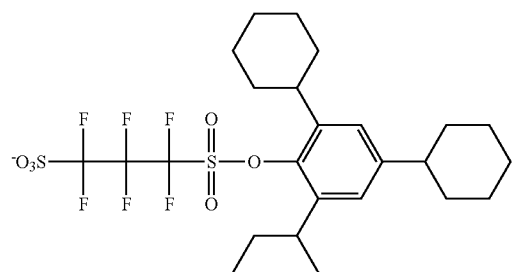
535 Å³
(z65)
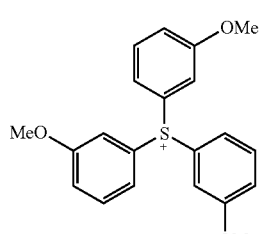
437 Å³
(z66)
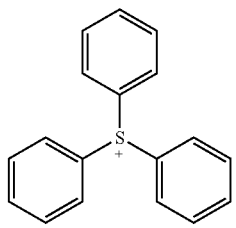
127 Å³
(z67)
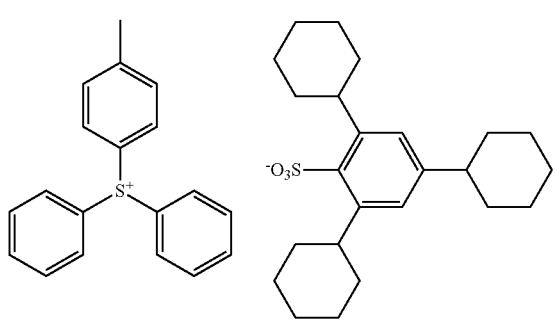
437 Å³
(z68)
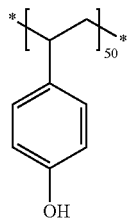
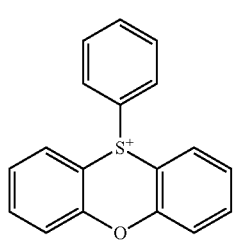
437 Å³
[Resin (C)]
[Chem. 61]
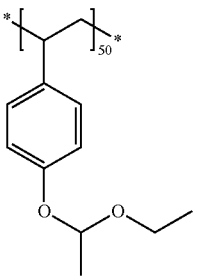
P-1
Mw = 12000
Mw/Mn = 1.2

P-2
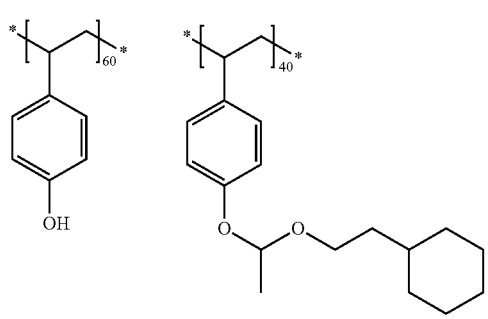
Mw = 4800
Mw/Mn = 1.2
P-3
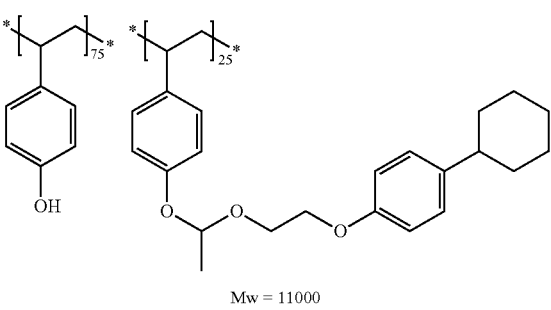
Mw = 11000
Mw/Mn = 1.1
P-4
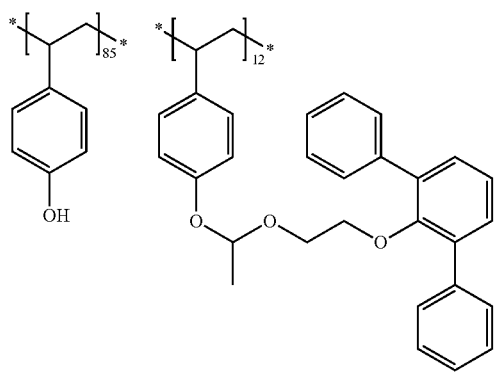
P-4
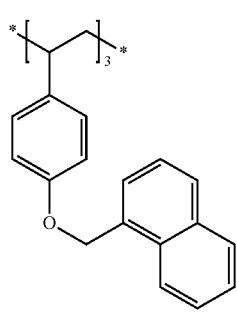
Mw = 11000
Mw/Mn = 1.1
P-5
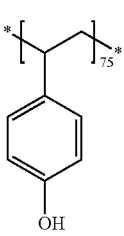
Mw = 4800
Mw/Mn = 1.2
P-6
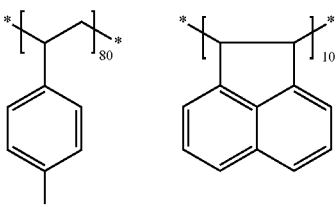
P-6
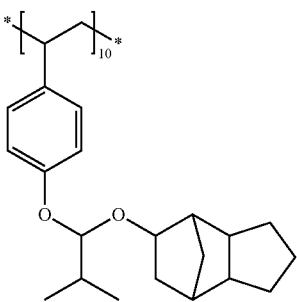
Mw = 5500
Mw/Mn = 1.5
P-7
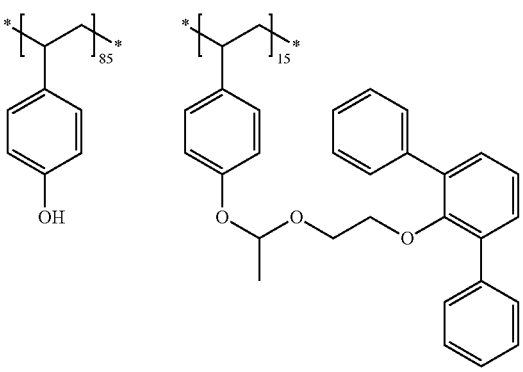
Mw = 10000
Mw/Mn = 1.1

-continued

P-8

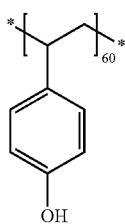
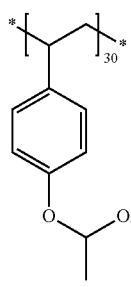

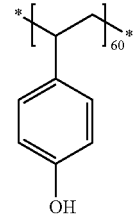
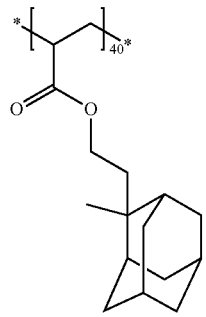

Mw = 5700
Mw/Mn = 1.3

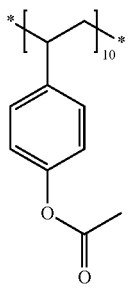

Mw = 4800
Mw/Mn = 1.1

P-11

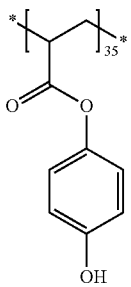
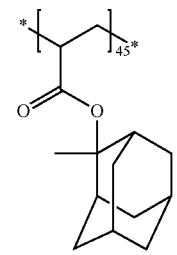

Mw = 6500
Mw/Mn = 1.3

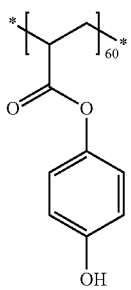

Mw = 4800
Mw/Mn = 1.3

P-9

[Surfactant]
W-1: PF6320 (manufactured by OMNOVA Co., Ltd.)
W-2: MEGAFAC F176 (manufactured by DIC Corporation; fluorine-based)
W-3: Polysiloxane polymer KP-341 (manufactured by Shin-Etsu Chemical Co., Ltd.; silicon-based)
[Solvent]
S1: Propylene glycol monomethyl ether acetate (1-methoxy-2-acetoxypropane)
S2: propylene glycol monomethyl ether (1-methoxy-2-propanol)
S3: 2-heptanone
S4: ethyl lactate
S5: cyclohexanone
S6: γ-butyrolactone
S7: propylene carbonate The evaluation results are noted in Table 4.

TABLE 4

(electron beam exposure; positive-type)

| Example | Composition | Sensitivity ($\mu C/cm^2$) | LS resolution (nm) | IL resolution (nm) | Pattern shape | LER (nm) | Scum | Temporal stability |
|---|---|---|---|---|---|---|---|---|
| 1P | P1 | 15.8 | 25 | 30 | rectangle | 4.0 | AA | A |
| 2P | P2 | 15.9 | 25 | 30 | rectangle | 4.0 | AA | A |
| 3P | P3 | 15.7 | 25 | 30 | rectangle | 4.0 | AA | A |
| 4P | P4 | 15.7 | 25 | 30 | rectangle | 4.0 | AA | A |
| 5P | P5 | 15.8 | 30 | 30 | rectangle | 4.5 | AA | B |
| 6P | P6 | 15.8 | 30 | 30 | rectangle | 4.5 | AA | B |
| 7P | P7 | 15.7 | 25 | 30 | rectangle | 4.0 | AA | A |
| 8P | P8 | 15.8 | 25 | 30 | rectangle | 4.0 | AA | A |
| 9P | P9 | 15.9 | 25 | 30 | rectangle | 4.0 | AA | A |
| 10P | P10 | 15.8 | 25 | 30 | rectangle | 4.0 | AA | A |
| 11P | P11 | 15.8 | 25 | 30 | rectangle | 4.0 | AA | A |
| 12P | P12 | 15.8 | 25 | 35 | rectangle | 4.5 | AA | A |
| 13P | P13 | 15.7 | 25 | 30 | rectangle | 4.0 | AA | A |
| 14P | P14 | 15.8 | 25 | 30 | rectangle | 4.0 | AA | A |
| 15P | P15 | 15.8 | 25 | 30 | rectangle | 4.0 | AA | A |

TABLE 4-continued (electron beam exposure; positive-type)

| Example | Composition | Sensitivity ($\mu C/cm^2$) | LS resolution (nm) | IL resolution (nm) | Pattern shape | LER (nm) | Scum | Temporal stability |
|---|---|---|---|---|---|---|---|---|
| 16P | P16 | 15.6 | 25 | 30 | rectangle | 4.0 | AA | A |
| 17P | P17 | 15.8 | 25 | 35 | rectangle | 4.5 | AA | A |
| Comparative Example 1P | Comparative composition P1 | 15.9 | 40 | 50 | forward taper | 5.5 | B | A |
| Comparative Example 2P | Comparative composition P2 | 15.9 | 40 | 50 | slightly forward taper | 5.0 | A | C |
| Comparative Example 3P | Comparative composition P3 | 15.9 | 40 | 50 | slightly forward taper | 5.0 | A | C |
| Comparative Example 4P | Comparative composition P4 | 15.9 | 40 | 50 | slightly forward taper | 5.0 | A | C |
| Comparative Example 5P | Comparative composition P5 | 15.8 | 40 | 50 | slightly forward taper | 5.0 | A | C |

As clearly found from the results noted in Table 4, Comparative Examples 1P to 5P which did not use the compound represented by Formula (I) were poor in the resolution, pattern shape, and LER performance. Comparative Example 1P was poor in the scum performance, and Comparative Examples 2P to 5P were poor in the temporal stability of a resist composition.

Meanwhile, it was found that Examples 1P to 17P which used the compound represented by Formula (I) were excellent in particularly the scum reduction, and excellent in the resolution, pattern shape and LER performance.

Examples 1Q to 5Q and Comparative Examples 1Q to 5Q

Preparation of Resist Solution

The positive-type resist composition described in Table 5 below was filtered with a polytetrafluoroethylene filter having a pore diameter of 0.04 m to prepare a positive-type resist solution with a solid concentration of 3.84% by mass.
(Resist Evaluation)

The prepared positive-type resist solution was uniformly coated using a spin coater, on a silicon substrate subjected to a hexamethyldisilazane treatment, and heated and dried at 100° C. for 60 sec on a hot plate to form a resist film with a film thickness of 50 nm.

On the obtained resist film, the sensitivity, resolution, pattern shape, line edge roughness (LER), scum and temporal stability of a resist composition were evaluated by the following methods.
[Sensitivity]

The obtained resist film was exposed by using EUV light (wavelength 13 nm) through a reflective mask of a 1:1-line&space pattern with a line width of 50 nm while changing an exposure amount by 0.1 mJ/cm² each time in a range of 0 to 20.0 mJ/cm², and then baked at 110° C. for 90 sec. Then, the film was developed using 2.38% by mass of tetramethylammonium hydroxide (TMAH) aqueous solution.

The exposure amount reproducing the mask pattern of a 1:1-line&space with a line width of 50 nm was set as sensitivity. A smaller value indicates a higher sensitivity.
[Resolution]

The limiting resolution (the minimum line width when the line and space were separated and resolved) at the exposure amount exhibiting the sensitivity was set as resolution (nm).

[Pattern Shape]

The cross-sectional shape of the resist pattern with a line width of 50 nm (line:space=1:1) at the exposure amount exhibiting the sensitivity was observed by a scanning electron microscope (S-4300, manufactured by Hitachi Ltd.). The cross-sectional shape of the line pattern was rated "forward taper" when the ratio represented by [line width in the bottom portion of line pattern/line width in the middle portion of line pattern (the position of half the height of line pattern)] is 1.5 or more, rated "slightly forward taper" when the ratio above is 1.2 or more and less than 1.5, and rated "rectangle" when the ratio above is less than 1.2.
[Line Edge Roughness (LER)]

A resist pattern having a line width 50 nm (line:space=1:1) was formed with the exposure amount exhibiting the sensitivity. Then, at arbitrary 30 points included in its longitudinal 50 μm region, the distance from a reference line where the edge should be present was measured using a scanning electron microscope (S-9220 manufactured by Hitachi Ltd.). Then, the standard deviation of the measured distances was determined, and 30 was calculated. A smaller value indicates a better performance.
[Temporal Stability of Resist Composition]

After each composition was stored at 25° C. for 1 month, a degree of fluctuation in the sensitivity (in the sensitivity measured in the [Sensitivity] above) before and after the storage was evaluated. This evaluation was based on the following criteria.
(Evaluation Criteria)
A (Good): when fluctuation of sensitivity is less than 1 mJ/cm²
B (Fair): when fluctuation of sensitivity is 1 mJ/cm² or more and 3 mJ/cm² or less
C (Insufficient): when fluctuation of sensitivity is higher than 3 mJ/cm².
[Scum Evaluation]

The line pattern was formed by the same method as described above in the [pattern shape]. Then, the cross-sectional SEM was acquired by S4800 (manufactured by Hitachi High-Technologies Corporation), and the residue in the space portion was observed and evaluated as follows.
AA: scum is not seen.
A: scum is seen but connection is not present between patterns.
B: scum is seen and connection is partially present between patterns.

The evaluation results are noted in Table 5.

TABLE 5

(EUV exposure; positive-type)

| Example | Composition | Sensitivity (mJ/cm²) | Resolution (nm) | Pattern shape | LER (nm) | Scum | Temporal stability |
|---|---|---|---|---|---|---|---|
| 1Q | P1 | 10.8 | 25 | rectangle | 4.0 | AA | A |
| 2Q | P2 | 10.8 | 25 | rectangle | 4.0 | AA | A |
| 3Q | P3 | 10.8 | 25 | rectangle | 4.0 | AA | A |
| 4Q | P4 | 10.7 | 25 | rectangle | 4.0 | AA | A |
| 5Q | P5 | 10.8 | 30 | rectangle | 4.5 | AA | B |
| Comparative Example 1Q | Comparative composition P1 | 10.9 | 40 | forward taper | 5.5 | B | A |
| Comparative Example 2Q | Comparative composition P2 | 10.9 | 40 | slightly forward taper | 5.0 | A | C |
| Comparative Example 3Q | Comparative composition P3 | 10.9 | 40 | slightly forward taper | 5.0 | A | C |
| Comparative Example 4Q | Comparative composition P4 | 10.9 | 40 | slightly forward taper | 5.0 | A | C |
| Comparative Example 5Q | Comparative composition P5 | 10.7 | 40 | slightly forward taper | 5.0 | A | C |

As clearly found from the results noted in Table 5, Comparative Examples 1Q to 5Q which did not use the compound represented by Formula (I) were poor in the sensitivity, resolution, pattern shape and LER performance. Comparative Example 1Q was poor in the scum reduction, and Comparative Examples 2Q to 5Q were poor in the temporal stability of a resist composition.

Meanwhile, it was found that Examples 1Q to 5Q which used the compound represented by Formula (I) were excellent in particularly the scum reduction, and excellent in the sensitivity, resolution, pattern shape and LER performance.

Examples 1E to 15E and Comparative Examples 1E to 5E

Electron Beam Exposure; Negative Type (1) Preparation of Support

An oxidized Cr-deposited 6-inch wafer (which had been subjected to shielding-film treatment used for conventional photomask blanks) was prepared.

(2) Preparation of Resist Coating Liquid (Composition of Coating Liquid of Negative-Type Chemical Amplification Resist Composition N1)

| | |
|---|---|
| Photo-acid generator (z61) (structural formula below) | 0.47 g |
| Compound (P4)(structural formula below) | 4.68 g |
| Crosslinking agent CL-1 (structural formula below) | 0.59 g |
| Crosslinking agent CL-4 (structural formula below) | 0.30 g |
| Compound of the present invention (B-1) | 0.04 g |
| 2-hydroxy-3-naphthoic acid (organic carboxylic acid) | 0.11 g |
| Surfactant PF6320 (manufactured by OMNOVA Co., Ltd.) | 0.005 g |
| Propylene glycol monomethyl ether acetate (solvent) | 18.8 g |
| Propylene glycol monomethyl ether (solvent) | 75.0 g |

[Chem. 62]

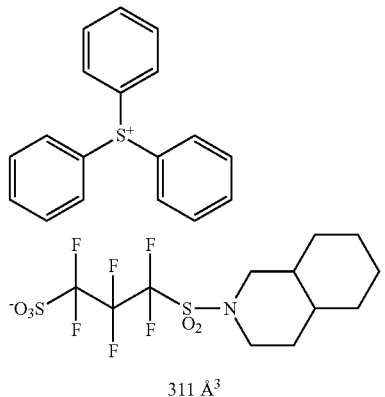

(z61)

311 Å³

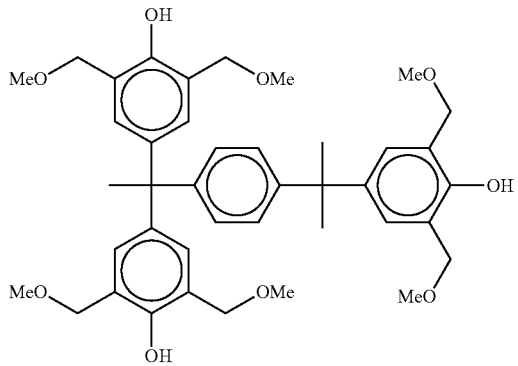

CL-1

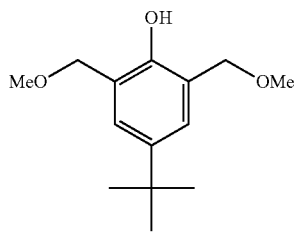

CL-4

The composition solution was finely filtered with a polytetrafluoroethylene filter having a pore diameter of 0.04 m to obtain a resist coating solution.

By resist liquid prescription, negative-type chemical amplification resist compositions N2 to N15, and negative-type chemical amplification resist comparative compositions N1 to N5 were prepared in the same manner as described in the negative-type chemical amplification resist composition N1 except that the components noted in Tables 6 and 7 below were used.

TABLE 6

| Composition | Phenolic hydroxyl group-containing compound (4.68 g) | Photo-acid generator (0.47 g) | Organic carboxylic acid (0.11 g) | Photobase generator (0.04 g) | Surfactant (0.005 g) | Crosslinking agent (0.89 g) | Solvent (93.8 g) |
|---|---|---|---|---|---|---|---|
| N1 | P4 | z61 | D1 | B-1 | W-1 | CL-1/CL-4 (0.59 g/0.30 g) | S2/S1 (75.0 g/18.8 g) |
| N2 | P4 | z61 | D1 | B-6 | W-1 | CL-1/CL-4 (0.59 g/0.30 g) | S1/S3 (75.0 g/18.8 g) |
| N3 | P4 | z61 | D1 | B-19 | W-1 | CL-1/CL-4 (0.59 g/0.30 g) | S2/S3 (75.0 g/18.8 g) |
| N4 | P4 | z61 | D1 | B-22 | W-1 | CL-1/CL-4 (0.59 g/0.30 g) | S2/S7 (75.0 g/18.8 g) |
| N5 | P4 | z61 | D1 | B-26 | W-1 | CL-1/CL-4 (0.59 g/0.30 g) | S2/S1 (75.0 g/18.8 g) |
| N6 | P4 | z61 | D1 | B-27 | W-1 | CL-1/CL-4 (0.59 g/0.30 g) | S2/S1 (75.0 g/18.8 g) |
| N7 | P4 | z61 | DI | B-32 | W-1 | CL-1/CL-4 (0.59 g/0.30 g) | S2/S1 (75.0 g/18.8 g) |
| N8 | P4 | z63 | DI | B-1 | W-2 | CL-1/CL-4 (0.59 g/0.30 g) | S2/S1 (75.0 g/18.8 g) |
| N9 | P4 | z66 | D1 | B-1 | W-3 | CL-1/CL-4 (0.59 g/0.30 g) | S2/S1 (75.0 g/18.8 g) |
| N10 | P4 | z49 | D2 | B-1 | W-1 | CL-1/CL-4 (0.59 g/0.30 g) | S2/S1 (75.0 g/18.8 g) |
| N11 | P1 | z45 | D1 | B-1 | — | CL-1/CL-4 (0.59 g/0.30 g) | S2/S1 (75.0 g/18.8 g) |
| N12 | P2 | z42 | DI | B-1 | — | CL-1/CL-4 (0.59 g/0.30 g) | S1/S2/S6 (50.0 g/25.0 g/18.8 g) |
| N13 | P3/P4 (2.0 g/2.68 g) | z5 | D1 | B-1 | — | CL-1/CL-4 (0.59 g/0.30 g) | S1/S2/S5 (50.0 g/25.0 g/18.8 g) |
| N14 | P5 | z37 | D2 | B-1 | — | CL-2/CL-5 (0.59 g/0.30 g) | S1/S2/S4 (50.0 g/25.0 g/18.8 g) |
| N15 | P4/P6 (2.0 g/2.68 g) | z2/z8 (0.2 g/0.27 g) | D3 | B-2/B-1 (0.02 g/0.02 g) | — | CL-1/CL-4 (0.59 g/0.30 g) | S2/S1 (75.0 g/18.8 g) |

TABLE 7

(subsequent to Table 6)

| Composition | Phenolic hydroxyl group-containing compound (4.68 g) | Photo-acid generator (0.47 g) | Organic carboxylic acid (0.11 g) | Photobase generator (0.04 g) | Surfactant (0.005 g) | Crosslinking agent (0.89 g) | Solvent (93.8 g) |
|---|---|---|---|---|---|---|---|
| Comparative composition N1 | P2 | z2 | D1 | AC1 | W-1 | CL-3 | S1 |
| Comparative composition N2 | P2 | z2 | D1 | AC2 | W-1 | CL-3 | S1 |
| Comparative composition N3 | P2 | z2 | D1 | AC3 | W-1 | CL-3 | S1 |
| Comparative composition N4 | P2 | z2 | D1 | AC4 | W-1 | CL-3 | S1 |
| Comparative composition N5 | P2 | z2 | D1 | AC5 | W-1 | CL-3 | S1 |

The abbreviations of materials used by Examples or Comparative Examples above, other than those described above, are indicated below. Meanwhile, in the description of a phenolic hydroxyl group-containing compound (E), the structural formula of the compound (E) will be described below. When the compound (E) is a resin, the repeating unit composition ratio (molar ratio), weight average molecular weight and polydispersity of the resin will be described below.

[Phenolic Hydroxyl Group-Containing Compound (Compound (E))]

[Chem. 63]

P1

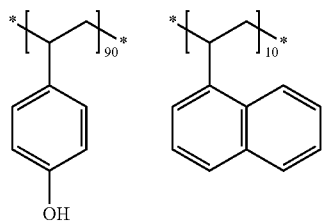

Mw = 1200
Mw/Mn = 2.3

P2

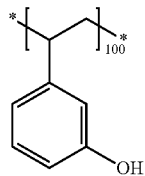

Mw = 4500
Mw/Mn = 1.1

P3

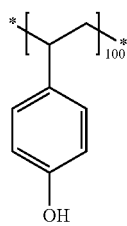

Mw = 3700
Mw/Mn = 1.1

P4

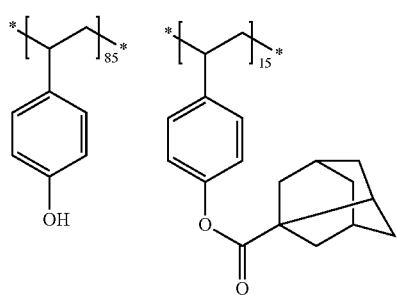

Mw = 4200
Mw/Mn = 1.1

P5

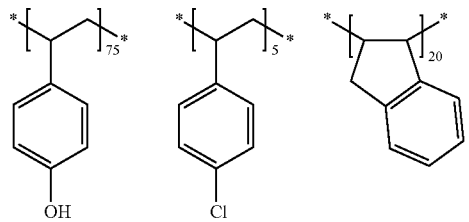

Mw = 4500
Mw/Mn = 1.5

P6

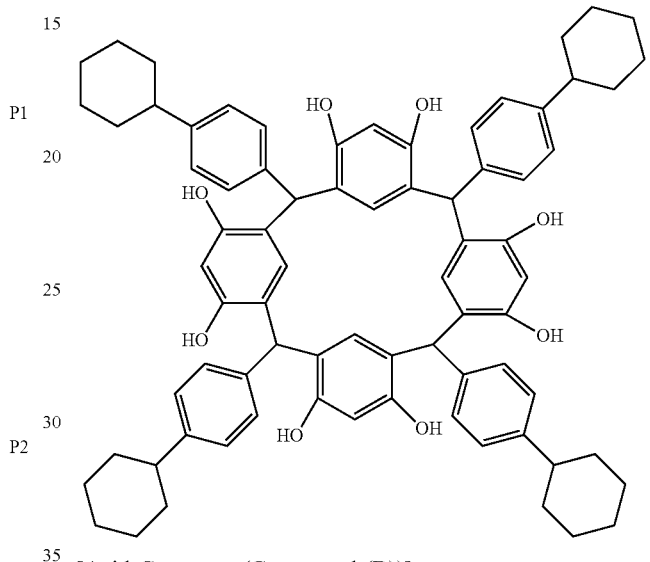

[Acid Generator (Compound (B))]

The acid generator (compound (B)) is the same as described above.

[Crosslinking Agent (Compound (D))]

[Chem. 64]

CL-1

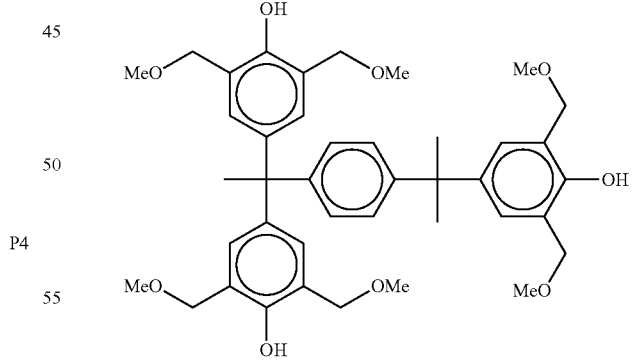

CL-2

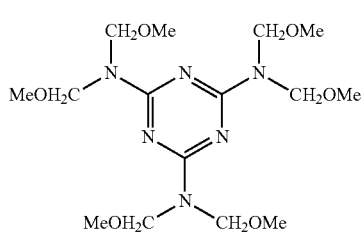

-continued

CL-3

CL-4

[Chem. 65]

CL-5

[Basic Compound]

Basic compounds (B-1), (B-2), (B-6), (B-19), (B-22), (B-26), (B-27) and (B-32) are the same as described above.

[Organic Carboxylic Acid]

D1: 2-hydroxy-3-naphthoic acid
D2: 2-naphthoic acid
D3: benzoic acid

[Surfactant]

Surfactants (W-1) to (W-3) are the same as described above.

[Solvent]

Solvents (S1) to (S7) are the same as described above.

(3) Preparation of Resist Film

On the 6-inch wafer, a resist coating solution was coated using a spin coater Mark8 (manufactured by Tokyo Electron Limited), and dried at 110° C. for 90 sec on a hot plate to obtain a resist film with a film thickness of 100 nm. That is, resist-coated mask blanks were obtained.

(4) Manufacturing of Negative-Type Resist Pattern

On the resist film, pattern irradiation was performed using an electron beam drawing apparatus (manufactured by ELIONIX INC.; ELS-7500, an acceleration voltage 50 KeV). After the irradiation, the film was heated at 120° C. for 90 sec on a hot plate, immersed in 2.38% by mass of aqueous tetramethylammonium hydroxide (TMAH) solution for 60 sec, rinsed with water for 30 sec, and dried.

(5) Evaluation of Resist Pattern

On the obtained pattern, the sensitivity, resolution, pattern shape, line edge roughness (LER), scum and temporal stability of a resist composition were evaluated by the following methods.

[Sensitivity]

The cross-sectional shape of the resultant pattern was observed using a scanning electron microscope (S-4300 manufactured by Hitachi Ltd.). The exposure amount (electron beam irradiation dose) when resolving a resist pattern with a line width of 50 nm (line:space=1:1) was set as sensitivity. A smaller value indicates a higher sensitivity.

[Resolution]

The limiting resolution (the minimum line width when the line and space were separated and resolved (line:space=1:1)) at the exposure amount (electron beam irradiation dose) exhibiting the sensitivity was set as resolution (nm).

[Pattern Shape]

The cross-sectional shape of the resist pattern with a line width of 50 nm (line:space=1:1) at the exposure amount (electron beam irradiation dose) exhibiting the sensitivity was observed by a scanning electron microscope (S-4300, manufactured by Hitachi Ltd.). The cross-sectional shape of the line pattern was rated "inverse taper" when the ratio represented by [line width in the top portion (surface portion) of line pattern/line width in the middle portion of line pattern (the position of half the height of line pattern)] is 1.5 or more, rated "slightly inverse taper" when the ratio above is 1.2 or more and less than 1.5, and rated "rectangle" when the ratio above is less than 1.2.

[Line Edge Roughness (LER)]

A resist pattern having a line width 50 nm (line:space=1:1) was formed with the exposure amount (electron beam irradiation dose) exhibiting the sensitivity. Then, at arbitrary 30 points included in its longitudinal 50 μm region, the distance from a reference line where the edge should be present was measured using a scanning electron microscope (S-9220 manufactured by Hitachi Ltd.). Then, the standard deviation of the measured distances was determined, and 3σ was calculated. A smaller value indicates a better performance.

[Scum Evaluation]

The line pattern was formed by the same method as described above in the [pattern shape]. Then, the cross-sectional SEM was acquired by S4800 (manufactured by Hitachi High-Technologies Corporation), and the residue in the space portion was observed and evaluated as follows.

AA: scum is not seen.

A: scum is seen but connection is not present between patterns.

B: scum is seen and connection is partially present between patterns.

[Temporal Stability of Resist Composition]

After each composition was stored at 25° C. for 1 month, a degree of fluctuation in the sensitivity (in the sensitivity measured in the [Sensitivity] above) before and after the storage was evaluated. This evaluation was based on the following criteria.

(Evaluation Criteria)

A (Good): when fluctuation of sensitivity is less than 1 μC/cm²

B (Fair): when fluctuation of sensitivity is 1 μC/cm² or more and 3 μC/cm² or less C (Insufficient): when fluctuation of sensitivity is higher than 3 μC/cm².

Evaluation results are noted in Tables 8 and 9.

TABLE 8

(electron beam exposure; negative type)

| Example | Composition | Sensitivity (μC/cm²) | Resolution (nm) | Pattern shape | LER (nm) | Scum | Temporal stability |
|---|---|---|---|---|---|---|---|
| 1E | N1 | 15.2 | 25 | rectangle | 4.0 | AA | A |
| 2E | N2 | 15.0 | 25 | rectangle | 4.0 | AA | A |
| 3E | N3 | 15.2 | 25 | rectangle | 4.0 | AA | A |
| 4E | N4 | 15.2 | 25 | rectangle | 4.0 | AA | A |
| 5E | N5 | 15.3 | 30 | rectangle | 4.5 | AA | B |
| 6E | N6 | 15.3 | 30 | rectangle | 4.5 | AA | B |
| 7E | N7 | 15.0 | 25 | rectangle | 4.0 | AA | A |
| 8E | N8 | 15.2 | 25 | rectangle | 4.0 | AA | A |
| 9E | N9 | 15.2 | 30 | rectangle | 4.5 | AA | A |
| 10E | N10 | 15.2 | 25 | rectangle | 4.0 | AA | A |
| 11E | N11 | 15.3 | 30 | rectangle | 4.5 | AA | A |
| 12E | N12 | 15.2 | 25 | rectangle | 4.5 | AA | A |
| 13E | N13 | 15.3 | 25 | rectangle | 4.0 | AA | A |
| 14E | N14 | 15.5 | 30 | rectangle | 4.9 | AA | A |
| 15E | N15 | 15.3 | 30 | rectangle | 4.5 | AA | A |

TABLE 9

(subsequent to Table 8, electron beam exposure; negative type)

| Example | Composition | Sensitivity (μC/cm²) | Resolution (nm) | Pattern shape | LER (nm) | Scum | Temporal stability |
|---|---|---|---|---|---|---|---|
| Comparative Example 1E | Comparative composition N1 | 15.8 | 40 | inverse taper | 5.5 | B | A |
| Comparative Example 2E | Comparative composition N2 | 15.9 | 40 | slightly inverse taper | 5.0 | A | C |
| Comparative Example 3E | Comparative composition N3 | 15.5 | 40 | slightly inverse taper | 5.0 | A | C |
| Comparative Example 4E | Comparative composition N4 | 15.8 | 40 | slightly inverse taper | 5.0 | A | C |
| Comparative Example 5E | Comparative composition N5 | 15.9 | 40 | slightly inverse taper | 5.0 | A | C |

As clearly found from the results noted in Tables 8 and 9, Comparative Examples 1E to 5E which did not use the compound represented by Formula (I) were poor in the sensitivity, resolution, pattern shape, and LER performance. Comparative Examples 2E to 5E were good in the scum reduction, but poor in the temporal stability of a resist composition.

Meanwhile, it was found that Examples 1E to 15E which used the compound represented by Formula (I) were excellent in the sensitivity, scum performance, resolution, pattern shape and LER performance.

Examples 1R to 5R and Comparative Examples 1R to 4R

EUV (Resist Evaluation)

The negative-type resist solution prepared as described above, noted in Table 10 below, was uniformly coated using a spin coater, on a silicon substrate subjected to a hexamethyldisilazane treatment, and heated and dried at 100° C. for 60 sec on a hot plate to form a resist film with a film thickness of 50 nm.

On the obtained resist film, the sensitivity, resolution, pattern shape, line edge roughness (LER), scum and temporal stability of a resist composition were evaluated by the following methods.

[Sensitivity]

The obtained resist film was exposed by using EUV light (wavelength 13 nm) through a reflective mask of a 1:1-line&space pattern with a line width of 50 nm while changing an exposure amount by 0.1 mJ/cm² each time in a range of 0 to 20.0 mJ/cm², and then baked at 110° C. for 90 sec. Then, the film was developed using 2.38% by mass of tetramethylammonium hydroxide (TMAH) aqueous solution.

The exposure amount reproducing the mask pattern of a 1:1-line&space with a line width of 50 nm was set as sensitivity. A smaller value indicates a higher sensitivity.

[Resolution]

The limiting resolution (the minimum line width when the line and space were separated and resolved (line:space=1:1)) at the exposure amount exhibiting the sensitivity was set as resolution (nm).

[Pattern Shape]

The cross-sectional shape of the resist pattern with a line width of 50 nm (line:space=1:1) at the exposure amount exhibiting the sensitivity was observed by a scanning electron microscope (S-4300, manufactured by Hitachi Ltd.). The cross-sectional shape of the line pattern was rated "inverse taper" when the ratio represented by [line width in the top portion (surface portion) of line pattern/line width in the middle portion of line pattern (the position of half the height of line pattern)] is 1.5 or more, rated "slightly inverse taper" when the ratio above is 1.2 or more and less than 1.5, and rated "rectangle" when the ratio above is less than 1.2.

[Line Edge Roughness (LER)]

A resist pattern having a line width 50 nm (line:space=1:1) was formed with the exposure amount exhibiting the sensitivity. Then, at arbitrary 30 points included in its longitudinal 50 m region, the distance from a reference line where the edge should be present was measured using a scanning electron microscope (S-9220 manufactured by Hitachi Ltd.). Then, the standard deviation of the measured distances was determined, and 3σ was calculated. A smaller value indicates a better performance.

[Scum Evaluation]

The line pattern was formed by the same method as described above in the [pattern shape]. Then, the cross-sectional SEM was acquired by S4800 (manufactured by Hitachi High-Technologies Corporation), and the residue in the space portion was observed and evaluated as follows.

AA: scum is not seen.
A: scum is seen but connection is not present between patterns.
B: scum is seen and connection is partially present between patterns.

[Temporal Stability of Resist Composition]

After each composition was stored at a room temperature for 1 month, a degree of fluctuation in the sensitivity (in the sensitivity measured in the [Sensitivity] above) before and after the storage was evaluated. This evaluation was based on the following criteria.

(Evaluation Criteria)
A (Good): when fluctuation of sensitivity is less than 1 mJ/cm$^2$
B (Fair): when fluctuation of sensitivity is 1 mJ/cm$^2$ or more and 3 mJ/cm$^2$ or less
C (Insufficient): when fluctuation of sensitivity is higher than 3 mJ/cm$^2$.

Evaluation results are noted in Table 10.

As clearly found from the results noted in Table 10, Comparative Examples 1R to 4R which did not use the compound represented by Formula (I) were poor in the sensitivity, resolution, pattern shape, and LER performance. Also, particularly, Comparative Examples 2R to 4R were good in the scum reduction, but poor in the temporal stability of a resist composition.

Meanwhile, it was found that Examples 1R to 5R which used the compound represented by Formula (I) were excellent particularly in the sensitivity and scum performance, and excellent in the resolution, pattern shape and LER performance.

Examples 1-1 to 1-5 and Comparative Examples 1-1 and 1-2

Synthesis Example C-1

Synthesis of Copolymer [C-1]

2,2'-azobisisobutyronitrile (5 parts by mass) and propylene glycol monomethyl ether acetate (250 parts by mass) were charged to a flask provided with a cooling tube and a stirrer, and methacrylic acid (18 parts by mass), methacrylic acid tricyclo[5.2.1.02,6]decane-8-yl (25 parts by mass), styrene (5 parts by mass), 2-hydroxyethyl methacrylate ester (30 parts by mass), and benzyl methacrylate (22 parts by mass) were added thereto, followed by nitrogen substitution. Then, the mixture was slowly stirred, and the temperature of the solution was raised up to 70° C. While the temperature was maintained for 5 hours, through polymerization, a copolymer [C-1] solution with a solid concentration 28.8% was obtained. On the obtained copolymer [C-1], Mw was measured using the following apparatus and conditions, and was 13,000. Hereinafter, the structural formula of the repeating unit of the copolymer [C-1], and the ratio (molar ratio) and the polydispersity will be described.

TABLE 10

(EUV exposure; negative type)

| Example | Composition | Sensitivity (mJ/cm$^2$) | Resolution (nm) | Pattern shape | LER (nm) | Scum | Temporal stability |
|---|---|---|---|---|---|---|---|
| 1R | N1 | 10.8 | 25 | rectangle | 4.5 | AA | A |
| 2R | N2 | 10.8 | 25 | rectangle | 4.5 | AA | A |
| 3R | N3 | 10.8 | 25 | rectangle | 4.5 | AA | A |
| 4R | N4 | 10.7 | 25 | rectangle | 4.5 | AA | A |
| 5R | N5 | 10.8 | 30 | rectangle | 5.0 | AA | B |
| Comparative Example 1R | Comparative composition N1 | 12.9 | 40 | inverse taper | 5.5 | B | A |
| Comparative Example 2R | Comparative composition N2 | 12.9 | 40 | slightly inverse taper | 5.5 | A | C |
| Comparative Example 3R | Comparative composition N3 | 12.9 | 40 | slightly inverse taper | 5.5 | A | C |
| Comparative Example 4R | Comparative composition N4 | 13.9 | 40 | slightly inverse taper | 5.5 | A | C |

[Chem. 66]

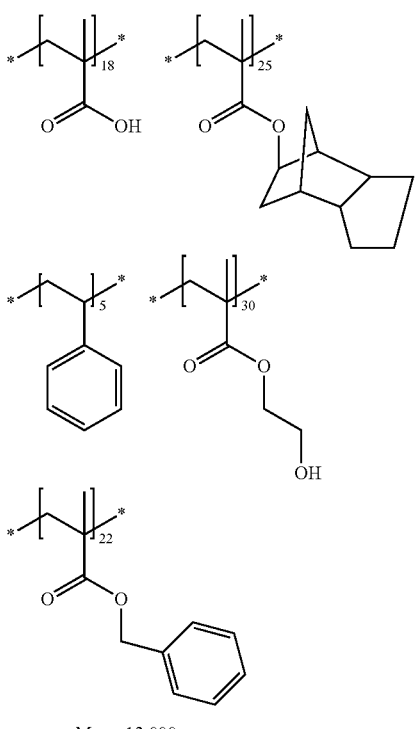

[C-1]

Mw = 13,000
Mw/Mn = 1.54

Apparatus: GPC-101 (manufactured by Showa Denko K.K.)

Column: GPC-KF-801, GPC-KF-802, GPC-KF-803 and GPC-KF-804 in combination

Mobile phase: tetrahydrofuran

<Preparation of Photocurable Composition>

Example 1-1

A solution containing the compound [A-1] below in an amount corresponding to 1 parts by mass (solid content) was mixed with a photobase generator B-1 (1 parts by mass), a bisphenol A type epoxy resin (EPIKOTE 1001, manufactured by Japan Epoxy Resins Co., Ltd.) (100 parts by mass), and a fluorine-based surfactant ("FTX-218" manufactured by Neos Corporation) (0.3 parts by mass) as a surfactant. The resultant mixture was dissolved in diethylene glycol-ethyl methyl ether to have a solid concentration of 20% by mass, and was filtered through a membrane filter with a pore diameter of 0.2 µm to prepare a solution of a photocurable composition.

[Chem. 67]

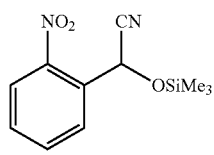

[A-1]

Examples 1-2 to 1-5 and Comparative Example 1-1 and 1-2

A solution of a photocurable composition was prepared in the same manner as in Example 1-1 except that the kinds and amounts as noted in Table 11 were used.

In Table 11, abbreviations for components mean the following compounds, respectively.

D-1: bisphenol A novolak type epoxy resin ("EPIKOTE 1001" manufactured by Japan Epoxy Resins Co., Ltd.)

D-2: phenol novolak type epoxy resin ("EPIKOTE 152" manufactured by Japan Epoxy Resins Co., Ltd.)

<Evaluation of Characteristics of Photocurable Composition and Cured Film>

Evaluation on the photocurable composition prepared as described above, and a cured film formed of the photocurable composition was performed as follows. The evaluation results are noted in Table 11.

[Evaluation of Radiation Sensitivity of Photocurable Composition]

On a non-alkali glass substrate, each solution of a photocurable composition was coated by a spinner, and pre-baked on a hot plate of 90° C. for 3 min to form a film of the photocurable composition (film thickness: 3.0 m). On the obtained film, exposure was performed using a high-pressure mercury lamp without using a photomask, while varying the exposure amount.

On the obtained cured film, a pencil scratch test was performed in accordance with JIS-K5400-1990, 8.4.1 to measure a pencil hardness (surface hardness) of the cured film. Here, an exposure amount when the surface hardness becomes H or more was obtained. When the exposure amount is 1,000 J/m² or less, it can be said that the radiation sensitivity is good. The exposure amount when the surface hardness is H or more is noted in Table 11.

[Evaluation of Solvent Resistance]

A coating film with a film thickness of 3.0 m was formed on a glass substrate in the same manner as in [Evaluation of radiation sensitivity of photocurable composition]. The obtained coating film was irradiated with ultraviolet rays by a mercury lamp so that the cumulative irradiation dose becomes 2,000 J/m², and then the film thickness (T1) of the cured film was measured.

Then, the film was immersed in acetone for 20 min, and the film thickness (t1) after the immersion was measured. These values were applied in the following equation so as to obtain a film thickness change rate (%).

Film thickness change rate (%)=(t1−T1)/T1×100

The measurement results are noted in Table 11. When the film thickness change rate is 5% or less, it can be said that the solvent resistance is good.

[Evaluation of Temporal Stability]

The photocurable composition prepared as described above was stored at a room temperature for 1 month, and a degree of fluctuation in the sensitivity (in the sensitivity measured in the [Sensitivity] above) before and after the storage was evaluated. This evaluation was based on the following criteria.

(Evaluation Criteria)

A (Good): when fluctuation of sensitivity is less than 10 J/cm²

B (Fair): when fluctuation of sensitivity is 10 J/cm² or more and 30 J/cm² or less C (Insufficient): when fluctuation of sensitivity is higher than 30 J/cm².

The evaluation results as above are noted in Table 11.

TABLE 11

|  | Example 1-1 | Example 1-2 | Example 1-3 | Example 1-4 | Example 1-5 | Comparative Example 1-1 | Comparative Example 1-2 |
|---|---|---|---|---|---|---|---|
| Photobase generator (parts by mass) | B-1 (1) | B-6 (1) | B-19 (1) | B-22 (1) | B-26 (1) | AC3 (1) | AC4 (1) |
| D-1 (parts by mass) | 100 | 100 | 100 |  | 10 | 100 | 100 |
| D-2 (parts by mass) |  |  |  | 50 |  |  |  |
| C-1 (parts by mass) |  |  |  | 50 | 90 |  |  |
| Radiation sensitivity (J/m$^2$) | 300 | 400 | 400 | 400 | 500 | 1500 | 1000 |
| Solvent resistance (film thickness change rate (%)) | 2 | 3 | 3 | 2 | 3 | 30 | 35 |
| Temporal stability | A | A | A | A | A | C | C |

As clearly found from the results noted in Table 11, when the photosensitive composition containing the compound represented by Formula (I) is used as a photocurable composition, the radiation sensitivity and the temporal stability are excellent, and also the solvent resistance of a formed film is excellent.

Examples 2-1 to 2-5 and Comparative Examples 2-1 and 2-2

Using a polyamic acid as a base-reactive resin, a dark reaction of a photobase generator, and a performance as an imidization catalyst thereof were evaluated. Also, the polyamic acid used for the evaluation was synthesized by the following method.

A 1 L separable three-necked flask attached with a stirrer was used. Under a nitrogen stream, γ-butyrolactone (80 g, manufactured by Wako Pure Chemical Industries, Ltd.), 1,3-bis(4-aminophenoxy) benzene (9.41 g, 33.1 mmol) (Wakayama Seika Kogyo Co., Ltd.), and oxydiphthalic acid dianhydride (10.3 g, 33.2 mmol) (manufactured by Manac Co., Ltd.) were charged and stirred at a room temperature for 5 hours. The polymer concentration of the obtained polyamic acid solution was 20% by mass.

The obtained polyamic acid solution (2.5 g), a photobase generator (65 mg), and γ-butyrolactone (0.5 ml) were blended with each other to obtain a photocurable composition. On a silicon wafer, the photocurable composition was spin-coated, and dried at 95° C. for 15 min to form a curable film with a thickness of 1 m.

[Thermal Stability]

The curable film was exposed using a high-pressure mercury lamp at an exposure amount of 2000 mJ/m$^2$ so that an exposed portion and an unexposed portion were formed, and was subjected to post-exposure baking (PEB) at 140° C. for 5 min, 10 min, 15 min and 30 min. Also, in order to carry out imidization completely, the film was heated at 180° C. for 1 hour. The absorption derived from an imide group was measured by FT-IR to calculate an imidization rate. Using a sample of only a polyamic acid as a blank, the imidization rate was measured in the same manner, and a difference between the imidization rate (%) of the blank and the imidization rate (%) of the unexposed portion was evaluated as a thermal stability. When the PEB was performed for 30 min, a thermal stability less than 10% was rated A, and a thermal stability of 10% or more was rated B.

[Reaction Contrast]

Also, from the imidization rate of the exposed portion and the imidization rate of the unexposed portion, a reaction contrast was evaluated. The result of the difference between the imidization rate (%) of the exposed portion and the imidization rate (%) of the unexposed portion is noted in Table 12.

TABLE 12

|  | Example 2-1 | Example 2-2 | Example 2-3 | Example 2-4 | Example 2-5 | Comparative Example 2-1 | Comparative Example 2-2 |
|---|---|---|---|---|---|---|---|
| Photobase generator | B-1 | B-6 | B-19 | B-22 | B-26 | AC3 | AC4 |
| Thermal stability | A | A | A | A | A | B | B |
| Reaction contrast (%) | 70% | 60% | 70% | 70% | 50% | 20% | 30% |

As clearly found from the results noted in Table 12, when the photosensitive composition containing the compound represented by Formula (I) is used as a photocurable composition, the reaction contrast and the thermal stability are excellent.

Examples 3-1 to 3-5 and Comparative Examples 3-1 and 3-2

Patterning Evaluation

Then, a patterning evaluation was performed. Meanwhile, a polyamic acid used for the evaluation was synthesized by the following method.

A 1 L separable three-necked flask attached with a stirrer was used. Under a nitrogen stream, N-methylpyrrolidone (47 g, manufactured by Wako Pure Chemical Industries, Ltd.), 1,3-bis(4-aminophenoxy)benzene (5.61 g, 19.2 mmol) (manufactured by Wakayama Seika Kogyo Co., Ltd.), and oxydiphthalic acid dianhydride (6.2 g, 20 mmol) (manufactured by Manac Co., Ltd.) were charged and stirred at a room temperature for 5 hours. The polymer concentration of the obtained polyamic acid solution was 20% by mass.

The obtained polyamic acid solution (5 g), a photobase generator (100 mg), and diethyl thioxanthone (50 mg) (manufactured by Wako Pure Chemical Industries, Ltd.) were blended with each other to obtain a photocurable composition. The obtained photocurable composition was coated on a kapton film with a thickness of 25 m (Kapton EN-100/manufactured by Du Pont-Toray Co., Ltd.) by a blade coater, and dried at 95° C. for 12 min in an oven to obtain a film with a film thickness of 1 μm.

On the obtained film, a contact exposure was performed through a negative-type mask using an ultra-high pressure mercury lamp (manufactured by OAK Corporation, product name: HMW-201 KB). The exposure amount was 1,000 mJ/cm². After the exposure, the film was heated in an oven of 110° C. for 20 min. A spray development was performed using 1% by mass of sodium carbonate aqueous solution at a development temperature of 30° C. and a spray pressure of 0.2 MPa. A spray washing was performed using distilled water of 30° C. at a spray pressure of 0.2 MPa, and a residual film ratio was measured. The film thickness was measured using a film thickness meter (ID-C112B, manufactured by Mitutoyo Corp.).

The developability was rated A when the development time was not greater than 90 sec, and was rated B when the development time exceeded 90 sec.

As clearly found from the results noted in Table 13, when the photosensitive composition containing the compound represented by Formula (I) is used as a photocurable composition, the developability is excellent and the residual film ratio of a formed film is excellent.

INDUSTRIAL APPLICABILITY

According to the present invention, there is provided a photosensitive composition which contains a compound having a specific structure and thus efficiently generates a base. Particularly, when the photosensitive composition is used as a photocurable composition, the sensitivity, reaction contrast and developability are excellent, and the residual film ratio, solvent resistance and thermal stability of a formed cured film are excellent, and when the photosensitive composition is used as a resist composition, the resolution, and LER performance, and the shape and scum performance of a formed pattern are excellent.

While the present invention has been described in detail with reference to specific embodiments, it is apparent to those skilled in the art that various changes and modifications may be made without departing from the spirit and scope of the present invention.

This application is based on Japanese Patent Application filed on Feb. 21, 2013 (Japanese Patent Application No. 2013-032585), the contents of which are incorporated herein by reference.

The invention claimed is:

1. A photosensitive composition containing a compound represented by the following Formula (I):

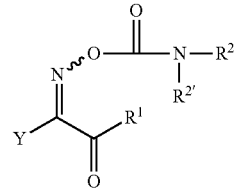

Formula (I)

in Formula (I),

Y represents a monovalent organic group that is heterocyclic, $R^1$ represents a monovalent organic group, each of $R^2$ and $R^{2'}$ independently represents a hydrogen atom, an alkyl group, a cycloalkyl group, an aryl group, or a heteroaryl group, and $R^2$ and $R^{2'}$ may be bound with each other to form a nitrogen-containing heterocyclic group.

2. The photosensitive composition as claimed in claim 1, wherein the compound represented by Formula (I) is a compound represented by the following Formula (II):

TABLE 13

| | Example 3-1 | Example 3-2 | Example 3-3 | Example 3-4 | Example 3-5 | Comparative Example 3-1 | Comparative Example 3-2 |
|---|---|---|---|---|---|---|---|
| Photobase generator | B-1 | B-6 | B-19 | B-22 | B-26 | AC3 | AC4 |
| Residual film ratio (%) | 95% | 90% | 95% | 95% | 80% | 30% | 40% |
| Developability | A | A | A | A | A | B | B |

Formula (II)

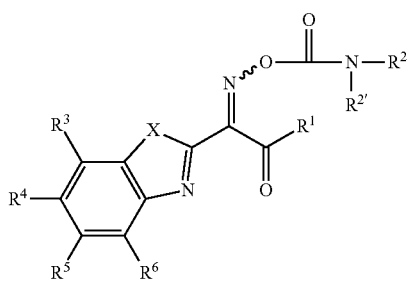

in Formula (II),
each of $R^3$ to $R^6$ independently represents a hydrogen atom, an alkyl group, an aryl group or a halogen atom, provided that, $R^3$ and $R^4$, $R^4$ and $R^5$, or $R^5$ and $R^6$ may be bound with each other to form an alicyclic or aromatic ring, X represents —O— or —S—, $R^1$, $R^2$ and $R^{2'}$ are the same as $R^1$, $R^2$ and $R^{2'}$ in Formula (I) above, respectively, $R^2$ and $R^{2'}$ may be bound to each other to form a nitrogen-containing heterocyclic group.

3. A photocurable composition containing the photosensitive composition claimed in claim 1, wherein the photosensitive composition further contains a base-reactive compound.

4. The photocurable composition as claimed in claim 3, wherein the base-reactive compound is an epoxy resin.

5. The photocurable composition as claimed in claim 3, wherein the base-reactive compound is a polyamic acid.

6. A chemical amplification resist composition containing the photosensitive composition claimed in claim 1, wherein the photosensitive composition further contains a compound capable of generating an acid upon irradiation with an actinic ray or radiation.

7. The chemical amplification resist composition as claimed in claim 6, containing a resin (E) having a repeating unit represented by the Formula (1):

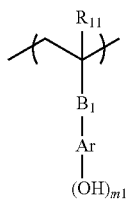

(1)

in Formula (1),
$R_{11}$ represents a hydrogen atom, a methyl group which may have a substituent, or a halogen atom,
$B_1$ represents a single bond or a divalent organic group,
Ar represents an aromatic ring group, and
m1 represents an integer of 1 or more.

8. The chemical amplification resist composition as claimed in claim 6, which is used for exposure of electron beam or extreme-ultraviolet rays.

9. A resist film formed using the chemical amplification resist composition claimed in claim 6.

10. A pattern forming method comprising:
exposing the resist film claimed in claim 9; and
developing the exposed resist film.

11. A method of manufacturing an electronic device, comprising the pattern forming method claimed in claim 10.

12. A photosensitive composition containing a compound represented by the following Formula (I):

Formula (I)

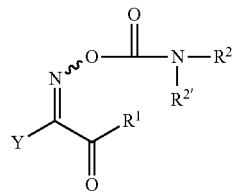

in Formula (I),
Y represents a monovalent organic group,
$R^1$ represents a monovalent organic group,
each of $R^2$ and $R^{2'}$ independently represents a hydrogen atom, an alkyl group, a cycloalkyl group, an aryl group, or a heteroaryl group, and $R^2$ and $R^{2'}$ may be bound with each other to form a nitrogen-containing heterocyclic group, wherein the photosensitive composition further contains a compound capable of generating an acid upon irradiation with an actinic ray or radiation, and wherein the photosensitive composition further contains a resin (C) having a repeating unit having a group capable of decomposing by the action of an acid to generate a polar group.

13. The photosensitive composition according to claim 12, wherein the repeating unit in the resin (C) having a group capable of decomposing by the action of an acid to generate a polar group is represented by Formula (A):

(A)

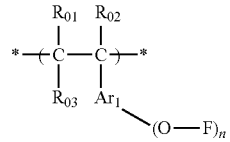

in Formula (A), each of $R_{01}$, $R_{02}$ and $R_{03}$ independently represents a hydrogen atom, an alkyl group, a cycloalkyl group, a halogen atom, a cyano group or an alkoxycarbonyl group, $Ar_1$ represents an alkylene group or an aromatic ring group, $R_{03}$ may be an alkylene group, and may be bound to $Ar_1$ as an aromatic ring group to form a ring together with a —C—C— chain, n represents an integer of 1 to 4,
each of n F's independently represents a hydrogen atom or a group capable of leaving by the action of an acid, and at least one F represents a group capable of leaving by the action of an acid, wherein the group capable of leaving by the action of an acid is represented by Formula (B):

(B)

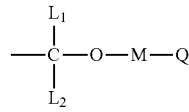

in Formula (B),
each of $L_1$ and $L_2$ independently represents a hydrogen atom, an alkyl group, a cycloalkyl group, an aryl group, or an aralkyl group, M represents a single bond or a divalent linking group,
Q represents an alkyl group, a cycloalkyl group, a cyclic aliphatic group, aromatic ring group, an amino group, an ammonium group, a mercapto group, a cyano group, or an aldehyde group, and the cyclic aliphatic groups and aromatic ring groups may contain a hetero atom.

14. The photosensitive composition according to claim 12, wherein the repeating unit in the resin (C) having a group capable of decomposing by the action of an acid to generate a polar group is represented by Formula (X):

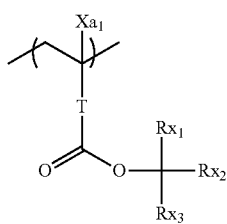
(X)

in Formula (X), $Xa_1$ represents a hydrogen atom, a methyl group, a trifluoromethyl group, or a hydroxymethyl group, T represents a single bond or a divalent linking group, and each of $Rx_1$ to $Rx_3$ independently may be a linear or branched alkyl group or a monocyclic or polycyclic cycloalkyl group, and at least two of $Rx_1$ to $Rx_3$ may be bound to each other to form a monocyclic or polycyclic cycloalkyl group.

15. A photosensitive composition containing a compound represented by the following Formula (I):

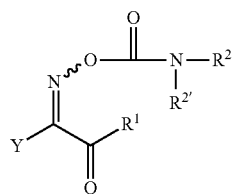
Formula (I)

in Formula (I),

Y represents a monovalent organic group, $R^1$ represents a monovalent organic group, each of $R^2$ and $R^{2'}$ independently represents a hydrogen atom, an alkyl group, a cycloalkyl group, an aryl group, or a heteroaryl group, and $R^2$ and $R^{2'}$ may be bound with each other to form a nitrogen-containing heterocyclic group, wherein the photosensitive composition further contains a compound capable of generating an acid upon irradiation with an actinic ray or radiation, and wherein the photosensitive composition further contains a crosslinking agent (D).

16. The photosensitive composition according to claim 15, wherein the crosslinking agent (D) contains a compound having two or more hydroxyl methyl groups or alkoxy methyl groups.

17. The photosensitive composition according to claim 15, wherein the photosensitive composition further contains a compound (E) having a repeating unit represented by Formula (3),

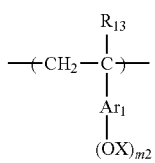
(3)

in Formula (3), $R_{13}$ represents a hydrogen atom or a methyl group,

X represents a group having a non-acid-decomposable polycyclic alicyclic hydrocarbon structure, $Ar_1$ represents an aromatic ring, and m2 is an integer of 1 or more.

* * * * *